United States Patent
Chapman et al.

(10) Patent No.: US 10,289,804 B2
(45) Date of Patent: May 14, 2019

(54) METHOD OF INCREASING EFFICIENCY IN A MEDICAL CLAIM TRANSACTION, AND COMPUTER PROGRAM CAPABLE OF EXECUTING SAME

(75) Inventors: Sherwood Chapman, Gilbert, AZ (US); J. Mikel Echeverria, Phoenix, AZ (US)

(73) Assignee: Cognizant TriZetto Software Group, Inc., Englewood, CO (US)

( * ) Notice: Subject to any disclaimer, the term of this patent is extended or adjusted under 35 U.S.C. 154(b) by 3366 days.

(21) Appl. No.: 11/018,189

(22) Filed: Dec. 20, 2004

(65) Prior Publication Data

US 2005/0108067 A1    May 19, 2005

Related U.S. Application Data

(62) Division of application No. 09/489,614, filed on Jan. 21, 2000, now Pat. No. 6,879,959.

(51) Int. Cl.
*G06Q 40/08* (2012.01)
*G06Q 40/02* (2012.01)
(Continued)

(52) U.S. Cl.
CPC ........... *G06F 19/328* (2013.01); *G06Q 10/10* (2013.01); *G06Q 40/02* (2013.01); *G06Q 40/08* (2013.01); *G06Q 50/22* (2013.01)

(58) Field of Classification Search
CPC ........ G06Q 40/08; G06Q 40/02; G06Q 50/22; G06Q 10/10

(Continued)

(56) References Cited

U.S. PATENT DOCUMENTS 4,491,725 A    1/1985 Pritchard .................... 705/2
4,831,526 A    5/1989 Luchs et al.
(Continued)

FOREIGN PATENT DOCUMENTS

DE    19641357    9/1998    ............ G06F 17/60
JP    11242270    9/1999    ............ G03B 15/05
(Continued)

OTHER PUBLICATIONS

"National Health Plan Identifier, The Establishment of a Standard for a National Health Plan Identifier Issue Paper" [online], Mar. 11, 1998 [retrieved on Dec. 14, 2010], 13 pp., Retrieved from the Internet: http://www.payorid.com/Medicare/HIPAA.htm.
(Continued)

*Primary Examiner* — Robert A Sorey
*Assistant Examiner* — Kristine K Rapillo
(74) *Attorney, Agent, or Firm* — Dawn-Marie Bey; Bey & Cotropia PLLC

(57) ABSTRACT

A method of adjudicating a medical claim includes providing a requirements for a first claim and a second claim, receiving a medical claim for a medical procedure, setting a first score for the first claim and a second score for the second claim to an initial value, comparing components of the medical claim to the requirements of the first and second claims, changing the first and second scores for each one of the components that match one of the requirements and for each one of the requirements that is missing from the components, and selecting the first or second claim based upon predetermined criteria applied to their respective scores to determine either a monetary value of the medical procedure for a medical service provider associated with the medical procedure or a monetary value of medical coverage for a patient associated with the medical procedure.

10 Claims, 38 Drawing Sheets

(51) Int. Cl.
   *G06Q 50/22*     (2018.01)
   *G06Q 10/10*     (2012.01)
   *G06F 19/00*     (2018.01)
(58) Field of Classification Search
   USPC .................................................. 705/4
   See application file for complete search history.

(56) References Cited

U.S. PATENT DOCUMENTS

| | | | |
|---|---|---|---|
| 4,858,121 A | 8/1989 | Barber et al. | 705/2 |
| 4,916,611 A * | 4/1990 | Doyle et al. | 705/2 |
| 4,987,538 A | 1/1991 | Johnson et al. | |
| 5,070,452 A | 12/1991 | Doyle | |
| 5,134,564 A | 7/1992 | Dunn et al. | 705/33 |
| 5,202,827 A | 4/1993 | Sober | |
| 5,225,976 A | 7/1993 | Tawil | |
| 5,235,507 A | 8/1993 | Sackler et al. | 705/2 |
| 5,235,702 A | 8/1993 | Miller | |
| 5,253,164 A | 10/1993 | Holloway et al. | 705/2 |
| 5,301,105 A | 4/1994 | Cummings, Jr. | 705/2 |
| 5,324,077 A | 6/1994 | Kessler et al. | 283/54 |
| 5,325,290 A | 6/1994 | Cauffman et al. | |
| 5,333,317 A | 7/1994 | Dann | |
| 5,359,509 A * | 10/1994 | Little et al. | 705/2 |
| 5,471,382 A | 11/1995 | Tallman et al. | 600/300 |
| 5,517,405 A | 5/1996 | McAndrew et al. | 706/45 |
| 5,519,607 A | 5/1996 | Tawil | |
| 5,523,942 A | 6/1996 | Tyler | |
| 5,544,044 A | 8/1996 | Leatherman | 705/3 |
| 5,560,008 A | 9/1996 | Johnson | |
| 5,583,760 A | 12/1996 | Klesse | 705/38 |
| 5,644,778 A * | 7/1997 | Burks et al. | 705/2 |
| 5,692,501 A | 12/1997 | Minturn | 600/301 |
| 5,696,906 A | 12/1997 | Peters et al. | |
| 5,704,044 A | 12/1997 | Tarter et al. | 705/4 |
| 5,715,397 A | 2/1998 | Ogawa | |
| 5,724,379 A | 3/1998 | Perkins et al. | 705/2 |
| 5,737,539 A | 4/1998 | Edelson et al. | |
| 5,794,221 A | 8/1998 | Egendorf | |
| 5,832,447 A | 11/1998 | Rieker et al. | 705/2 |
| 5,832,460 A | 11/1998 | Bednar et al. | |
| 5,835,897 A | 11/1998 | Dang | |
| 5,845,254 A * | 12/1998 | Lockwood et al. | 705/2 |
| 5,852,812 A | 12/1998 | Reeder | |
| 5,879,163 A | 3/1999 | Brown et al. | 434/236 |
| 5,903,873 A | 5/1999 | Peterson et al. | |
| 5,911,132 A | 6/1999 | Sloane | |
| 5,915,241 A | 6/1999 | Giannini | 705/2 |
| 5,920,847 A | 7/1999 | Kolling et al. | |
| 5,924,074 A | 7/1999 | Evans | |
| 5,930,759 A | 7/1999 | Moore et al. | 705/2 |
| 5,950,169 A | 9/1999 | Borghesi et al. | 705/4 |
| 5,970,463 A | 10/1999 | Cave et al. | 705/3 |
| 5,974,389 A | 10/1999 | Clark et al. | |
| 5,991,733 A | 11/1999 | Aleia et al. | 705/8 |
| 5,995,939 A | 11/1999 | Berman et al. | |
| 6,003,007 A | 12/1999 | DiRienzo | |
| 6,012,035 A | 1/2000 | Freeman, Jr. et al. | 705/2 |
| 6,044,362 A | 3/2000 | Neely | |
| 6,047,259 A | 4/2000 | Campbell et al. | |
| 6,052,674 A | 4/2000 | Zervides et al. | |
| 6,088,677 A | 7/2000 | Spurgeon | 705/4 |
| 6,092,055 A | 7/2000 | Owens et al. | |
| 6,112,183 A | 8/2000 | Swanson et al. | 705/2 |
| 6,151,581 A | 11/2000 | Kraftson et al. | |
| 6,163,770 A | 12/2000 | Gamble | |
| 6,199,115 B1 | 3/2001 | DiRienzo | |
| 6,208,973 B1 * | 3/2001 | Boyer | G06Q 20/02 705/2 |
| 6,208,974 B1 | 3/2001 | Campbell et al. | |
| 6,253,186 B1 | 6/2001 | Pendleton, Jr. | 705/2 |
| 6,283,761 B1 | 9/2001 | Joao | 434/236 |
| 6,285,991 B1 | 9/2001 | Powar | |
| 6,304,857 B1 | 10/2001 | Heindel et al. | |
| 6,324,516 B1 * | 11/2001 | Shults et al. | 705/2 |
| 6,341,265 B1 | 1/2002 | Provost et al. | 705/4 |
| 6,343,271 B1 | 1/2002 | Peterson et al. | 705/4 |
| 6,345,260 B1 | 2/2002 | Cummings, Jr. et al. | |
| 6,374,229 B1 | 4/2002 | Lowrey et al. | |
| 6,453,297 B1 | 9/2002 | Burks et al. | 705/3 |
| 6,587,829 B1 | 7/2003 | Camarda et al. | 705/3 |
| 6,735,569 B1 | 5/2004 | Wizig | 705/4 |
| 6,757,898 B1 | 6/2004 | Ilsen et al. | |
| 6,879,959 B1 * | 4/2005 | Chapman et al. | 705/2 |
| 6,915,265 B1 | 7/2005 | Johnson | 705/2 |
| 6,947,907 B1 | 9/2005 | Silverman | |
| 7,016,856 B1 | 3/2006 | Wiggins | 705/2 |
| 7,194,416 B1 | 3/2007 | Provost et al. | 705/4 |
| 7,344,496 B2 | 3/2008 | Iliff | 600/300 |
| 7,464,040 B2 | 12/2008 | Joao | 705/2 |
| 7,774,252 B2 | 8/2010 | Seare et al. | 705/35 |
| 8,099,302 B2 * | 1/2012 | Chapman et al. | 705/2 |
| 8,494,876 B2 * | 7/2013 | Chapman et al. | 705/2 |
| 2002/0004725 A1 | 1/2002 | Martin | |
| 2002/0019754 A1 | 2/2002 | Peterson et al. | 705/4 |
| 2002/0046165 A1 | 4/2002 | Kitchen et al. | |
| 2002/0049617 A1 | 4/2002 | Lencki et al. | |
| 2002/0077854 A1 | 6/2002 | Porterfield | |
| 2002/0077869 A1 | 6/2002 | Doyle et al. | 705/4 |
| 2002/0138304 A1 | 9/2002 | Fontanesi | 705/2 |
| 2003/0046116 A1 | 3/2003 | Horowitz et al. | 705/4 |
| 2003/0055679 A1 | 3/2003 | Soll | |
| 2005/0187797 A1 | 8/2005 | Johnson | 705/3 |
| 2005/0247777 A1 | 11/2005 | Pitroda | 235/380 |
| 2007/0203834 A1 | 8/2007 | Field | 705/40 |
| 2010/0235197 A1 | 9/2010 | Dang | 705/3 |
| 2012/0109681 A1 * | 5/2012 | Chapman et al. | 705/2 |

FOREIGN PATENT DOCUMENTS

| | | | |
|---|---|---|---|
| JP | 11242701 A | 9/1999 | |
| JP | 2001-175724 A | 6/2001 | |
| WO | WO 84/01448 | 4/1984 | G06F 3/00 |
| WO | WO 91/15817 * | 10/1991 | G06F 3/00 |
| WO | WO-9115817 A1 * | 10/1991 | G06F 19/328 |
| WO | WO 95/03569 | 2/1995 | G06Q 40/00 |
| WO | WO 95/12857 | 5/1995 | G06Q 17/60 |
| WO | WO 99/22330 | 5/1999 | G06F 19/00 |
| WO | WO 99/44111 | 9/1999 | G06Q 20/00 |
| WO | WO 00/03343 | 1/2000 | G06F 1/00 |
| WO | WO 00/66367 | 11/2000 | B42D 1/10 |
| WO | WO 00/67173 A1 | 11/2000 | |

OTHER PUBLICATIONS

Kirby, William H., Jr., "Computer-Based Applications for Providers, Consumers and Insurers in Health Care Services and Education," *IEEE*, pp. 236-242, 1982.

North Carolina, Industrial Commission, Memorandum, "New Mandatory Medical Billing and Reimbursement Procedures," 2 pp., Nov. 30, 1999.

DownSeeker Scripts, "Free Download MedLink Script," 2 pp., Aug. 29, 1999.

The Free Library, "HNC Insurance Solutions Introduces Autoadvisor, the First Integrated Medical Repricing Software With Managed Care Component for the Auto Medical Claims Market" [online], *Business Wire*, Sep. 2, 1998 [retrieved on Dec. 14, 2010], 4 pp., Retrieved from the Internet: http://www.thefreelibrary.com/HNC+Insurance+Sol . . . .

Selby, Dayton W. and Federico, Robert J., "The Effects of Physicians' Computer Applications on Health Insurance Claims and Reimbursements," *IEEE*, pp. 746-751, 1979.

Miller, Lawrence G., "Reducing Health Care Costs Using Claims Adjudication Software" [online], *Physician Executive*, May 1, 1993 [retrieved on Dec. 14, 2010], 4 pp., Retrieved from the Internet: http://www.thefreelibrary.com/Reducing+health+ca . . . .

Waterhouse, Rosie, "Medical Tests for New Benefit 'Unfair': Over-Reliance on Health Evidence Attacked" [online], The Independent, Feb. 17, 1994 [retrieved on Dec. 20, 2010], 1 p., Retrieved from the Internet: http://www.independent.co.uk/news/uk/politics/medical-tests-for-new-benefit-unfair-overreliance-on-healt . . . .

(56) References Cited

OTHER PUBLICATIONS

Gustafson, Bobette M., "Preparing for Future Roles as Claims Payers" [online], *Healthcare Financial Management*, Jan. 1, 1996 [retrieved on Dec. 14, 2010[, 3 pp., Retrieved from the Internet: http://www.allbusiness.com/.../538143-1.html.

* cited by examiner

350

360, 370

FIG.17c asaunit
- codeid
- effdate
---
- termdate
- basicunits
- createid
- createdate
- updateid
- lastupdate

~1732 drgrate
- codeid
- effdate
- drgroupid (FK)
---
- units
- description
- termdate
- updateid
- lastupdate
- createid
- createdate

~1730 moddiscount
- programid (FK)
- modcode (FK)
---
- paydiscount
- paypercent
- createid
- createdate
- isglobal
- updateid
- lastupdate

~1729

R/1051

```
fundid (FK)
ffspoolid
ffspoolamt
toothnumber
toothsurface
reimburseamt
billservcode
approvedservcode
refundamt
submitdiscount
modcode2
modcode3
addlmemamt
memamt
diag1
diag2
diag3
diag4
globalcovthrudate
```

FIG.21b

FIG.22b benefit
planid (FK)
benefitid
effdate
termdate
description
longdescription
ppoid
riderid (FK)
copayid (FK)
fundid
modelid
modelplanid
ubid
modcode
provtype
status
class
network
ppo
pcpbased
priorauth
gender
visits
occurrances
copay
costshare
percentagecovered
famdeduct
inddeduct
appdeduct
annualmaximum
limitamount
visitterm
limit
agemin
maximum
agemax
monthcovered
billtype
specialtycode
eobflag
visitmax
hasdiag
hasproc
haslocation
limitterm
billclass
facilitytype
ismodel
manualreview
createid
createdate
updateid
lastupdate
hasdocuments
emergencyonly
deductaccumid
maxoutaccumid (FK)
visitaccumid
annualaccumid

~1604 has dental area has covrule annualaccumid
lifetimeaccumid (FK)
hascovrule
initialprothesis
remitid
eobid
familyannual
familymaxout
familylifetime
hasperdiem
perdiemtype
perdiemunits
copayaccumid

FIG.22c

METHOD OF INCREASING EFFICIENCY IN A MEDICAL CLAIM TRANSACTION, AND COMPUTER PROGRAM CAPABLE OF EXECUTING SAME

This application is a divisional application of prior application Ser. No. 09/489,614, filed Jan. 21, 2000 now U.S. Pat. No. 6,879,959 and for which a notice of allowance was mailed on Sep. 20, 2004.

FIELD OF THE INVENTION

This invention relates, in general, to medical plans, and more particularly, to methods of adjudicating medical claims.

BACKGROUND OF THE INVENTION

In existing medical claim submission processes, a medical service provider, such as a doctor, physician, or surgeon, submits a batch of medical claims to a medical plan provider under which at least some of the medical service provider's patients are covered. The medical service provider sends the batch of medical claims either on paper or on a mass media device such as a computer disk or tape. If the medical claims are submitted on paper, the medical plan provider manually enters data from the batch of medical claims into the medical plan provider's computer system. If the medical claims are submitted electronically, the medical plan provider loads the batch of electronic medical claims into the computer system. Next, each individual medical claim in the batch of claims is reviewed manually by a human claims processor. In reviewing each claim, the claims processor manually prices the claim and manually determines the patient's benefits. The claims processor often uses external software products to validate and process complicated claims processing checks. The pricing of the claim and the determination of the patient's benefits may occasionally be performed automatically. After one or two months, the medical plan provider sends a remittance advice to the patient and sends a check to the medical service provider for the medical service provider's medical claim submitted in the batch of medical claims. However, a significant number of the submitted medical claims must be re-processed by the medical service provider due to errors occurring during the manual data entry process, the manual claims pricing process, and/or the manual benefit determination process.

Another problem with the present medical claims processing systems occurs in the area of predetermination or pre-approval. Many complex medical procedures require pre-approval in which coverage for a benefit is determined before the medical procedure is performed. As an example, pre-approval is often required for amalgams or porcelain filings in the field of dentistry. To obtain the pre-approval, the dentist fills out and mails a pre-approval request to the medical plan provider. The medical plan provider enters data from the request into the medical plan provider's computer system, and if the request is approved, the medical plan provider sends back to the dentist a medical claim form that indicates the medical service or services that may be paid for by the medical plan. This lengthy pre-approval process often takes several weeks. Therefore, this pre-approval process is time consuming and is neither patient-oriented nor medical service provider-oriented.

After receiving the pre-approval, the dentist performs the medical procedure, and then the dentist checks off the completed medical procedure on the medical claim form and mails the medical claim form back to the medical plan provider. Upon receiving the medical claim form, the medical plan provider enters the data from the medical claim form into the medical plan provider's computer system. In this manual system, the data for a single medical procedure is recorded four times—twice by the dentist and twice by the medical plan provider. Accordingly, the administrative overhead attendant to this present system is both costly and time consuming.

SUMMARY OF THE INVENTION

In accordance with the principles of the invention, an embodiment of a method of adjudicating a medical claim includes providing requirements for a first claim and a second claim, receiving a medical claim for a medical procedure, setting a first score for the first claim and a second score for the second claim to an initial value, comparing components of the medical claim to the requirements of the first and second claims, changing the first and second scores for each one of the components that match one of the requirements and for each one of the requirements that is missing from the components, and selecting the first or second claim based upon predetermined criteria applied to their respective scores to determine either a monetary value of the medical procedure for a medical service provider associated with the medical procedure or a monetary value of medical coverage for a patient associated with the medical procedure.

BRIEF DESCRIPTION OF THE DRAWING

The invention will be better understood from a reading of the following detailed description taken in conjunction with the accompanying drawing figures in which:

FIGS. 17a through 17f illustrate an inter-relationship of menus for tracking a medical service provider's contract with a medical plan provider in the system in accordance with an embodiment of the invention;

FIGS. 21a and 21b illustrate an inter-relationship of menus for a down-coding process in the system in accordance with an embodiment of the invention; and FIGS. 22a, 22b, and 22c illustrate an inter-relationship of menus for tracking a member's dental benefits in the system in accordance with an embodiment of the invention.

For simplicity and clarity of illustration, descriptions and details of well-known features and techniques are omitted to avoid unnecessarily obscuring the invention, and the same reference numerals in different figures denote the same elements.

DETAILED DESCRIPTION

Figure 1:
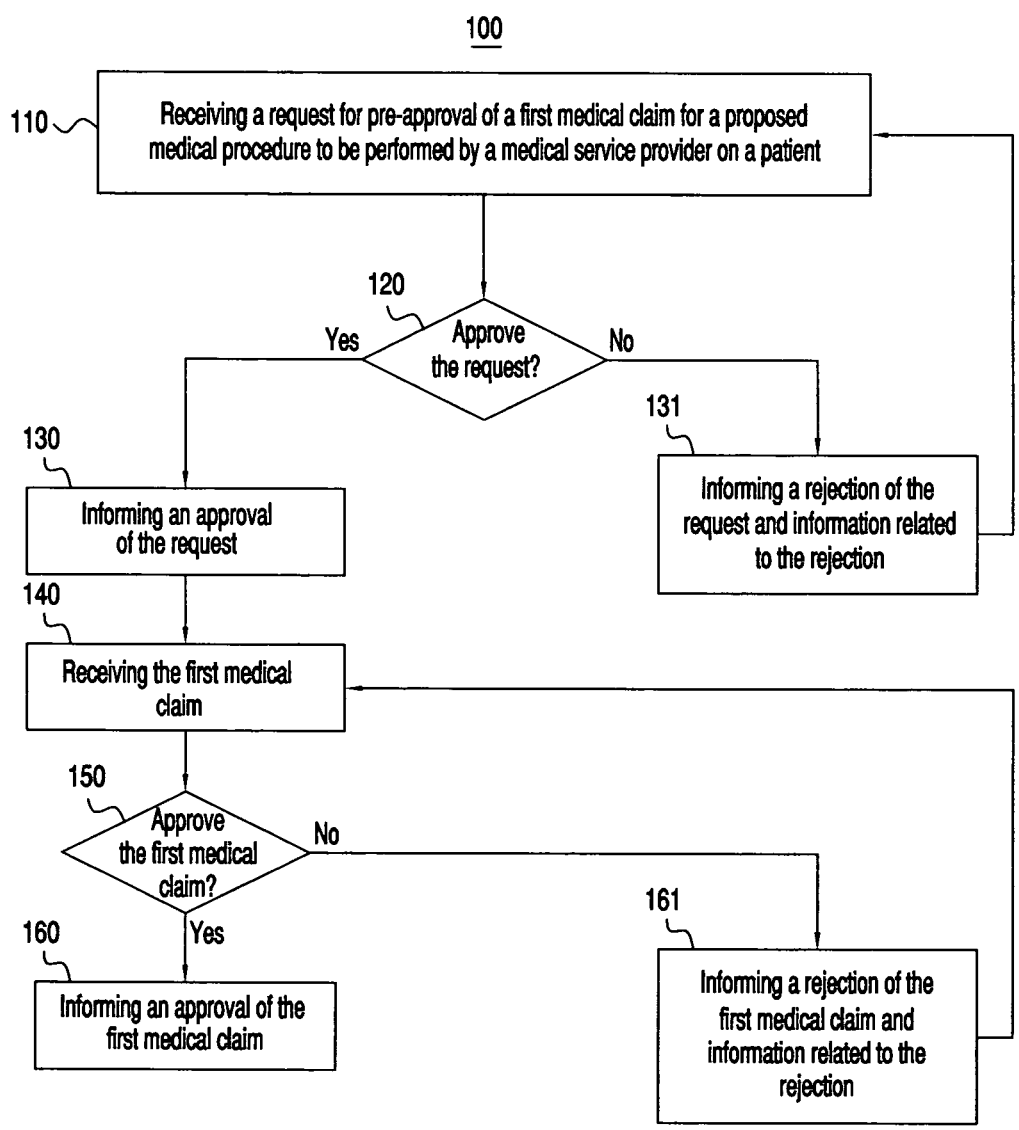
FIG. 1 illustrates a flow chart of a method for the real-time processing of medical claims in accordance with an embodiment of the invention.

FIG. 1 illustrates a flow chart of a method 100 for the real-time processing of medical claims. The real-time aspects of method 100 can be accomplished by using the Internet, and this Internet-based process is described in more detail hereinafter. At a step 110 of method 100, a request for pre-approval of a medical claim for a proposed medical procedure or a request for pre-approval of a referral to a medical specialist is received electronically in real time. The medical procedure contained in the request of step 110 is to be performed by a medical service provider and is to be performed on a patient of the medical service provider. The request in step 110 may be received from, for example, the medical service provider or a claims transmittal service hired by the medical service provider. The request in step 110 can be received by a medical plan provider that offers a medical plan under which the patient is a member, or the request in step 110 can be received by a third party that serves as a claims processing clearinghouse or an intermediary between the medical service provider and the medical plan provider.

The term "medical plan provider" means, collectively or individually, a health insurance company, a public or private employer, any employees of the health insurance company or employer, or any other similar or related entity. The term "medical service provider" means, collectively or individually, a medical laboratory performing medical tests and evaluating medical samples, a hospital, a medical clinic, a primary care physician (PCP), a medical specialist such as, for example, a thoracic surgeon, a dermatologist, or a dentist, employees of the PCP, specialist, laboratory, hospital, or clinic, employees of the practice group to which the PCP or specialist belong, or any other similar or related entity. Typical employees include, but are not limited to, nurses, internship student doctors, resident doctors, filing clerks, office managers, and receptionists.

At a step 120 of method 100, a decision is made electronically in real time as to whether the request for pre-approval of the medical claim should be approved. The decision process of step 120 is described in more detail hereinafter.

If the request is declined, denied, or rejected in step 120, the rejection is transmitted or informed electronically in real time at a step 131. Preferably, the rejection is transmitted to the sender of the request. However, if the sender of the request is not the medical service provider, but is, for example, a medical claims transmittal service, then the rejection is also sent to the medical service provider. The transmittal of the rejection preferably also includes, for example, information related to the rejection and/or an explanation of why the rejection occurred to enable an alteration of the request and a re-submission of the request such that the request may be approved upon its re-submission. Accordingly, after step 131, a portion of method 100 is repeated, beginning at step 110. The real-time transmittal of the rejection and its accompanying information or explanation provides an interactive claims processing method and eliminates the problems associated with the time lag created by traditional notification techniques. Without this real-time method, this rejection and re-submission process can take over three weeks, but using this real-time method, the delay can be less than three to five minutes.

If the request is approved in step 120, then the approval is transmitted or informed electronically in real time at a step 130. Similar to the notification of a rejection, the approval is preferably transmitted to the sender of the request, but if the sender is not the medical service provider, then the approval is also sent to the medical service provider. After the medical service provider receives an approval of the request, the medical service provider performs the proposed medical procedure on the patient. After the medical procedure is completed, the medical claim that was pre-approved is sent or submitted electronically.

At a step 140, the medical claim is received electronically in real time. In the preferred embodiment, the medical claim is received from the medical service provider. The medical claim can be received by a medical plan provider that offers a medical plan under which the patient is a member, or the medical claim can be received by a third party that serves as a claims processing clearinghouse or an intermediary between the medical service provider and the medical plan provider.

At a step 150 of method 100, a decision is made electronically in real time as to whether the medical claim should be approved. The decision process of step 150 is preferably similar to that of step 120 and is described in more detail hereinafter.

If the medical claim is declined, denied, or rejected in step 150, then the rejection is transmitted or informed electronically in real time at a step 161. Preferably, the rejection is transmitted to the sender of the medical claim. However, if the sender of the medical claim is not the medical service provider, but is, for example, a medical claims transmittal service, then the rejection is also sent to the medical service provider. The transmittal of the rejection preferably also includes, for example, information related to the rejection and/or an explanation of why the rejection occurred to enable an alteration of the medical claim and a re-submission of the medical claim such that the medical claim may be approved upon its re-submission. Accordingly, after step 161, a portion of method 100 is repeated, beginning at step 140. The real-time transmittal of the rejection and its accompanying information or explanation provides an interactive claims processing method and eliminates the problems associated with the time lag associated with traditional notification techniques. Without this real-time method, this rejection and re-submission process can take over three weeks, but using this real-time method, the delay can be less than three to five minutes.

If the medical claim is approved, the approval is transmitted or informed electronically in real time at a step 160. Similar to the notification of a rejection, the approval is preferably transmitted to the sender of the request, but if the sender is not the medical service provider, then the approval is also sent to the medical service provider.

In the preferred embodiment, method 100 is transaction-based and is not batch-based. The medical service provider sends each request or medical claim in real-time as the medical procedures are needed or completed. Therefore, if a patient walks in to a medical service provider's office, the medical service provider can immediately determine which medical procedures are covered and which are not covered. A delay of several weeks can be avoided by using method 100. The computer system receiving the request or medical claim processes each request and medical claim in real time upon receipt, and the computer system informs of the approval or rejection preferably before receiving and processing a different request or medical claim for the same medical service provider or for any other medical service provider.

In an alternative embodiment, method 100 is batch-based, but still operates in real-time. In this embodiment, upon receiving a batch of requests and/or medical claims, the computer system immediately processes the requests and/or medical claims and informs of the approval or rejection before receiving a different batch of requests and/or medical claims.

In another embodiment of method 100, the pre-approval process of steps 110, 120, 130, and 131 is skipped. This embodiment is useful when pre-approval for the medical procedure is not required. However, even if pre-approval is not required, steps 110, 120, 130, and 131 can still be performed to determine payment, credit, or reimbursement amounts, which are explained in more detail hereinafter. In still another embodiment of method 100, the medical claim approval process of steps 140, 150, 160, and 161 is skipped. This embodiment is useful when only a timely pre-approval process is necessary or desired.

Figure 2:
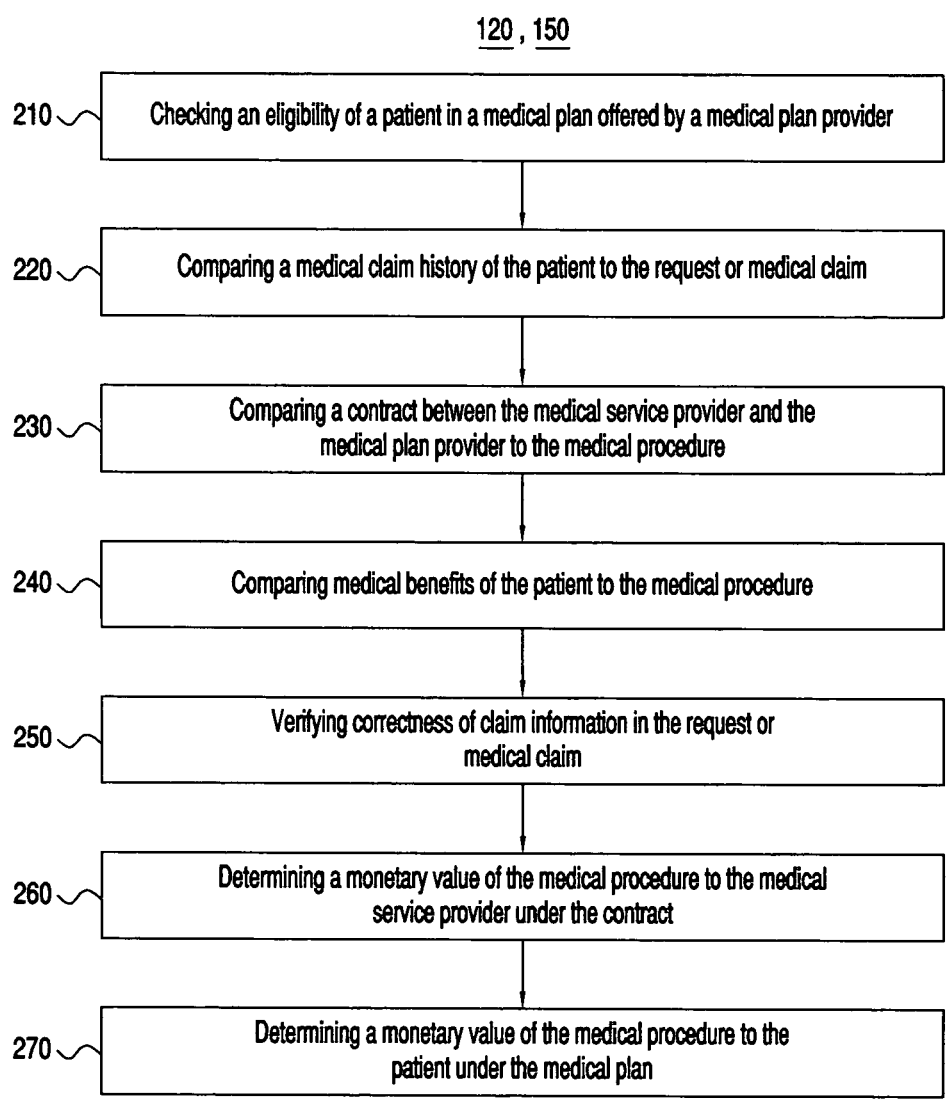
FIG. 2 illustrates a flow chart of a method for the real-time approval of medical claims and the real-time approval of requests for pre-approvals of medical claims, both of which are portions of the method in FIG. 1, in accordance with an embodiment of the invention.

FIG. 2 illustrates a flow chart of a method for the real-time approval of medical claims and the real-time approval of requests for pre-approvals of medical claims. The method in FIG. 2 provides more details of the approval process in steps 120 and 150 of FIG. 1. One skilled in the art will understand that the sequence of steps in the method of FIG. 2 is not fixed, but can be altered into any desired sequence. Furthermore, except for its use in FIG. 1, the term "medical claim" means a medical claim, a request for pre-approval of a medical claim, or both.

In a step 210 of FIG. 2, an eligibility of the patient for a medical plan offered by a medical plan provider is checked in real time. The medical claim is rejected if the patient is not a present member of a medical plan offered by the medical plan provider. In a step 220, the medical claim history of the patient is compared in real time to the medical claim. The medical claim is rejected if the medical claim is a duplicative claim. However, the medical claim might not be rejected if the medical claim is unique. A medical claim may be unique even if the medical procedure was performed previously on the same patient by the same medical service provider, as long as the same medical procedure was performed at a different time.

In a step 230, a medical contract between the medical service provider and the medical plan provider is compared in real time to the proposed or completed medical procedure. The medical claim is rejected if the terms of the contract do not cover the medical procedure. The terms "medical contract" or "contract" may include, for example, one of the following terms: (1) the medical plan provider pays a usual, customary, and reasonable fee for the medical procedure in a relevant geographic area to a medical service provider, (2) the medical plan provider pays a fixed percentage, such as eighty percent, of the usual, customary, and reasonable fees for the medical procedure in the relevant geographic area to a medical service provider, (3) the medical plan provider pays a fixed amount for the medical procedure to a medical service provider regardless of the relevant geographic area, or (4) the medical plan provider pays some predetermined schedule of fees to the medical service provider. Furthermore, one skilled in the art will understand that the "medical contract" or "contract" will comply with the Health Insurance Portability and Accountability Act of 1996 (HIPAA) of the United States Department of Health and Human Services (DHHS).

In a step 240, the medical benefits of the patient in the medical plan are compared in real time to the proposed or completed medical procedure. The medical claim is rejected if the medical benefits do not cover the medical procedure. In a step 250, the correctness or appropriateness of the medical claim is verified in real time. For example, if the medical claim indicates that the medical procedure is or was performed in the medical service provider's office, but the medical procedure should be or should have been performed in a hospital, then the medical claim is rejected. As another example, if a similar or more-encompassing medical procedure was listed in a previously paid medical claim, then the medical claim is rejected.

As an example, steps 230, 240, and 250 can be used to automatically detect in real time many problems associated with medical service providers who submit overlapping medical claims containing duplicative medical procedure codes. For example, assume that a surgeon has previously submitted a medical claim for an entire surgical plan, including pre-operation and post-operation procedures. The computer system performing methods 100 and 200 will detect if the surgeon submits a new medical claim for the same patient for a single post-operation procedure already covered by the previous medical claim. This type of duplicate medical claims submission is a common error correctable by using methods 100 and 200.

Part of the approval process in steps 120 and 150 in FIG. 1 may optionally include, for example, a determination of the monetary value of the proposed or completed medical procedure. For instance, in a step 260 of FIG. 2, a monetary value for the proposed or completed medical procedure to the medical service provider under the medical contract between the medical plan provider and the medical service provider is determined in real time. As an example, this monetary value may be an amount to be paid by the medical plan provider to the medical service provider, or this monetary value may be a credit to be applied to a monthly fixed payment already paid to the medical service provider by the medical plan provider. In a step 270 of FIG. 2, a monetary value for the proposed or completed medical procedure to the patient under the medical plan offered by the medical service provider is determined in real time. As an example, this monetary value may be an amount of insurance or medical coverage that the medical plan provides for the patient. This monetary value is subtracted from the medical service provider's bill to the patient to determine an amount that the patient owes the medical service provider. Factors that affect this monetary value include, but are not limited to, the patient's deductible under the medical plan and the doctor's non-preferred status under the medical plan.

One or both of steps 260 and 270 in FIG. 2 may optionally be intermediate steps between approving the request in step 120 of FIG. 1 and informing of the approval in step 130 of FIG. 1. Similarly, one or both of steps 260 and 270 in FIG. 2 may optionally be intermediate steps between approving the medical claim in step 150 of FIG. 1 and informing of the approval in step 160 of FIG. 1. However, regardless of the actual sequence of steps 260 and 270 of FIG. 2, steps 130 and 160 in FIG. 1 can optionally include, for example, informing in real time of the monetary values determined in steps 260 and 270. Furthermore, method 100 in FIG. 1 can also optionally include, for example, a step of electronically transferring the monetary value for the medical service provider from an account of the medical plan provider to an account of the medical service provider after step 160. This optional step, if used, preferably occurs within five days of receiving the medical claim in step 140 and can occur absent any manual intervention.

Figure 3:
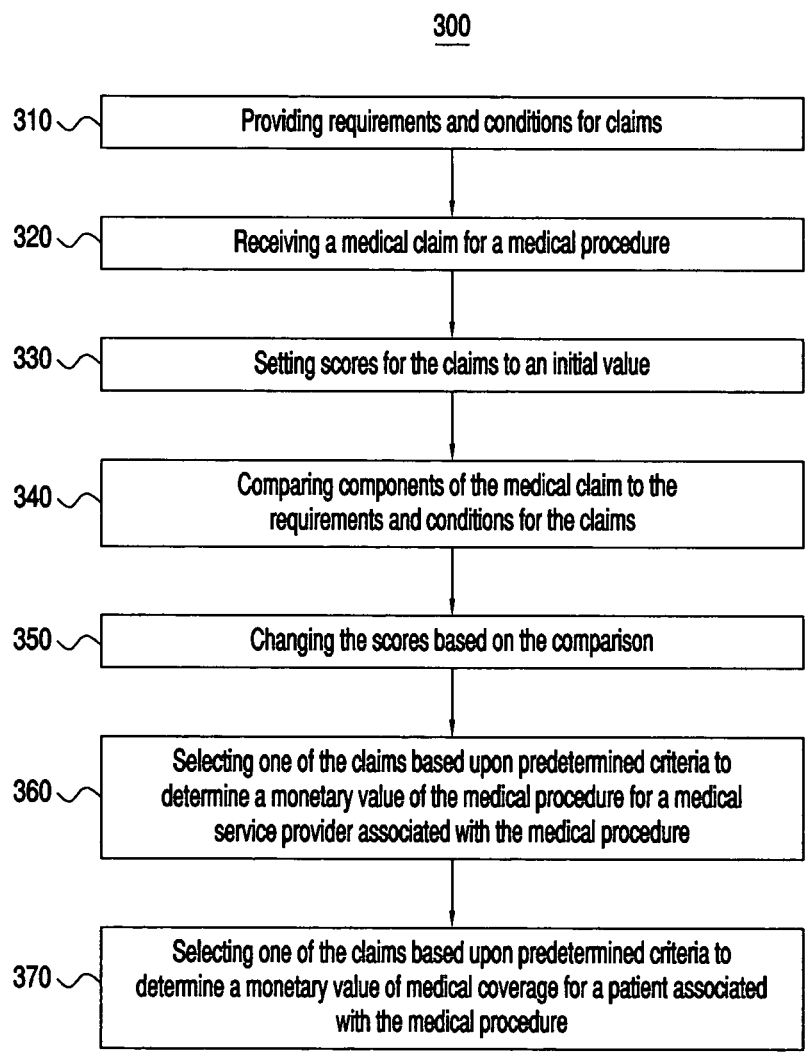
FIG. 3 illustrates a flow chart of a method for the real-time adjudication of medical claims, which is a portion of the method in FIG. 2, in accordance with an embodiment of the invention.

FIG. 3 illustrates a flow chart of a method 300 for the real-time adjudication of medical claims. The method of FIG. 3 provides more details of the monetary value determinations in steps 260 and 270 of FIG. 2, and the real-time aspects of the method in FIG. 3 are described in more detail hereinafter.

In a step 310 of FIG. 3, mandatory requirements and optional conditions for predetermined claims are provided. When evaluating a medical claim to determine a monetary value for a medical service provider, the requirements and/or conditions for the claim can include, for example, whether the medical procedure is for early periodic screening diagnostic testing of minors, whether and how much of the fee for the medical procedure is taken out of a risk pool of money, whether the dates of the medical procedure occur between the effective date and the termination date of the medical contract, whether a standard fee or a modified fee is used and the difference between these two types of fees, whether the patient falls within any applicable age restrictions, whether the fee for the medical procedure falls under a capitation schedule, whether there are any diagnosis restrictions, whether the location at which the medical procedure was performed is valid, whether the medical procedure could have been performed at a cheaper location and the difference in fees between the two locations, whether the medical procedure involved a medical service provider with a medical specialty, whether the medical claim must be reviewed manually, whether required documentation such as X-rays are included, and/or whether the medical procedure was a medical emergency.

When evaluating a medical claim to determine a monetary value of medical coverage for a patient, the requirements and/or conditions can include, for example, whether the location at which the medical procedure was performed is valid, whether the medical procedure could have been performed at a cheaper location and the difference in fees between the two locations, whether the dates of the medical procedure occur between the effective date and the termination date of the medical plan, whether the patient's medical plan has a rider and the terms of the rider, whether there are any diagnosis restrictions, whether there are any medical procedure restrictions, the gender of the patient, whether the medical procedure was performed by the patient's primary care physician or a different or affiliated medical service provider, whether the medical service provider is a preferred or non-preferred medical service provider under the medical plan, whether the medical procedure is performed by a specialist, whether the patient falls within any applicable age restrictions, whether the medical claim requires manual review, whether a standard fee or a modified fee is used and the difference between these two types of fees, whether required documentation is included, whether the medical procedure is an emergency, the dental area affected by the medical procedure, whether the medical procedure involved a prosthesis, and/or whether the medical procedure was pre-approved or pre-authorized.

As an example of step 310, a first set of requirements and a first set of conditions can be established for a first claim, and a second set of requirements and a second set of conditions can be established for a second claim where the second claim has a higher monetary value than the first claim. The higher monetary value can be for the patient, the medical service provider, or both. The requirements for the first and second claims can overlap with each other, and the conditions for the first and second claims can overlap with each other. Additionally, the requirements for the first claim can overlap the conditions of the second claim, and the requirements for the second claim can overlap the conditions of the first claim. The requirements and conditions for the first claim do not overlap each other, and the requirements and conditions for the second claim also do not overlap each other. While two claims are described for the explanation of the method in FIG. 3, one skilled in the art will understand that the computer system processing the method in FIG. 3 will use many hundreds or thousands of claims, each with their own unique set of requirements and conditions.

At a step 320, a medical claim for a medical procedure is received in real time. Next, at a step 330, scores for the first and second claims are set in real time to an initial value. The initial values for the first and second scores of the first and second claims, respectively, can be the same or different from each other. In the preferred embodiment, the initial values for the first and second claims are the same and are zero. Then, at a step 340, the components of the medical claim are compared in real time to the requirements and conditions of the first and second claims. At a step 350, the scores of the first and second claims are changed in real time based on the comparison of step 340. The score changing process of step 350 is explained in more detail hereinafter. The score changing of step 350 can occur after the component comparison of step 340 is entirely completed, but in the preferred embodiment, the score changing of step 350 is performed, as necessary, after each component is compared in step 340 and before comparing the next component such that steps 340 and 350 are repeated several times.

Then, at a step 360, the first or second claim is selected in real time based upon predetermined criteria applied to their respective scores to determine a monetary value of the medical procedure for a medical service provider associated with the medical procedure. Next, at a step 370, the first or second claim is selected in real time based upon predetermined criteria applied to their respective scores to determine a monetary value of medical coverage for a patient associated with the medical procedure. The sequence of steps 360 and 370 can be reversed, and the details of the predetermined criteria of steps 360 and 370 are explained hereinafter.

One skilled in the art will understand that the method of FIG. 3 is a portion or subset of method 100 in FIG. 1. For example, step 320 in FIG. 3 can be the same as steps 110 or 140 in FIG. 1, and steps 310, 330, 340, 350, 360, and 370 in FIG. 3 can be details or sub-steps of steps 260 and 270 in FIG. 2. Additionally, steps 330, 340, 350, 360, and 370 can be performed between steps 120 and 130 in FIG. 1 and between steps 150 and 160 in FIG. 1. The method in FIG. 3 is similar to method 100 in FIG. 1 in that the method in FIG. 3 is preferably transaction-based and is preferably not batch-based. In other words, after performing step 320 for a particular medical claim, steps 330, 340, 350, 360, and 370 are performed preferably before performing step 320 for a different medical claim. However, the method in FIG. 3 may alternatively be batch-based.

Figure 4:
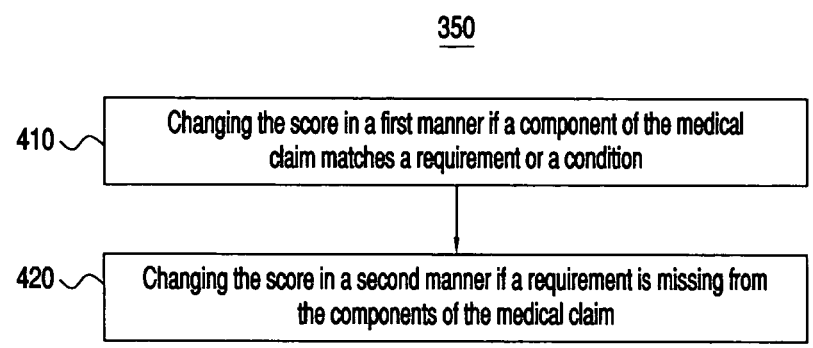
FIG. 4 illustrates a flow chart of a method for the real-time scoring of medical claims, which is a portion of the method of FIG. 3, in accordance with an embodiment of the invention.

FIG. 4 illustrates a flow chart of a method for the real-time scoring of medical claims. The method in FIG. 4 provides more details of the scoring process in step 350 of FIG. 3. In FIG. 4, at a step 410, the scores of the first and second claims are changed or adjusted in real time and in a first manner if a component of the medical claim matches a requirement or condition of the first or second claims. As an example, changing the score in the first manner can include, for example, changing the score in a first direction. In the preferred embodiment, the first direction is positive. For instance, a first value can be added to the score of the first claim for each of the components of the medical claim that match one of a first portion of the requirements of the first claim, and a second value can be added to the score of the first claim for each of the components of the medical claim that match one of a second portion of the requirements of the first claim. Similarly, a first value can be added to the score of the second claim for each of the components of the medical claim that match one of a first portion of the requirements of the second claim, and a second value can be added to the score of the second claim for each of the components of the medical claim that match one of a second portion of the requirements of the second claim. The values to be added to the scores of the first and second claims can be different from each other, but are preferably the same positive number, and the second values to be added to the scores of the first and second claims are also preferably the same positive number. As an example, both of the first values can be one, and both of the second values can be one hundred. However, both the first and second values can be negative numbers that are added or subtracted from the first and second scores, or only one of the first or second values can be negative.

Additionally, predetermined values can be added to the first and second scores for each one of the components in the medical claim that match one of a first or second portion of the conditions in the first and second claims. The predetermined values to be added to the scores of the first and second claims can be the same or different, and the predetermined values can be the same or different from the first and second values. As an example, the predetermined value can be zero for both the first and second claims.

At a step 420 in FIG. 4, the scores of the first and second claims are changed or adjusted in real time and in a second manner different from that of the first manner if a requirement of the first or second claims is missing from the components of the medical claim. As an example, changing the score in the second manner can include, for example, changing the score in a second direction. In the preferred embodiment, the second direction is negative. As an example, a first value can be subtracted from the score of the first claim for each requirement in a first portion of the requirements of the first claim that is missing from the components of the medical claim, and a second value can be subtracted from the score of the first claim for each requirement in a second portion of the requirements of the first claim that is missing from the components of the medical claim. Similarly, a first value can be subtracted from the score of the second claim for each requirement in a first portion of the requirements of the second claim that is missing from the components of the medical claim, and a second value can be subtracted from the score of the second claim for each requirement in a second portion of the requirements of the second claim that is missing from the components of the medical claim. The first values to be subtracted from the scores of the first and second claims can be different from each other, but are preferably the same. Similarly, the second values to be subtracted from the scores of the first and second claims are also preferably the same. Preferably, the first and second values in step 420 are the same as the first and second values, respectively, in step 410.

One skilled in the art will also understand that the sequence of steps 410 and 420 can be reversed and that steps 410 and 420 can be repeated for each component in the medical claim and for each requirement in the first and second claims. In a different embodiment of steps 410 and 420, a large positive value such as, for example, one thousand can be added to the score in step 410, and a small positive value such as, for example, one can be added to the score in step 420. In another embodiment of steps 410 and 420, a large negative value such as, for example, negative one thousand can be added to the score in step 410, and a small negative value such as, for example, negative one can be added to the score in step 420.

Figure 5:
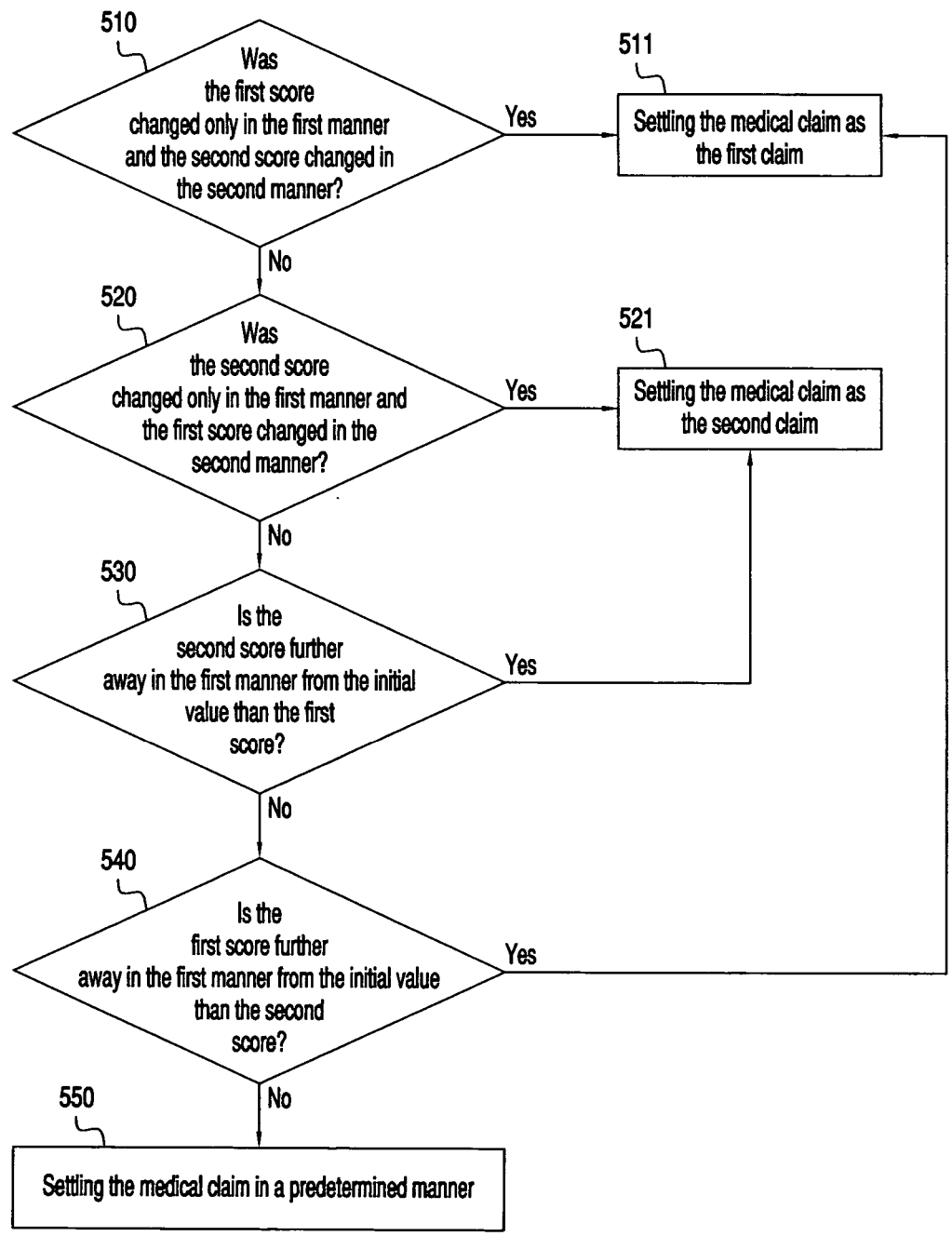
FIG. 5 illustrates a flow chart of a method for the real-time settlement of medical claims, which is a portion of the method of FIG. 3, in accordance with an embodiment of the invention

FIG. 5 illustrates a flow chart of a method for the real-time settlement of medical claims. The method in FIG. 5 provides more details of the selection process in steps 360 and 370 of FIG. 3, and the real-time aspects of the method in FIG. 5 are explained in more detail hereinafter. At a step 510 in FIG. 5, a determination is made in real time as to whether the score for the first claim was changed only in the first manner or direction and whether the score for the second claim was changed at all in the second manner or direction. If the answer to the question in step 510 is yes, then at a step 511, the medical claim is settled in real time under the terms defined in the first claim. However, if the answer to the question in step 510 is no, then at a step 520, a determination is made in real time as to whether the score for the second claim was changed only in the first manner or direction and whether the score for the first claim was changed at all in the second manner or direction.

If the answer to the question in step 520 is yes, then at a step 521, the medical claim is settled in real time under the terms defined in the second claim. However, if the answer to the question in step 520 is no, then at a step 530, a determination is made in real time as to whether the second score is further away in the first manner or direction from the initial value than the first score. If step 530 is performed, then both the first and second scores were changed only in the first manner or direction, or both the first and second scores were changed at least once in the second manner or direction. If the answer to the question in step 530 is yes, then step 521 is performed to settle the medical claim under the terms defined in the second claim. However, if the answer to the question in step 530 is no, then at a step 540, a determination is made in real time as to whether the first score is further away in the first manner or direction from the initial value than the second score. In the preferred embodiment where the initial value of the first and second scores is zero, the first and second scores may both be negative at steps 530 and 540. Under this condition, the score closest to zero is considered to be the score further away in the first manner or direction from the initial value.

If the answer to the question in step 540 is yes, then step 511 is performed to settle the medical claim under the terms defined in the first claim. However, if the answer to the question in step 540 is no, then the first and second scores have the same value and were either both changed only in the first manner or direction or both changed at least once in the second manner or direction. Accordingly, if the answer to the question in step 540 is no, then at a step 550, the medical claim is settled in real time in a predetermined manner, which is dependent upon whether is the medical claim is being adjudicated to determine a monetary value of the medical procedure for the medical service provider or for a patient. If the medical claim is being adjudicated to determine the monetary value for the medical service provider, then the predetermined manner settles the medical claim as the first or second claim having the lower monetary value. However, if the medical claim is being adjudicated to determine the monetary value for the patient, then the predetermined value settles the medical claim as the first or second claim having the higher monetary value.

One skilled in the art will understand that sequence of steps 510 and 520 can be reversed and that the sequence of steps 530 and 540 can also be reversed.

Figure 6:
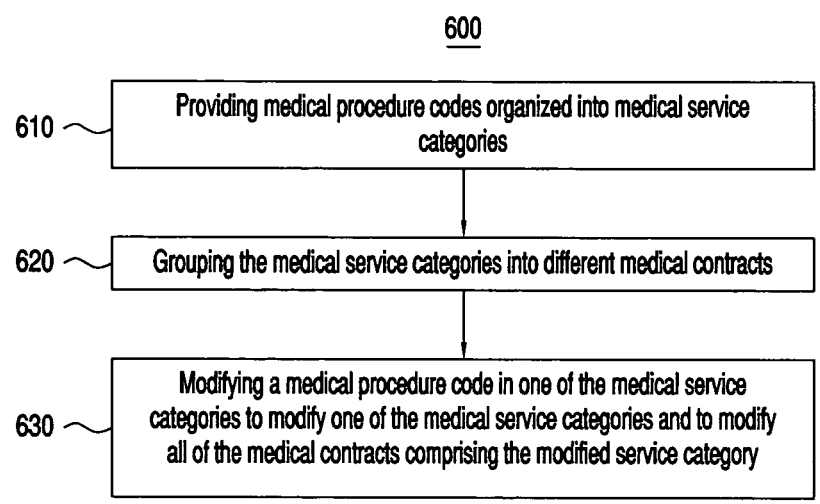
FIG. 6 illustrates a flow chart of a method for managing medical contracts between medical service providers and medical plan providers in accordance with an embodiment of the invention.

FIG. 6 illustrates a flow chart of a method 600 for managing medical contracts between medical service providers and medical plan providers. At a step 610, medical procedure codes are organized or arranged into medical service categories. Next, at a step 620, the medical service categories are grouped or arranged into medical contracts between the medical plan provider and different medical service providers. Then, at a step 630, a medical procedure code in one of the medical service categories is modified to modify one of the medical service categories and to automatically or inherently modify all of the medical contracts comprised of the modified medical service category.

As a specific example of method 600, assume that there are six medical procedure codes A, B, C, D, E, and F, that there are three medical service categories L, M, and N, and that there are two medical contracts Y and Z. Category L is comprised of codes A and B. Category M is comprised of codes C and D. Category N is comprised of codes E and F. Contract Y is comprised of categories L and M, and contract Z is comprised of categories M and N. By modifying code C in category M, category M is modified, and contracts Y and Z are also automatically or inherently modified. Additionally, if category L were also comprised of code C, then an additional modification of code C in category L will modify category L and will also automatically or inherently modify contract Y, but will not modify other categories or contracts.

Figure 7:
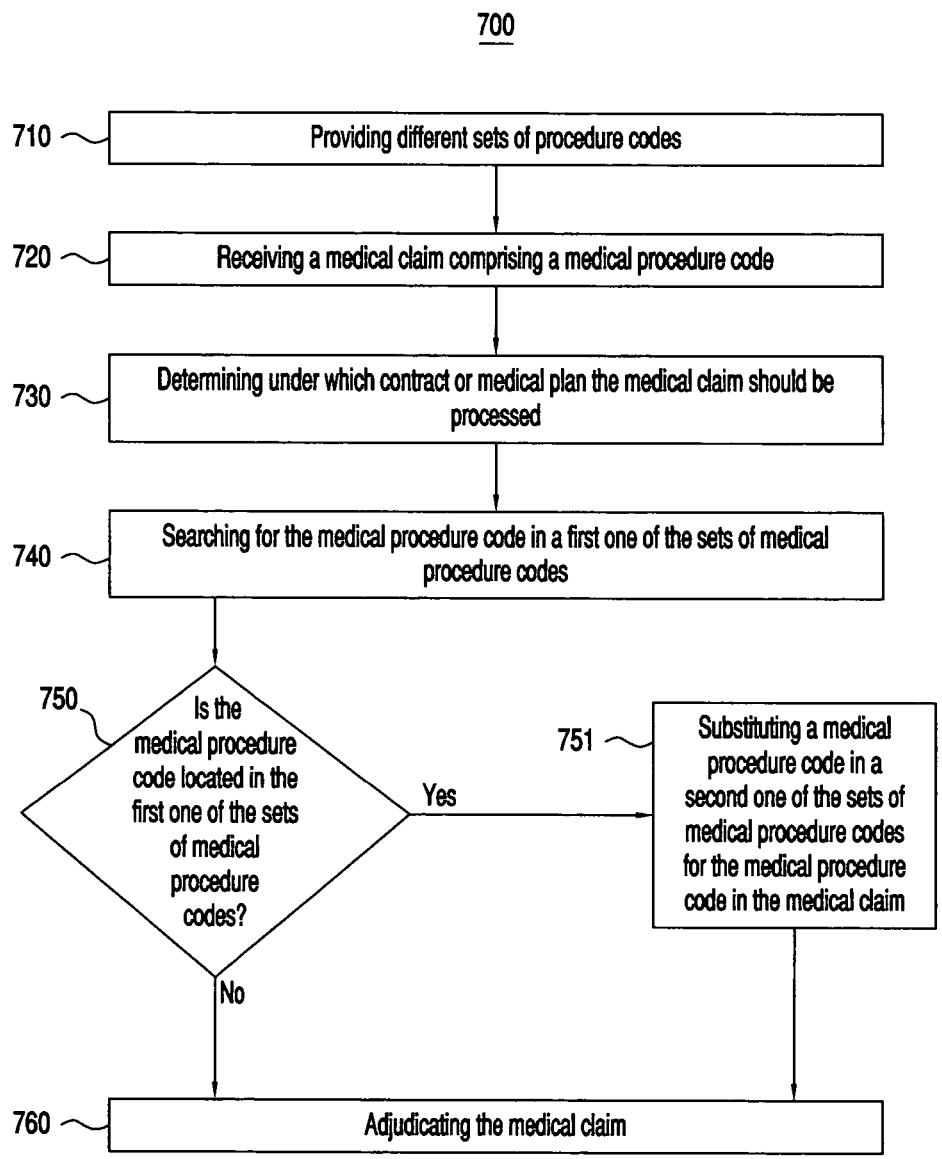
FIG. 7 illustrates a flow chart of a method for the real-time down-coding of medical claims, which is a portion of the method of FIG. 1, in accordance with an embodiment of the invention.

FIG. 7 illustrates a flow chart of a method 700 for the real-time down-coding of medical claims. The down-coding process is used when a particular medical procedure is not covered by a patient's medical plan or a medical service provider's medical contract, but when a similar medical procedure is covered. In this situation, the medical plan or the medical contract may permit a non-covered medical procedure to be substituted by a covered medical procedure when calculating monetary values for the patient and/or medical service provider. As an example of the usefulness of method 700, a medical contract or a medical plan may cover one type of tooth repair such as a porcelain filing, but not another type of tooth repair such as an amalgam filling. Therefore, if a medical claim is submitted with a medical procedure code indicating an amalgam filling, the system recognizes automatically that the amalgam filling is not covered, but that a porcelain filling is covered. The system substitutes automatically and in real time the medical procedure code for the amalgam filling with a medical procedure code for the porcelain filling. One skilled in the art will understand that none, some, or all of the medical procedure codes submitted with the medical may be down-coded. As used in the art, the term "down-coding" or "down-coded" means changing the code or re-coding and may include up-coding.

At a step 710, different sets of medical procedure codes linked or corresponding to each other are provided. As an example, a first set of codes can correspond to or can be linked with a second set of codes, and a third set of codes can correspond to or be linked with a fourth set of codes. The first and second sets of codes can be used for a first medical contract between a medical service provider and a medical plan provider or for a first medical plan between a patient and the medical plan provider, and the third and fourth sets of codes can be used for a second medical contract between the same or different medical service provider and the same or different medical plan provider or for a second medical plan between the same or different patient and the same or different medical plan provider. Each code in the first set corresponds to at least one code in the second set, and each code in the third set corresponds to at least one code in the fourth set. Furthermore, the codes in the first set are preferably absent from the second set, and the codes in the third set are preferably absent from the fourth set.

Next, at a step 720, a medical claim comprising at least one medical procedure code is received in real time. Then, at a step 730, a determination is made in real time as to under which medical contract or medical plan the received medical claim should be processed or adjudicated. If the medical claim is for the first medical contract or the first medical plan, then the subsequent steps, steps 740, 750, and 751, are performed using the first and second sets of medical procedure codes, but if the medical claim is for the second medical contract or the second medical plan, then the subsequent steps, steps 740, 750, and 751, are performed using the third and fourth sets of medical procedure codes. For purposes of illustration, steps 740, 750, and 751 are described as using the first and second sets of medical procedure codes.

At a step 740, a search is performed in real time to locate the medical procedure code in the medical claim in the first set of codes. At a step 750, a determination is made in real time as to whether the medical procedure code in the medical claim was located in the first set of codes. If the answer to the question in step 750 is no, then the medical procedure code is absent from the first set of codes, and at a step 760, the originally received medical claim with the original medical procedure code is adjudicated in real time. However, if the answer to the question in step 750 is yes, then at a step 751, the medical procedure code in the originally received medical claim is substituted in real time for the code or codes in the second set of codes that correspond with the matched or corresponding code in the first set of codes. After step 751, at step 760, the modified medical claim is adjudicated in real time with the corresponding code or codes from the second set of codes and preferably without the medical procedure code originally received with the medical claim. As an example, the details of the adjudication process in step 760 can be found in steps 330, 340, 350, 360, and 370 in FIG. 3.

One skilled in the art will understand that method 700 is a portion or subset of method 100 in FIG. 1 and the method in FIG. 3. For example, step 720 in FIG. 7 can be the same as steps 110 or 140 in FIG. 1 or step 320 in FIG. 3. Additionally, step 760 in FIG. 7 will not be performed if the medical claim is not approved in steps 120 or 150 of FIG. 1. Moreover, steps 720, 730, 740, and 750 in FIG. 7 can be performed, if needed, between steps 330 and 340 in FIG. 3. The real-time aspects of method 700 are described in more detail hereinafter. Method 700 is similar to method 100 in FIG. 1 in that method 700 is preferably transaction-based and is preferably not batch-based. However, method 700 may alternatively be batch-based.

FIGS. 8 through 22 are Entity Relationship Diagrams (ERDs), and the standard drawing and notation convention for ERDs is used in FIGS. 8 through 22. The ERDs represent a system comprised of a computer program used to execute the methods described earlier in FIGS. 1 through 7. Each numbered box in FIGS. 8 through 22 represents a menu or table activity and is divided into a top portion and a bottom portion. The top portion of each menu contains a unique system-generated identification (ID) of the menu, and the bottom portion of each menu contains at least one menu item associated with the unique ID. The ID of the menu typically includes the suffix "id." As an example, in FIG. 8, a "request" menu 806 has an ID of "requestid." If an ID or menu item is derived from another menu, then a parenthetical "FK," representing a "foreign key," is appended to the end of the ID or menu item, respectively. As an example, in FIG. 8, a "requestworkflow" menu 811 has an ID of "requestid(FK)" that is derived from "request" menu 806. Most of the names for the menu names, IDs, and menu items are self-explanatory to one skilled in the art. Some of the menus and some of the menu items are not shown in FIGS. 8 through 24 for simplicity.

A solid dot at the end of a line connecting two menus indicates that the menu contiguous with the solid dot is a child menu of the other menu, which is called a parent menu. A child menu has at least one ID or menu item derived from its associated parent menu. As an example, in FIG. 8, "request" menu 806 is a parent menu to "requestworkflow" menu 811, and "requestworkflow" menu 811 is a child menu to "request" menu 806. Some of the parent-child menu relationships are not illustrated in FIGS. 8 through 24 for simplicity.

A solid line from a parent menu to a child menu indicates an identifying relationship where the parent menu is part of a primary key for the child menu. Under these conditions, the parent menu defines at least one of the IDs in the child menu. As an example, in FIG. 8, "request" menu 806 and "requestworkflow" menu 811 are connected by a solid line. The "request" menu 806 has an ID of "requestid" that is one of the four IDs in the top portion "requestworkflow" menu 811.

A dashed line between parent and child menus indicates a non-identifying relationship where the parent menu's primary key is an attribute of the child menu and where the child menu may, therefore, contain a reference to the parent menu. Under these conditions, the parent menu defines at least one of the menu items in the child menu. As an example, in FIG. 8, a "requestsource" menu 810 is connected to "request" menu 806 by a dashed line. The "requestsource" menu 810 has an ID of "reqsource" that is a menu item in the bottom portion of "request" menu 806.

Figure 8:
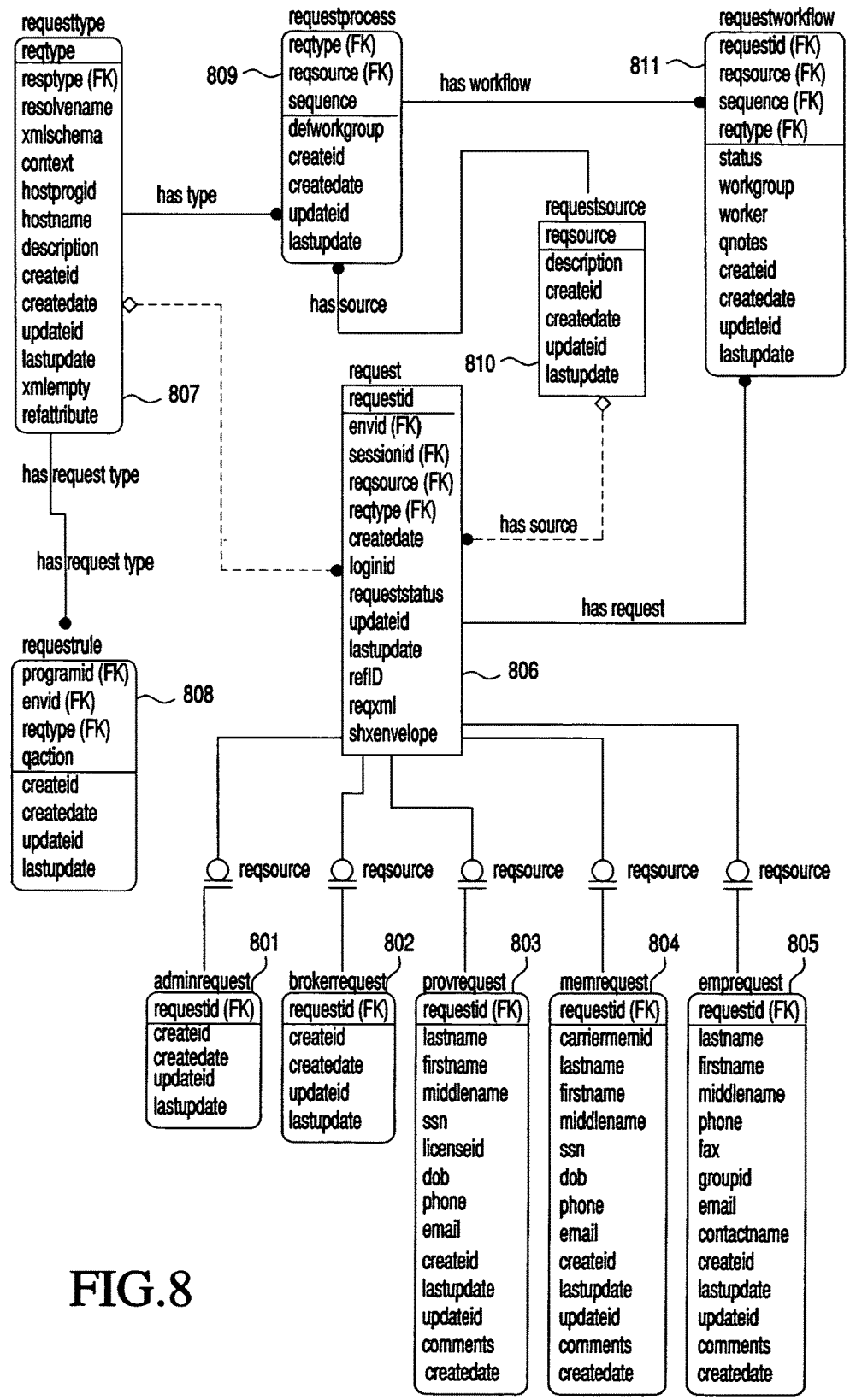
FIG. 8 illustrates an inter-relationship of menus for enrolling a new user of a system used to perform the methods described in FIGS. 1 through 7 in accordance with an embodiment of the invention.

FIG. 8 illustrates an inter-relationship of menus for enrolling a new user of the system used to perform the methods described in FIGS. 1 through 7 where the system is comprised of a computer program. Portions of the process for enrolling a new user may be performed manually to comply with the regulations of HIPAA.

The request for a new user account is submitted through a "requesttype" menu 807, and menu 807 is coupled or linked to a "requestrule" menu 808, a "requestprocess" menu 809, and a "request" menu 806. The terms "couple" and "link" mean a direct or indirect connection. Menu 808 provides the rules for the request and the processes to execute the request. The "requestprocess" menu 809 is accessed after satisfying the rules of the "requestrule" menu 808. The "request" menu 806 is coupled to menus 801, 802, 803, 804, and 805, which represent five different types of users that may access or use the system: a system administrator ("adminrequest"), a medical plan broker ("brokerrequest"), a medical service provider ("provrequest"), a member of a medical plan or a patient ("memrequest"), and an employer offering the medical plan or employing the member or patient ("emprequest"). A "requestsource" menu 810 and a "requestworkflow" menu 811 are both coupled to "requestprocess" menu 809 and "request" menu 806. "Requestworkflow" menu 811 represents an instance of "requestprocess" menu 809.

Most of the menu items in FIG. 8 are explained hereinafter, but only limited menu items in the subsequent figures are explained. Menus 801 through 805 include menu items for an identification of the person or system user who created the user account for the new user ("createid"), a creation date of the user account ("createdate"), an identification of the person or user who updated or modified the user account ("updateid"), and a date of the most recent or last update of the user account ("lastupdate"). Menus 803 through 805 also include the following information about the user of the new user account: a last name ("lastname"), a first name ("firstname"), a middle name ("middlename"), a telephone number ("phone"), an email address ("email"), and miscellaneous comments ("comments"). The "provrequest" menu 803 also includes menu items for the medical service provider's social security number ("ssn"), license ("licenseid"), and date of birth "(dob"). The "memrequest" menu 804 further includes menu items for the member's identification number within the medical plan ("carriermemid"), social security number ("ssn"), and date of birth ("dob"). The "emprequest" menu 805 additionally includes menu items for the employer's facsimile number ("fax"), group identification ("groupid"), and contact person ("contactname").

The "request" menu 806 includes menu items for an identification of the environment for the user ("envid"), an identification of the log-in session ("sessionid"), an identification of the source of the request ("reqsource"), a creation date for the new user account request ("createdate"), a log-in name or log-in identification of the user making the request ("loginid"), a status request to check if the request is still pending ("requeststatus"), an identification of the person who last updated the transaction ("updateid"), a date of the last update ("lastupdate"), a reference identification to the reference attribute in "requesttype" menu 807 to track any user who requested any information about any other user in the database ("refID"), the content or string of information in eXtendible Markup Language (XML) sent to the system across the Internet ("reqxml"), and a Secure Health Exchange envelope around the information in "reqxml" to ensure confidentiality of the information transmitted across the Internet ("shxenvelope").

The "requesttype" menu 807 includes menu items for a type of response to the request ("resptype"), a name for the component that will process the request ("resolvename"), an XML style sheet, web page layout, or schema ("xmlschema"), an identification of the host program used to access the system across the Internet ("hostprogid"), a name of the host computer server ("hostname"), a description of the request ("description"), an identification of the person who created the request ("createid"), a date of the request ("createdate"), an identification of the person who last updated the transaction ("updateid"), a date of the last update ("lastupdate"), a default XML style sheet ("xmlempty"), and reference attributes ("refattribute").

The "requestprocess" menu 809 includes a menu item for a default work group ("defworkgroup"), and the "requestworkflow" menu 811 includes menu items for the status of this instance of the process ("status"), the work group ("workgroup"), the worker ("worker"), and notes ("qnotes").

Figure 9:
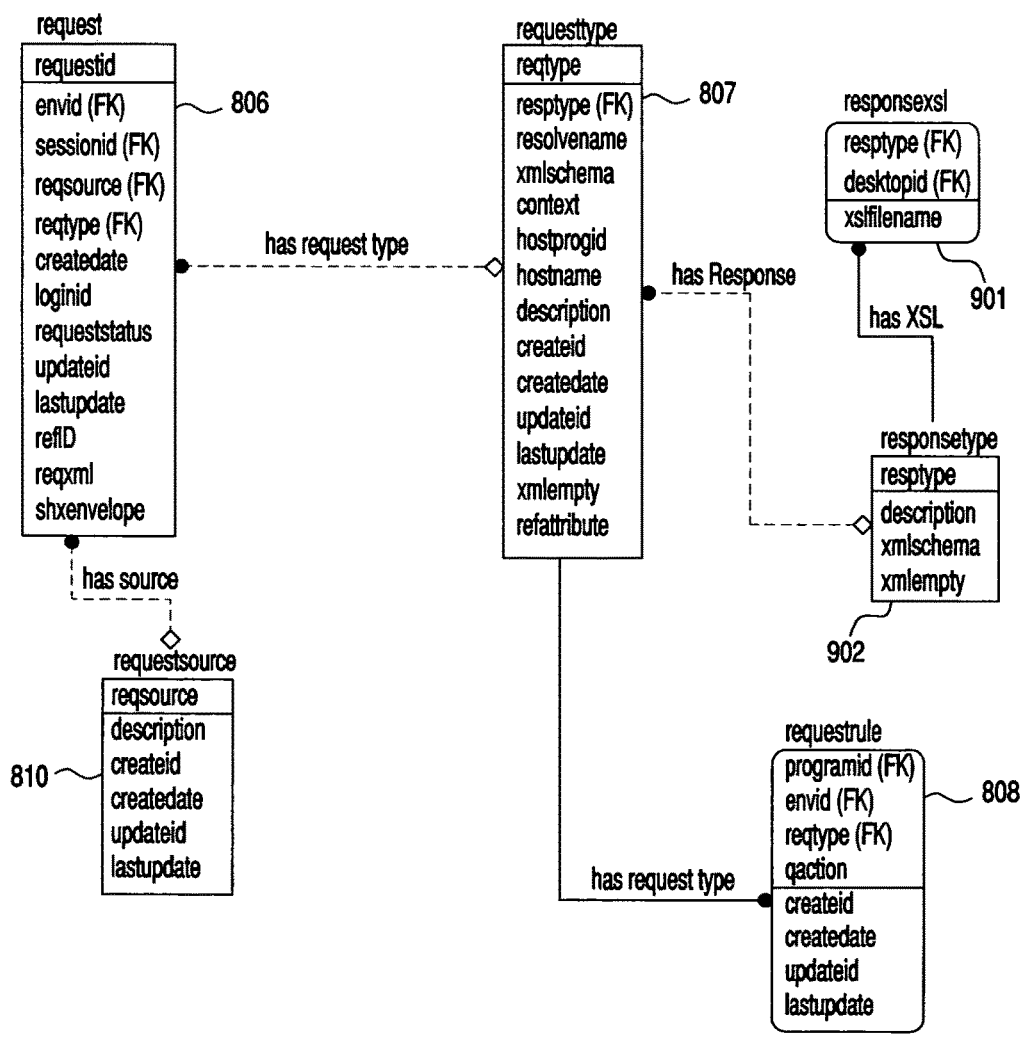
FIG. 9 illustrates an inter-relationship of menus for resolving a request made to the system in accordance with an embodiment of the invention.

FIG. 9 illustrates an inter-relationship of menus for resolving a request made to the system. A "responsexsl" menu 901 is linked to a "responsetype" menu 902, which is coupled to "requesttype" menu 807. The "responsexsl" menu 901 provides a style sheet for an XML schema, which represents the type of desktop or the view on the computer screen. The desktop can be dependent upon a role of the user to determine which requests are permissible and also to determine how to format the response to the request. The different types of roles can include, for example, a doctor, a medical plan member or patient, or an office receptionist. As an example, the office receptionist has more limited access privileges, may execute fewer requests, and receives less information from each executed request than the doctor or the patient.

Figure 10A:
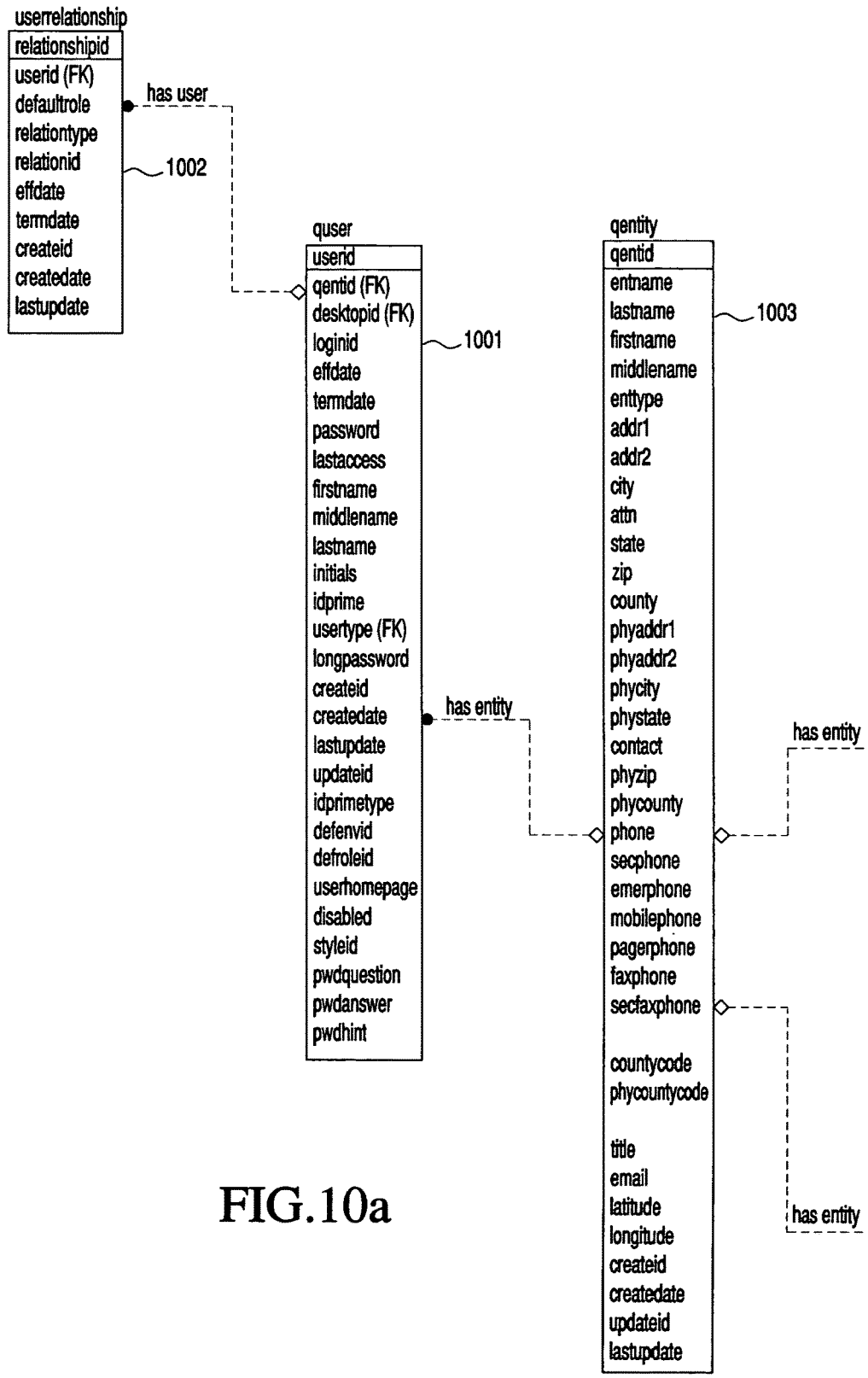
FIGS. 10a and 10b illustrate an inter-relationship of menus for tracking characteristics of a user of the system in accordance with an embodiment of the invention.
Figure 10B:
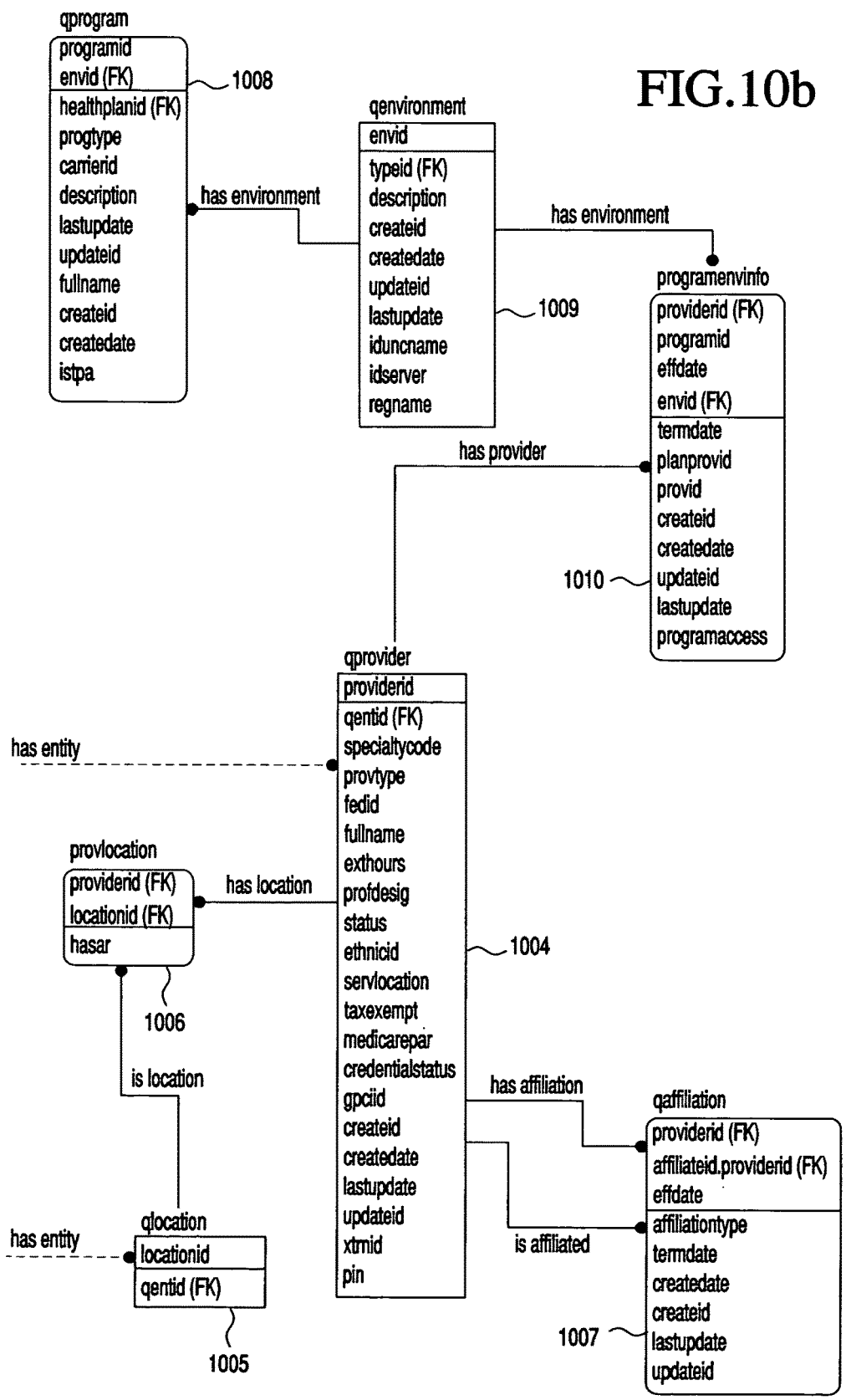

FIGS. 10a and 10b illustrate an inter-relationship of menus for tracking characteristics of a user in the system. FIGS. 10a and 10b are viewed horizontally adjacent to each other. A "quser" menu 1001 identifies a user of the system and has an ID of "userid," which is a unique system-generated source ID for each user. The "userid" and the other data associated with all of the menus are stored in a database in the system. The "quser" menu 1001 also has a menu item for indicating the user's account name ("loginid"). This "loginid" is unique for each user and is also stored in the database. The "quser" menu 1001 also includes menu items that indicate the effective date ("effdate") and the termination date ("termdate") for the "loginid." For example, if a doctor is leaving the medical contract in a month, the "termdate" can be programmed or entered into the database in advance of the termination date to automatically deactivate the doctor's "loginid" on the termination date.

The "quser" menu 1001 additionally includes a menu item for indicating a one-way encrypted password to allow only those users who know the "password" to use it to log into the system ("password"). The "password" is stored in the database in an encrypted manner and is also encrypted during the log-in process for further security. The "quser" menu 1001 also provides a menu item that tracks the date and time of the last log-in for the user ("lastaccess"). Another menu item on "quser" menu 1001 identifies a medical service provider, an employer, or a medical plan member to which the user is related or with which the user is associated ("idprime"). Still another menu item in "quser" menu 1001 specifies whether the "idprime" menu item identifies a medical service provider, an employer, or a medical plan member ("idprimetype").

The "disabled" menu item in "quser" menu 1001 overrides the "effdate" and "termdate" menu items. For example, if a specified "termdate" has not occurred, a user account may be disabled if there are more than a user-defined number of failed attempts to access the account. The "disabled" menu item therefore provides more security for the system. The "quser" menu 1001 also includes menu items for reminding the user of his/her password by asking a password question and providing a hint for the user's password if the password question is answered correctly ("pwdquestion," "pwdanswer," "pwdhint").

The "quser" menu 1001 is linked with a "userrelationship" menu 1002. If the user is a medical plan member or patient, then "userrelationship" menu 1002 can be used to identify relationships between the medical plan member and his/her dependents who are also covered under the member's medical plan. However, if the user is a medical service provider, then "userrelationship" menu 1002 can be used to identify relationships between the medical service provider and his/her staff. As indicated earlier, a user is assigned a role that determines the user's access privileges, and the relationship aspect can define a sub-user who has a subset of the user's access privileges. A "relationshiprole" menu (not shown in FIG. 10) can be linked to "userrelationship" menu 1002 to specify the role of the sub-user and the activities or requests that the sub-user can execute.

The "quser" menu 1001 is also coupled with a "qentity" menu 1003, which identifies the demographic information of the medical practice group or other business entity to which the medical service provider belongs. The "userid" ID in "quser" menu 1001 and the "qentid" ID in "qentity" menu 1003 may be the same ID when the user is a solo medical service provider. The "qentity" menu 1003 can also be used if the user is a medical plan member or patient.

The "qentity" menu 1003 and a "provlocation" menu 1006 are both linked to a "qprovider" menu 1004 and a "qlocation" menu 1005 for the various locations at which the medical service provider practices medicine. The "provlocation" menu 1006 includes a menu item for indicating whether that particular location has an accounts receivable function ("hasar"). A "qaffiliation" menu 1007 is coupled to "qprovider" menu 1004 to indicate the existence and type of any affiliation with another medical service provider, as indicated by menu item "affiliationtype" in menu 1007. For example, three primary care physicians (PCPs) who operate a single family practice clinic are affiliated with each other, and each of these PCPs will have all of the access rights to view, request, and edit information related to a patient of the other two PCPs. The "qprovider" menu 1004 includes a menu item for indicating the medical service provider's medical specialty ("specialtycode"), professional designations such as medical doctor (MD), doctor of dentistry school (DDS), ophthalmology doctor (OD), or the like ("profdesig"), active or inactive status ("status"), Universal Provider Identification Number (UPIN) ("upin"), identification for Medicare reimbursement under the Regional Based Relative Value System (RBRVS) ("gpcid"), and a link to an external medical service provider file ("xtrnid"). The UPIN is a standard of the Health Insurance Portability and Accountability Act of 1996 (HIPAA) of the United States Department of Health and Human Services (DHHS).

A "qprogram" menu 1008 represents the different medical lines of business, programs, health plans, or medical plans that a medical service provider offers. A menu item "healthplanid" in menu 1008 identifies the particular medical line of business. Examples of different medical lines of business include, but are not limited to, Medicare, Medicaid, a commercial Health Maintenance Organization (HMO), and a commercial Preferred Provider Option (PPO). Menu 1008 also includes a menu item for indicating a third party administered program ("istpa"). The "qprogram" menu 1008 is linked with a "qenvironment" menu 1009 that is coupled to a "programenvinfo" menu 1010, and menu 1010 is linked to "qprovider" menu 1004. Menus 1009 and 1010 determine which programs are executable within the selected operating environment. The "qenvironment" menu 1009 has menu items that specify the type and description of environment that the user uses when logged-in to the system ("typeid" and "description"). The "qenvironment" menu 1009 also has a menu item for providing a link to a default website for the present environment ("iduncname"). Other menu items in "qenvironment" menu 1109 specify the actual database server and the registration name that may be used by the user in this environment ("idserver," "regname"). The "programenvinfo" menu 1010 includes a menu item for a termination date of the program, health plan, or medical plan for the medical service provider ("termdate"). As an example, when a PCP refers a patient to a specialist, the inter-relationship of menus 1008, 1009, and 1010 permits the PCP to access more of the patient's medical information than the specialist.

Figure 11:
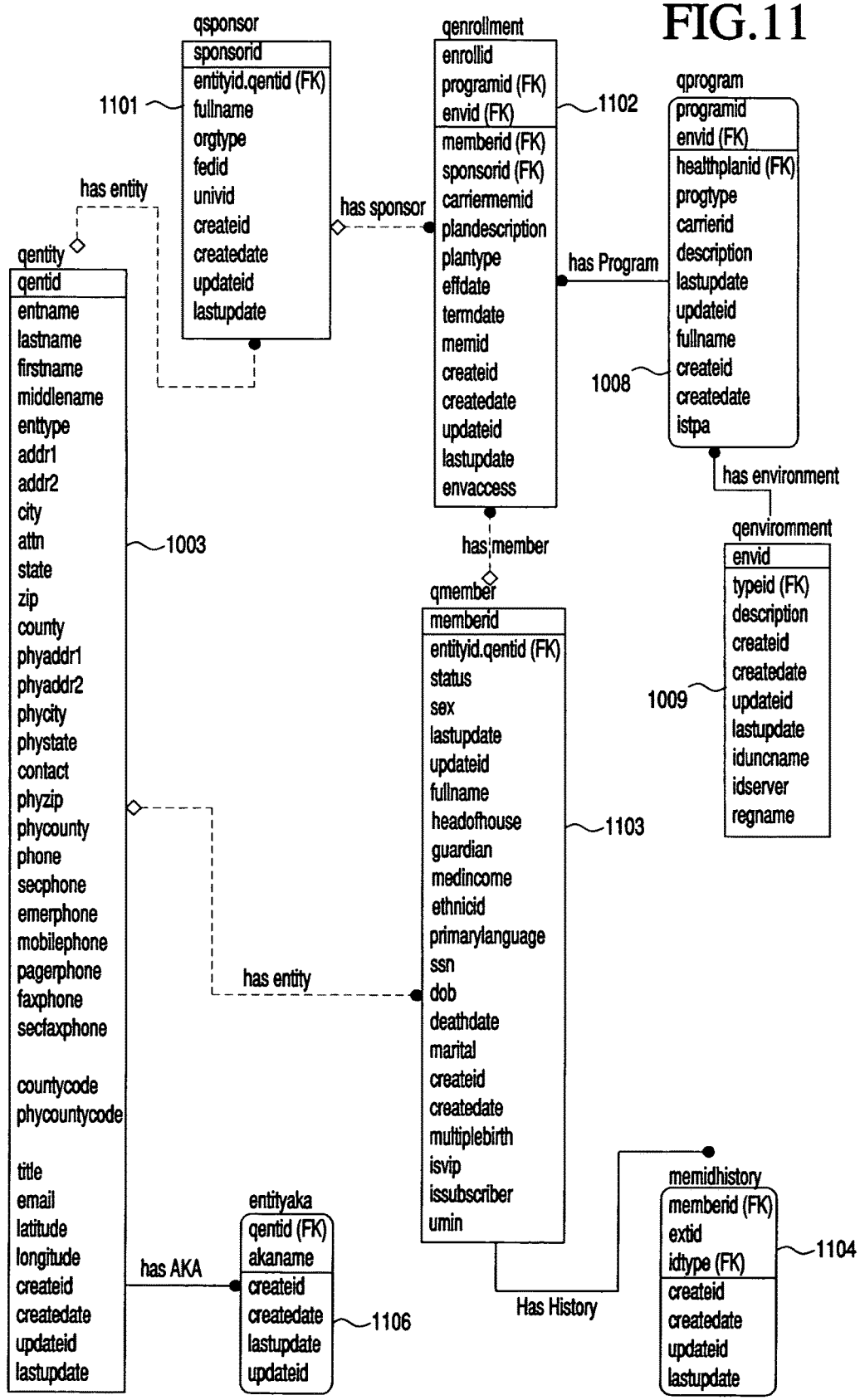
FIG. 11 illustrates an inter-relationship of menus for tracking members of an employer-sponsored medical plan in the system in accordance with an embodiment of the invention.

FIG. 11 illustrates an inter-relationship of menus for tracking members of an employer-sponsored medical plan in the system. A "qsponsor" menu 1101 represents the public or private employer offering the medical plan for its employees. Menu 1101 can alternatively represent any entity offering a medical plan. The "qsponsor" menu 1101 is coupled with "qentity" menu 1003 to reference the employer's information. An "entityaka" menu 1106 is linked with "qentity" menu 1003 to indicate any aliases or former names of the employer. One skilled in the art will understand that other versions of menu 1106 can be used to indicate any aliases or former names of medical plan members and/or medical service providers.

The "qsponsor" menu 1101 is also coupled to "qenrollment" menu 1102 to link medical plan members of a medical plan offered by the employer to the employer. The "qprogram" menu 1008 and the "qenvironment" menu 1009 are coupled to "qenrollment" menu 1102 to identify the characteristics of the medical plan. A "qmember" menu 1103 is also coupled to "qenrollment" menu 1102 to identify the employees of the employer who are members of the medical plan offered by the employer. The "qenrollment" menu 1102 permits any user to identify a member's or employee's medical plan, but the user cannot determine any other information about the member unless the user's access privileges specifically enable the user to do so. A "memidhistory" menu 1104 is coupled to "qmember" menu 1103 to indicate any past IDs of that member or employee under the medical plan.

Figure 12:
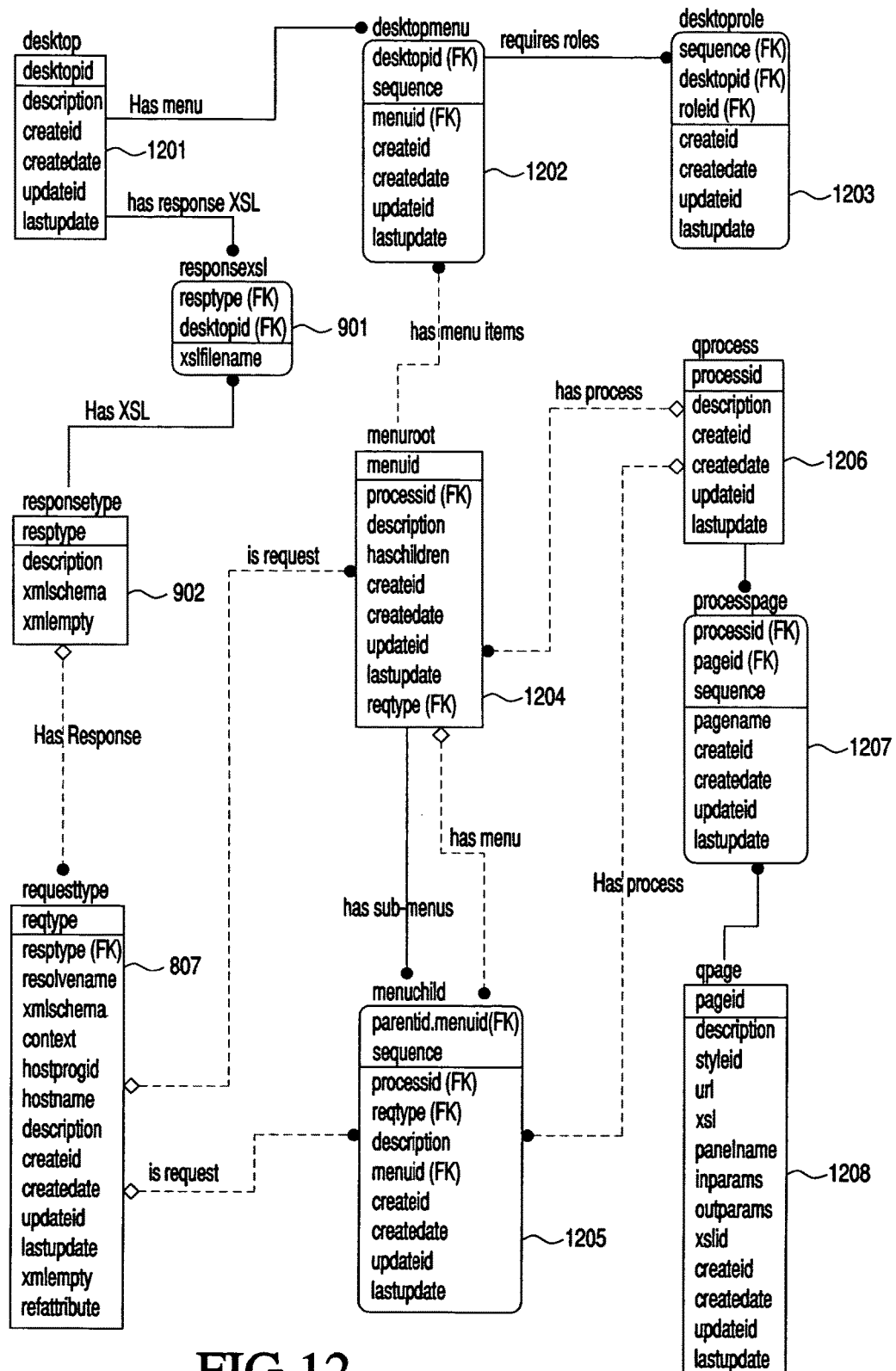
FIG. 12 illustrates an inter-relationship of menus for defining a desktop of a user of the system in accordance with an embodiment of the invention.

FIG. 12 illustrates an inter-relationship of menus for defining a desktop for a user of the system. The desktop can be for a primary care physician (PCP), an office manager of the PCP, a medical plan member, etc. A "desktop" menu 1201 defines the desktop on the computer screen. The "responsexsl" menu 901, "responsetype" menu 902, and "requesttype" menu 807 are coupled to "desktop" menu 1201. A "desktopmenu" menu 1202 is also coupled to "desktop" menu 1201 to indicate the menu options on the desktop. A "desktoprole" menu 1203 is coupled to "desktopmenu" menu 1202 to define which menu options are available to the user based on the user's role. Therefore, as an example, the office manager of the PCP can use the same desktop as the PCP, but the office manager will not have access to some of the activities executable from the desktop.

A "menuroot" menu 1204 is also coupled to "desktopmenu" menu 1202 to indicate the root or main level menu on the desktop. A "menuchild" menu 1205 is coupled to "menuroot" menu 1204 to indicate any child menus or sub-menus extending from the root menu. The "menuchild" menu includes a "sequence" ID to indicate the sequence or order of the child menus extending from the root menu. The root and child menus can execute processes, as indicated by a "qprocess" menu 1206 coupled to "menuroot" menu 1204 and "menuchild" menu 1205 and as also indicated by a "processid" menu item in menus 1204 and 1205. The processes are displayed on web pages, as indicated by "processpage" menu 1207 and "qpage" menu 1208. Both of menus 1207 and 1208 are coupled to "qprocess" menu 1206. The processes assist the user in executing or submitting requests identified in "requesttype" menu 807. The root and child menus can also execute requests directly, as indicated by the dashed lines connecting "requesttype" menu 807 to "menuroot" menu 1204 and also to "menuchild" menu 1205.

The "qpage" menu 1208 includes a menu item to permit the style, format, or layout of the web page to be modified depending on the language used in the web page ("styleid"). For example, the web page layout may be originally designed for English text, but if Spanish text is to be used, some adjustments to the web page layout may be needed. Therefore, the same page can be used in different styles when changing from one language to another. When changing from one language to another, the data or information on the page does not change. The "qpage" menu 1208 includes a menu item to indicate a universal resource locator (URL) or an actual web address of a web site ("url"). The "qpage" menu 1208 further includes a menu item to indicate a default style sheet applied to the URL ("xsl"). The menu item "styleid" in "qpage" menu 1208 is a user-defined style sheet that overrides the default style sheet "xsl." The "qpage" menu 1208 additionally includes a menu item for describing a name of a panel within the web page ("panelname").

Figure 13:
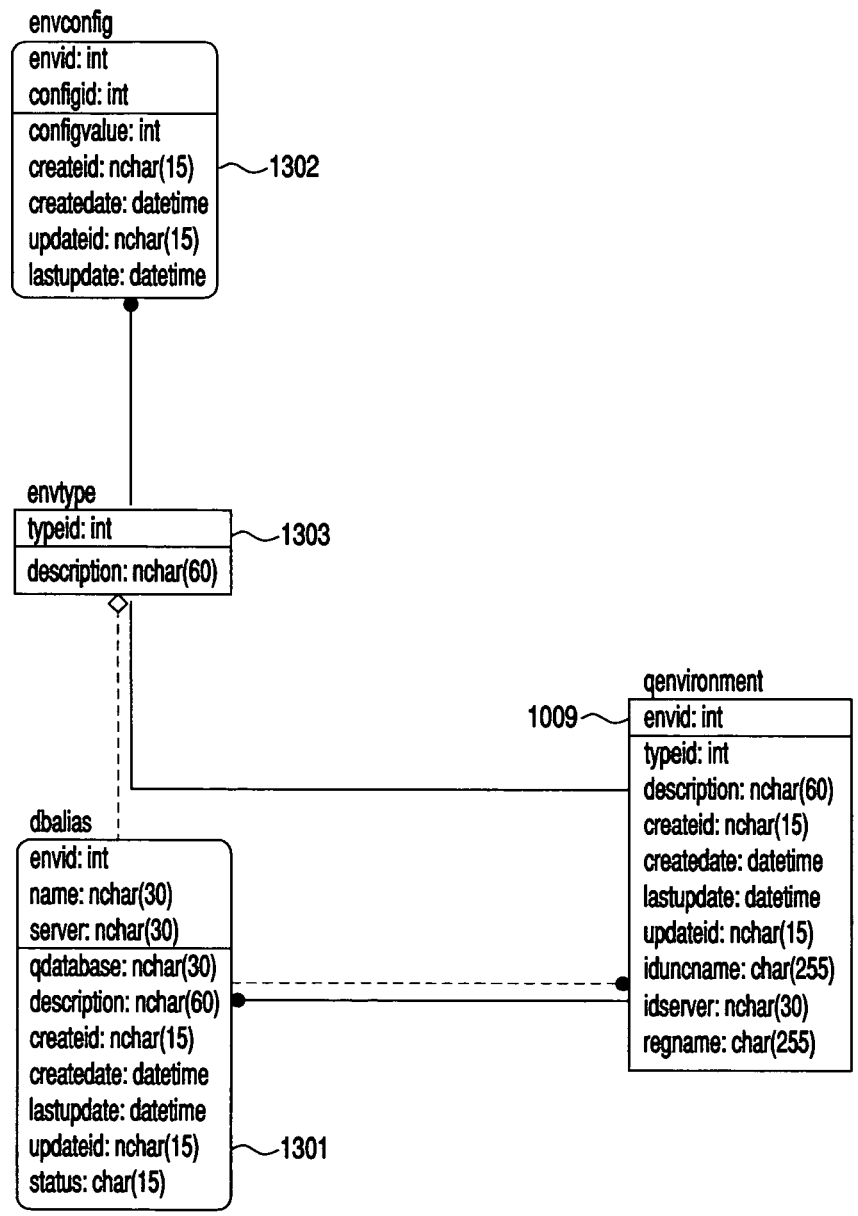
FIG. 13 illustrates an inter-relationship of menus for defining an environment within the system in accordance with an embodiment of the invention.

FIG. 13 illustrates an inter-relationship of menus for defining or managing an environment within the system. A "dbalias" menu 1301 permits a single medical plan to be used with different environments and different databases located on the same physical computer server. The "dbalias" menu 1301 has menu items defining the actual database name ("qdatabase"), a description of the database ("description"), an identification of the creator of the database ("createid"), a date of creation ("createdate"), a most recent date of modification ("lastupdate"), an identification of the person entering the most recent modification ("updateid"), and a status of the database ("status").

The "qenvironment" menu 1009 is linked to both "dbalias" menu 1301 and an "envtype" menu 1303, and menu 1303 links an "envconfig" menu 1302 to "dbalias" menu 1301 and "qenvironment" menu 1009. This configuration of menus establishes which databases are used with which environments. The "envconfig" menu 1302 defines environment configurations, including system-level-defined configurations and user-defined configurations. A configuration is an optional setting such as, for example, retroactive dis-enrollment of medical plan members. These environment configurations can be turned on or off. As another example, a configuration may determine a default user interface that a user in that environment sees on the desktop. Examples of such default interfaces include, but are not limited to, an interface for dental benefits only or an interface for a Health Maintenance Organization (HMO). The environment configurations may override any access privileges under the user's role. Therefore, in one environment, a particular user may be able to execute a request, but in a different environment, the same user may not be able to execute the request. The "envconfig" menu 1302 includes an environment ID ("envid") and a configuration ID ("configid") as internal numbers to the environment and configuration, respectively. The internal number for a particular configuration is consistent across all environments. The "envconfig" menu 1302 also includes menu items to provide an encrypted key ("configvalue"), to record who created the entry in the menu ("createid"), to record the date when the entry was created ("createdate"), and to identify the date and time the entry was created ("lastupdate").

Figure 14:
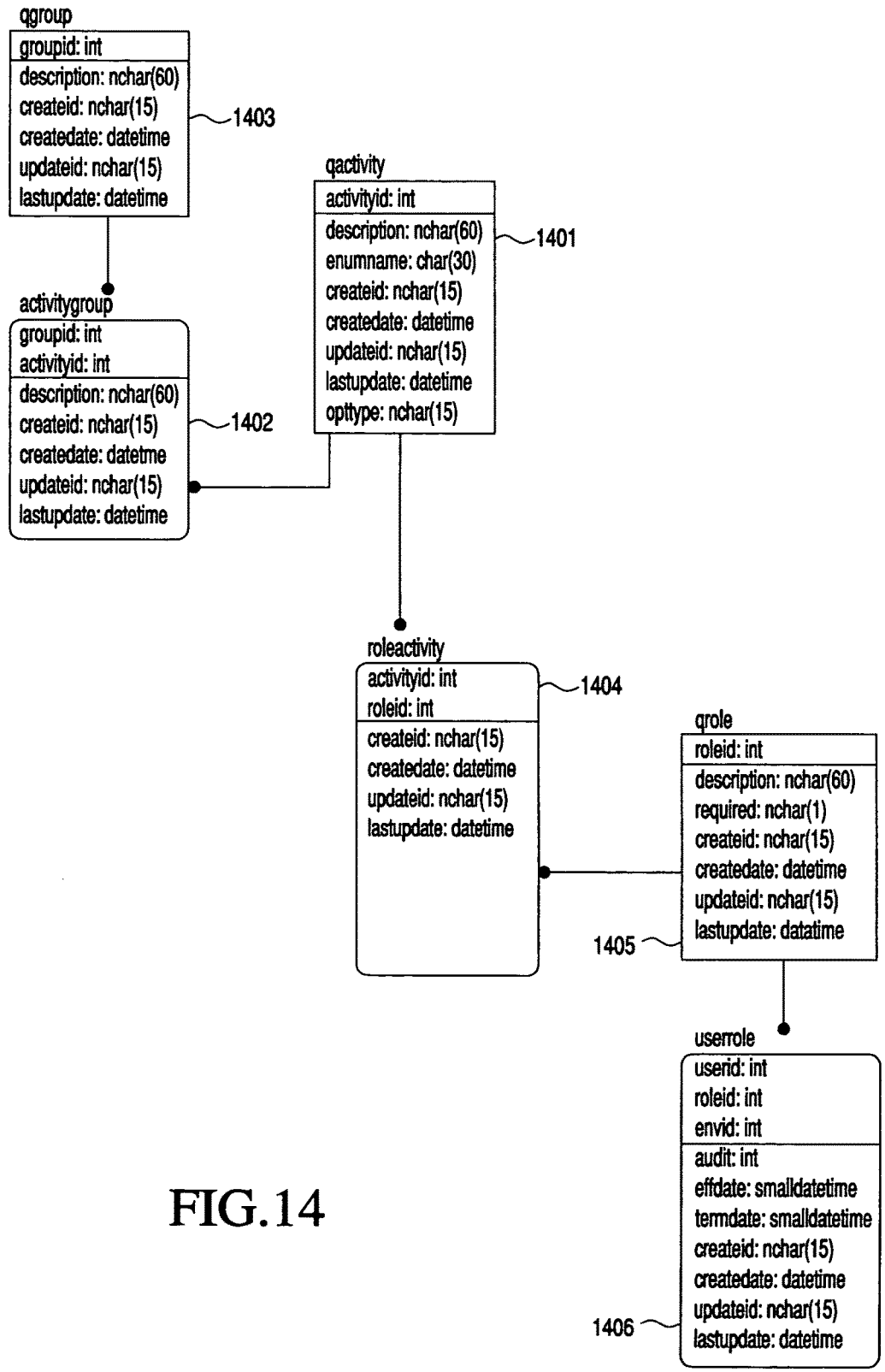
FIG. 14 illustrates an inter-relationship of menus for defining role-based security in the system in accordance with an embodiment of the invention.

FIG. 14 illustrates an inter-relationship of menus for grouping various activities into different roles to facilitate the management of user access privileges and to define role-based security in the system. In a "qgroup" menu 1403, a unique group of activities may be defined by the user. Menu 1403 includes a menu item for a numeric description of the group ("description"). As an example, a group of claim processing activities may be defined in menu 1403. All similar activities can be grouped together in this manner. The individual activities are attached to that group by an "activitygroup" menu 1402, which is linked to a "qgroup" menu 1403. The individual activities to be used in "activitygroup" menu 1402 are provided from a "qactivity" menu 1401, which is linked to menu 1402. Activities can include, for example, viewing demographics for all members of a medical plan or viewing medical claims for a particular member in a medical plan. The "qactivity" menu 1401 includes a menu item for numerically describing the activity ("description") and also includes a menu item for an alphanumeric enumeration name of the "description" to facilitate locating the activity ("enumname"). Another menu item in menu 1401 signifies whether the activity is optional or mandatory ("opttype").

A "roleactivity" menu 1404 is linked to "qactivity" menu 1401 and assigns certain activities to certain roles and defines all permissible activities or access privileges for a particular role. These permissible activities are individually and/or collectively linked to the role by using "qactivity" menu 1401 and/or "activitygroup" menu 1402. The system administrator can select groupings of activities from "activitygroup" menu 1402 to collectively assign activities to a role such as "user security." If "activitygroup" menu 1402 is selected, all of the grouped activities for that group will automatically be assigned to the role. This grouping process simplifies maintenance of the system. However, the system administrator may also assign individual activities to a role by selecting "qactivity" menu 1401.

A "qrole" menu 1405 is linked to menu 1404 and defines the roles that a user may have. The "qrole" menu 1405 includes menu items "description" and "required" to specify a description of the role and whether the role is a required role, respectively. A "userrole" menu 1406 is coupled to menu 1405 and links a particular role to a particular user. As an example, the user's role within the environment may be a plan administrator, a medical plan member, or a call channel worker who is taking calls and entering issues. A user may have more than one role in a particular environment. The "userrole" menu 1406 includes a menu item "audit," which is an audit flag indicating the need to audit user activity when this particular user role is being used by any user. The "userrole" menu 1406 also includes menu items for an effective date ("effdate") and a termination date ("termdate") for the role of a user.

When a user is performing any action, "roleactivity" menu 1404 determines if an activity to be executed by the user is assigned to at least one of the roles of the user. It does not matter which role has the activity so long as at least one of the roles in "userrole" menu 1406 that is assigned to the user has the activity in "roleactivity" menu 1404 that is required to complete the process. If none of the roles assigned to the user have the activity or activities needed to complete the process, then the system displays a security violation error message, and the user is not permitted to execute the activity or activities to complete the process.

Figure 15A:
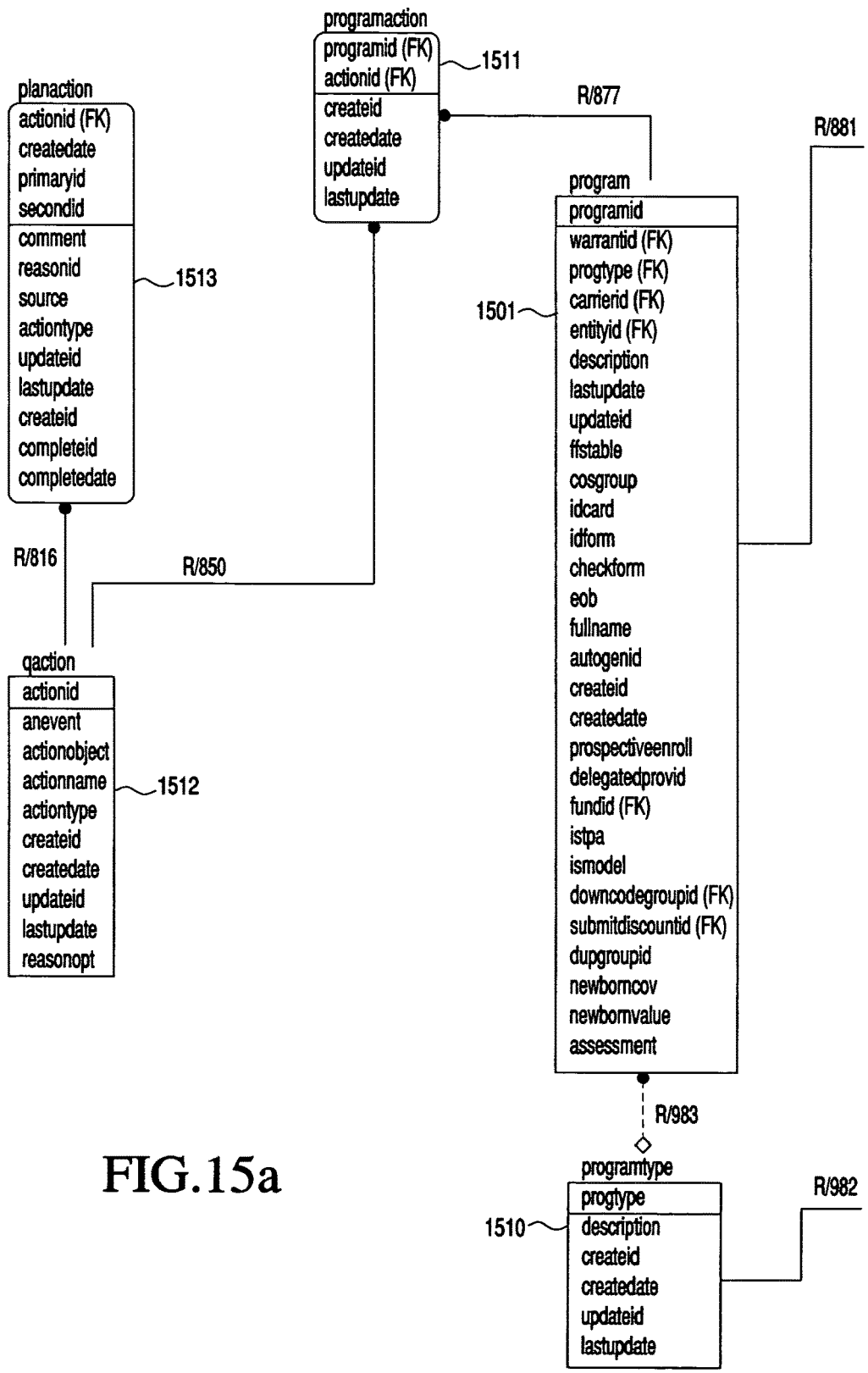
FIGS. 15a and 15b illustrate an inter-relationship of menus for defining different medical lines of business and associated rules in the system in accordance with an embodiment of the invention.
Figure 15B:
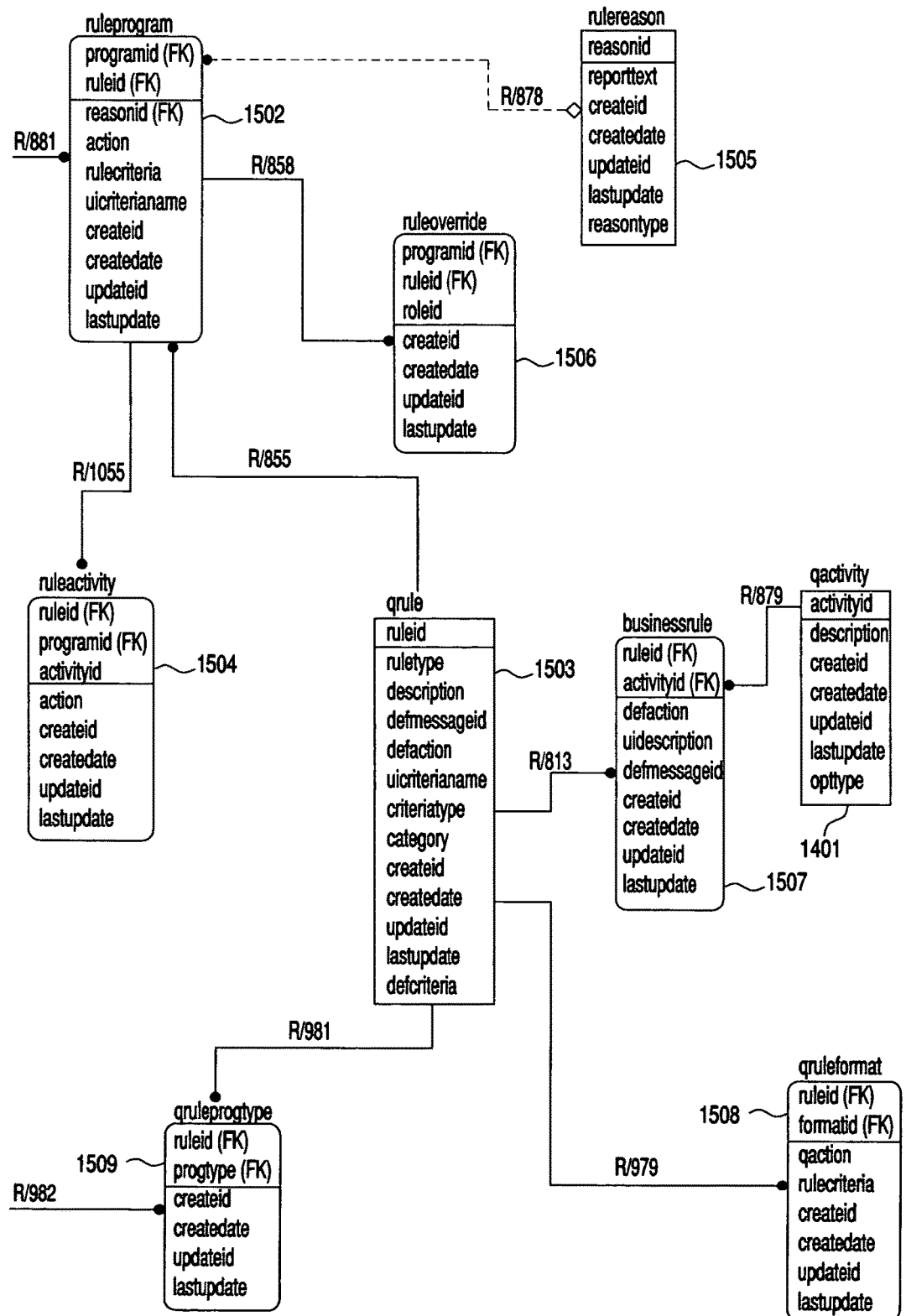

FIGS. 15a and 15b illustrate an inter-relationship of menus for defining or establishing different medical lines of business or different medical plans and associated rules in the system. FIGS. 15a and 15b are viewed horizontally adjacent to each other. Each member is enrolled in or is assigned to a medical plan or a program. A "program" menu 1501 establishes the rules for the medical plan and permits different rules for different programs within one system. A "programtype" menu 1510 is coupled to menu 1501 to identify the type of program. Examples of different types of programs that a medical plan provider may offer include, but are not limited to, a medical plan designed as an HMO, a medical plan designed specifically for dental benefits, or a medical plan designed specifically for senior citizens such as Medicare or Medicaid.

The "program" menu 1501 is linked to a "ruleprogram" menu 1502 implementing a particular set of rules for the program, and "ruleprogram" menu 1502 is linked to a "qrule" menu 1503 containing the definition of the rule ("description") and its default action ("defaction"). The "ruleprogram" menu 1502 filters out rules that are not applicable to the selected program, and an "action" menu item in menu 1502 identifies which action to perform if the rule or rules are satisfied. A "rulecriteria" menu item in menu 1502 stores any criteria for the rule such as, for example, a maximum of 90 days between the date of the medical procedure and the submission date of the medical claim. A "ruleactivity" menu 1504 is linked to menu 1502 and refines how a rule is enacted based on the different actions. A "rulereason" menu 1505 is also linked to menu 1502 and provides information or reasons for the application of the rule. The information or reasons can be included in, for example, remittance printouts or on-line information. A "ruleoverride" menu 1506 is also linked to menu 1502 and identifies which user roles can override which rules. Therefore, even though the system may deny or reject a medical claim, a user may be able to override the rejection and permit payment of the claim.

A "businessrule" menu 1507 is linked to "qrule" menu 1503 and provides a template of the rule activities. The "ruleactivity" menu 1504 applies specific rules to specific activities, and "businessrule" menu 1507 defines the rules applicable to the activities. Thus, "businessrule" menu 1507 acts as a template. A rule in "ruleactivity" menu 1504 can not be accessed for a given activity unless a rule-activity combination exists in "businessrule" menu 1507. The "qactivity" menu 1401 described in conjunction with FIG. 14 is coupled to "businessrule" menu 1507 in FIG. 5. A "qruleformat" menu 1508 is also coupled to "qrule" menu 1503 and defines which rule formats can apply a rule. Menu 1508 permits, for example, a rule to be created for a particular type of electronic data exchange (EDI) transaction. A "qruleprogtype" menu 1509 is linked to both "qrule" menu 1503 and "programtype" menu 1510 to provide different rule templates for different types of programs and to filter out rules that have no applicability to a program.

After a specific rule or a specific set of rules for the program is satisfied, then the program executes certain actions associated with those rules. These actions are "soft" and are performed by "program" menu 1501. An action can include, but is not limited to, enrolling a member, generating an identification card for the member after enrollment, terminating a member, or generating a Consolidated Omni-Bus Reconciliation Act (COBRA) letter for the member after terminating the member. A "programaction" menu 1511 is linked to "program" menu 1501; a "action" menu 1512 is coupled to menu 1511, and a "planaction" menu 1513 is linked to menu 1512. The "programaction" menu 1511 links an action from "qaction" menu 1512 to a medical line of business or a program. The "qaction" menu 1512 includes an "actionobject" menu item indicating the business objective for performing the action. A specific event can be defined in the "actionobject" menu item of menu 1512, and when the event occurs, the action is initiated. The "planaction" menu 1513 creates and stores a record that tracks the action and the date and time that the action occurred. A "primaryid" ID and a "secondaryid" ID in menu 1513 track the member and the enrollment when a new enrollment is added so that new member letters and primary care physician notifications can be generated.

Figure 16A:
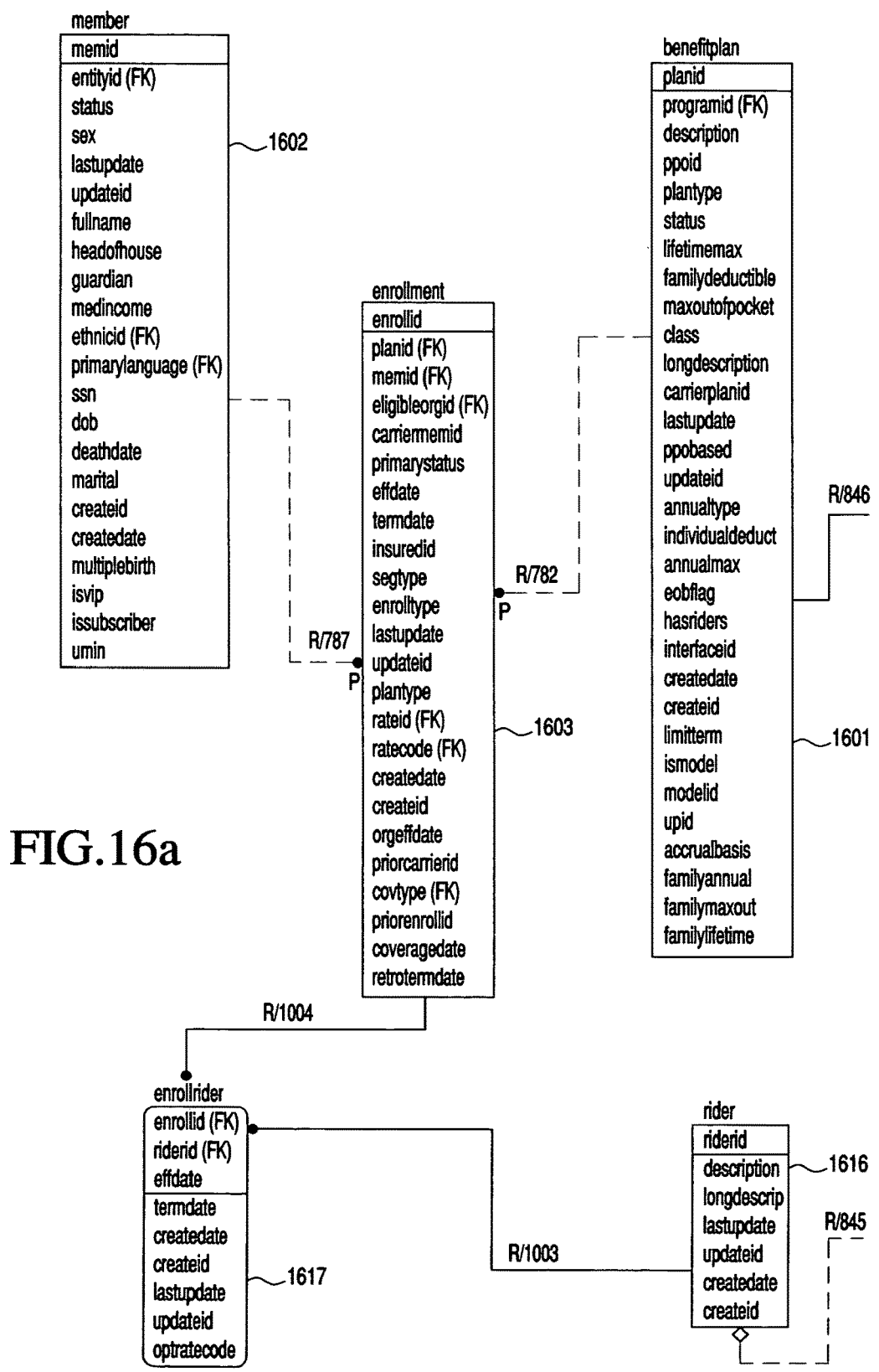
FIGS. 16a through 16d illustrate an inter-relationship of menus for tracking a medical plan member's benefits in the system in accordance with an embodiment of the invention.
Figure 16B:
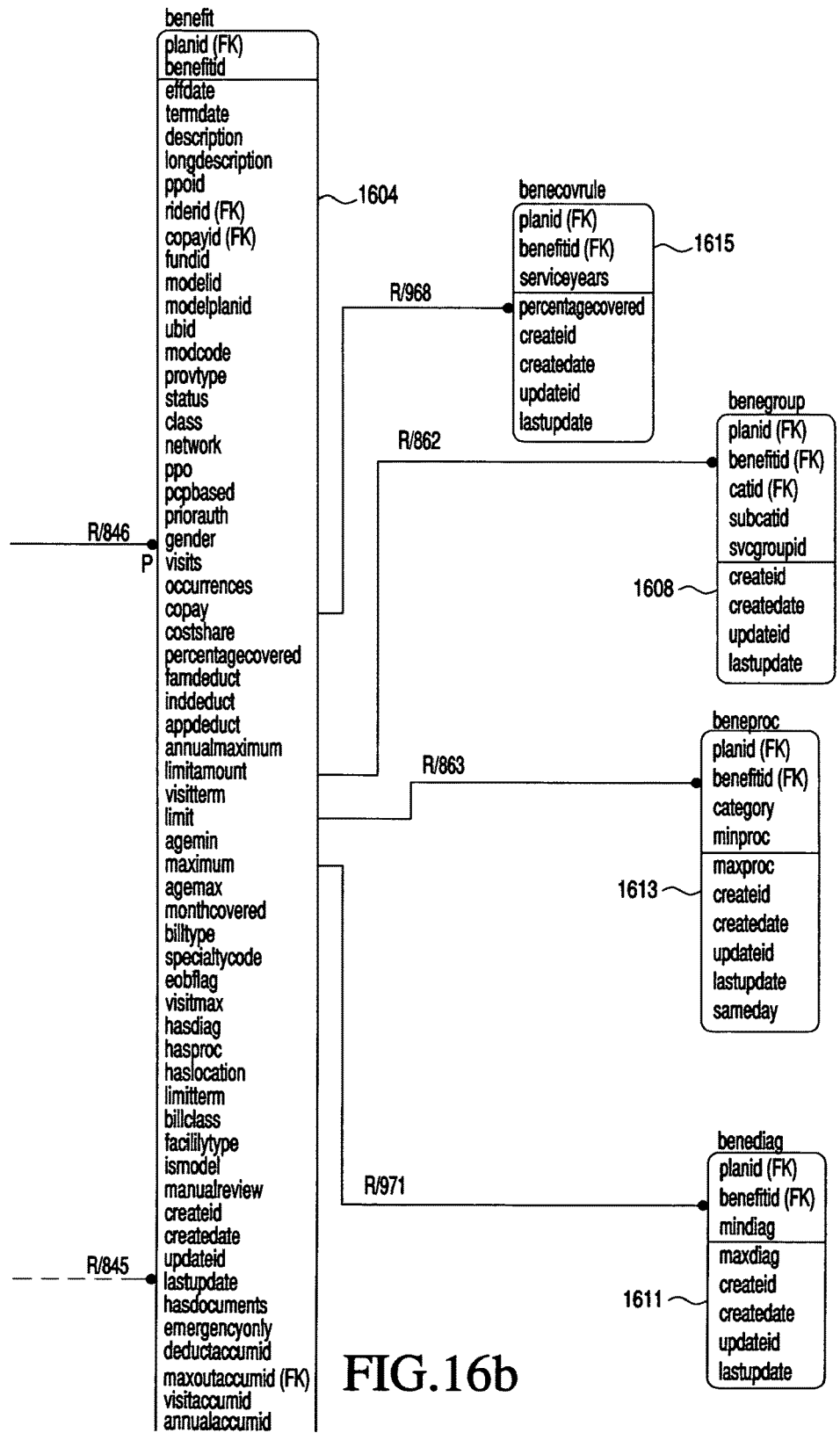
Figure 16C:
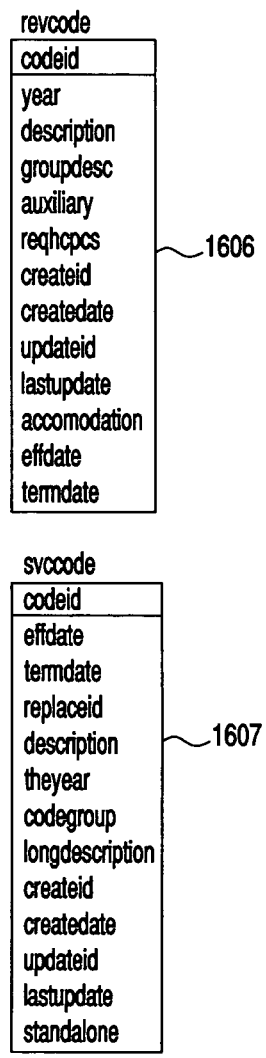
Figure 16D:
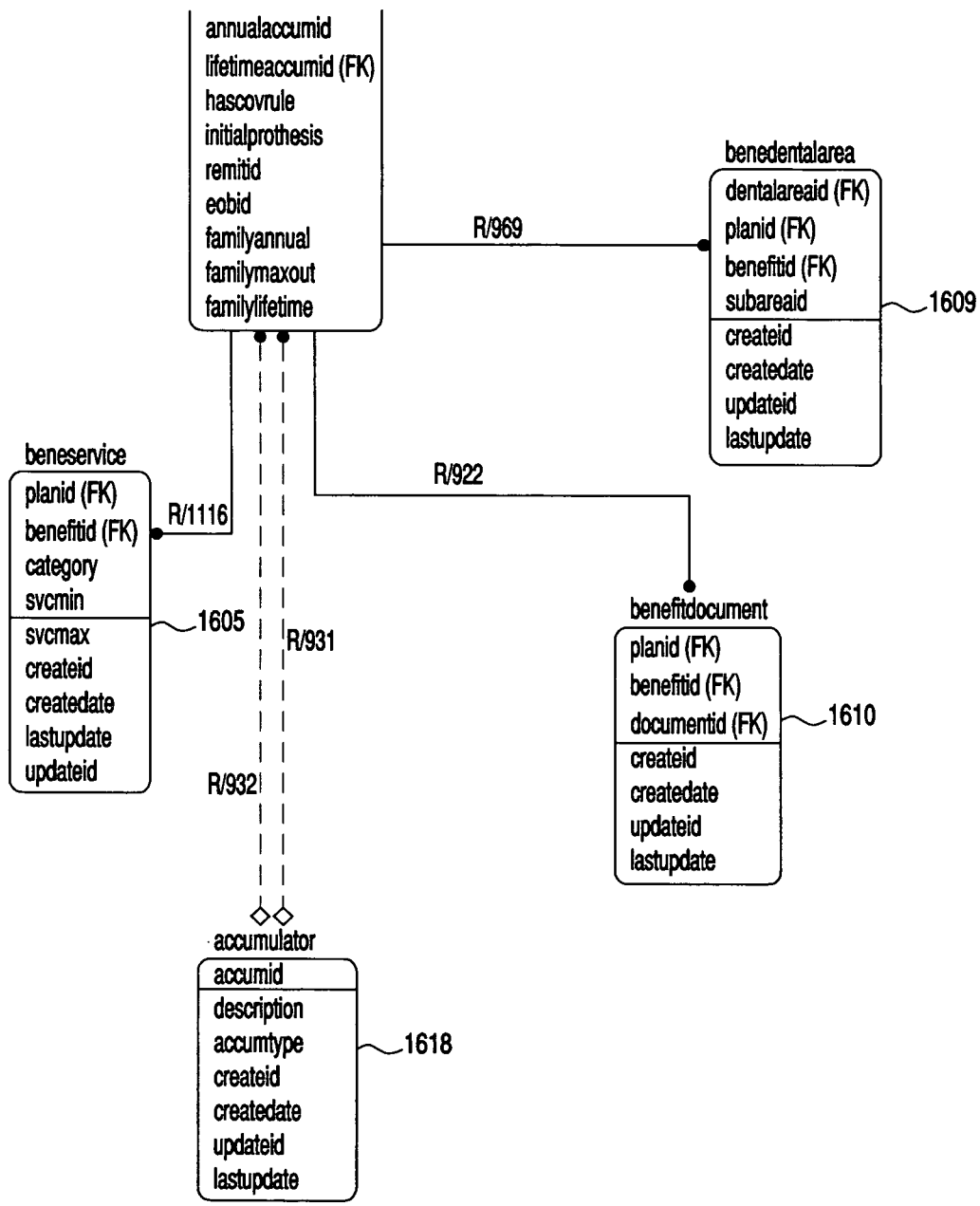

FIGS. 16a through 16d illustrate an inter-relationship of menus for tracking a medical plan member's benefits in the system and for executing the adjudication, scoring, and settlement processes described previously with reference to FIGS. 3, 4, and 5. FIGS. 16a and 16b are viewed horizontally adjacent to each other, and FIGS. 16c and 16d are viewed horizontally adjacent to each other. FIGS. 16a and 16c are viewed vertically adjacent to each other, and FIGS. 16b and 16d are viewed vertically adjacent to each other. A "benefitplan" menu 1601 outlines or organizes information concerning the benefits under the medical plan. Menu 1601 includes menu items specifying an identification of preferred medical service providers ("ppoid"), an HMO, Preferred Provider Option (PPO), or other plan type ("plantype"), maximum lifetime benefits ("lifetimemax"), maximum out-of-pocket expenses ("maxoutofpocket"), family deductible ("familydeductible"), individual deductible ("individualdeduct"), annual maximum benefits for an individual under the medical plan ("annualmax"), a flag for determining whether to print a statement to the medical plan member explaining the termination or end of benefits ("eobflag"), a link to an integrated voice response system ("interfaceid"), the term limits of the medical plan ("limitterm"), a model or production medical plan ("ismodel"), an ID for the model medical plan ("modelid"), how accumulations or deductibles are accumulated ("accrualbasis"), annual maximum benefits for a family under the medical plan ("familyannual"), maximum out of pocket expenses per family ("familymaxout"), maximum family lifetime benefits ("familylifetime").

An "enrollment" menu 1603 is linked to "benefitplan" menu 1601 and records information regarding a member's enrollment into the medical plan. Menu 1603 includes menu items for an identification of the member's employer sponsoring the medical plan ("eligibleorgid"), the member's identification number within the medical plan ("carriermemid"), primary or secondary enrollment status ("primarystatus"), an identification of the insured member if the present member is merely a dependent of the insured member ("insuredid"), internal enrollment managed by the medical plan provider, external enrollment managed by a different medical plan provider, or prospective enrollment ("segtype"), type of enrollment ("enrolltype"), medical, dental, or chiropractic type of medical plan ("plantype"), determining the premium structure ("rateid," "ratecode"), the effective original enrollment date if the original enrollment was in a different medical plan ("orgeffdate"), an identification of the prior medical plan provider offering the prior medical plan ("priorcarrierid"), whether the medical coverage is only for the medical plan member or is also for the member's dependents ("covtype"), the original date of coverage ("coveragedate" which will typically be the same as "orgeffdate"), and a retroactive termination date ("retrotermdate"). As an example of the primary or secondary status of enrollment, if a medical plan member is over the age of sixty-five, the "primarystatus" menu item would indicate "no" because Medicare would be the primary medical plan and the medical plan provider's medical plan would be the secondary medical plan. A child menu (not shown in FIG. 16) extending from "enrollment" menu 1603 may record the medical plan member's prior IDs to permit the use of a new ID without changing the enrollment. As an example, a new ID may be created when the member moves to a new residential address.

A "member" menu 1602 is coupled to "enrollment" menu 1603 and records information for each member of the medical plan. Menu 1602 has menu items for the member's sex ("sex"), head of household ("headofhouse"), guardian ("guardian"), median income ("medincome"), ethnicity ("ethnicid"), primary language ("primarylanguage"), multiple birth status ("multiplebirth"), a flag for access restrictions ("isvip"), an enrolled member as opposed to a dependent of the enrolled member ("issubscriber"), and a universal member identification number ("umin").

A "benefit" menu 1604 is linked to "benefitplan" menu 1601 and stores all eligible benefits under the medical plan of menu 1601. Menu 1604 includes menu items for specifying an account from which to pay benefits under the medical plan ("flindid"), an identification of a model, not production, medical plan ("modelplanid"), a universal benefit identification ("ubid"), modifier code ("modcode"), the type of medical service provider ("provtype"), any prior authorization ("priorauth"), and the family or individual deductibles ("famdeduct," "inddeduct").

Each benefit, identified as first and second claims in FIGS. 4, 5, and 6, is scored, and the benefit or claim with the best score is used to settle the medical claim. When a medical claim is adjudicated, all valid benefits associated with the medical claim are identified by examining the associated service codes mapped to the medical benefit. All of the revenue codes are defined in a "revcode" menu 1606, and all of the service codes are defined in a "svcode" menu 1607. The revenue codes are specified by HIPAA, and the service codes are specified by the American Medical Association (AMA). Various revenue and/or service codes may be grouped together as a single benefit, as identified in a "benegroup" menu 1608 coupled to "benefit" menu 1604. Menu 1608 may be used, for example, to match office visits to a benefit. Benefits may also be found based on a benefit service identified in a "beneservice" menu 1605. Certain dental benefits may be available for specific dental areas, as indicated by a "benedentalarea" menu 1609 linked to "benefit" menu 1604. Dental benefit are explained in more detail hereinafter.

A "benefitdocument" menu 1610 is also coupled to "benefit" menu 1604 and identifies any documentation such as, for example, an X-ray, required to receive the benefit. A "benediag" menu 1611 linked to menu 1604 and identifies any medical procedures required for hospital billing. A "beneproc" menu 1613 coupled to menu 1604 identifies any modifications to the benefit depending on the type of medical procedure performed. A "benecovrule" menu 1615 linked to menu 1604 identifies any variations in benefit coverage. As an example, the benefit coverage for dental check-ups may increase as the number of previous dental check-ups increase to encourage a medical plan member to have preventative dental maintenance. A "rider" menu 1616 also coupled to menu 1604 identifies any riders or additional edits or rules that must be met before the benefit applies. An "enrollrider" menu 1617 coupled to "ridermenu" 1616 and "enrollment" menu 1603 indicates whether the medical plan member has enrolled for the rider. An "accumulator" menu 1618 permits the aggregation of individual accumulator menu items in "benefit" menu 1604. As an example, the individual accumulators may include a first deductible for major medical procedures and a second deductible for minor medical procedures. The use of "accumulator" menu 1618 permits the use of complicated deductible schemes such as automatically meeting the second deductible if the first deductible is met. The use of "accumulator" menu 1618 also eliminates the need for keeping a separate database of the cumulative values of the different accumulators because the cumulative values can be calculated in real-time by searching through the history of medical claims for the medical plan member.

Figure 17A:
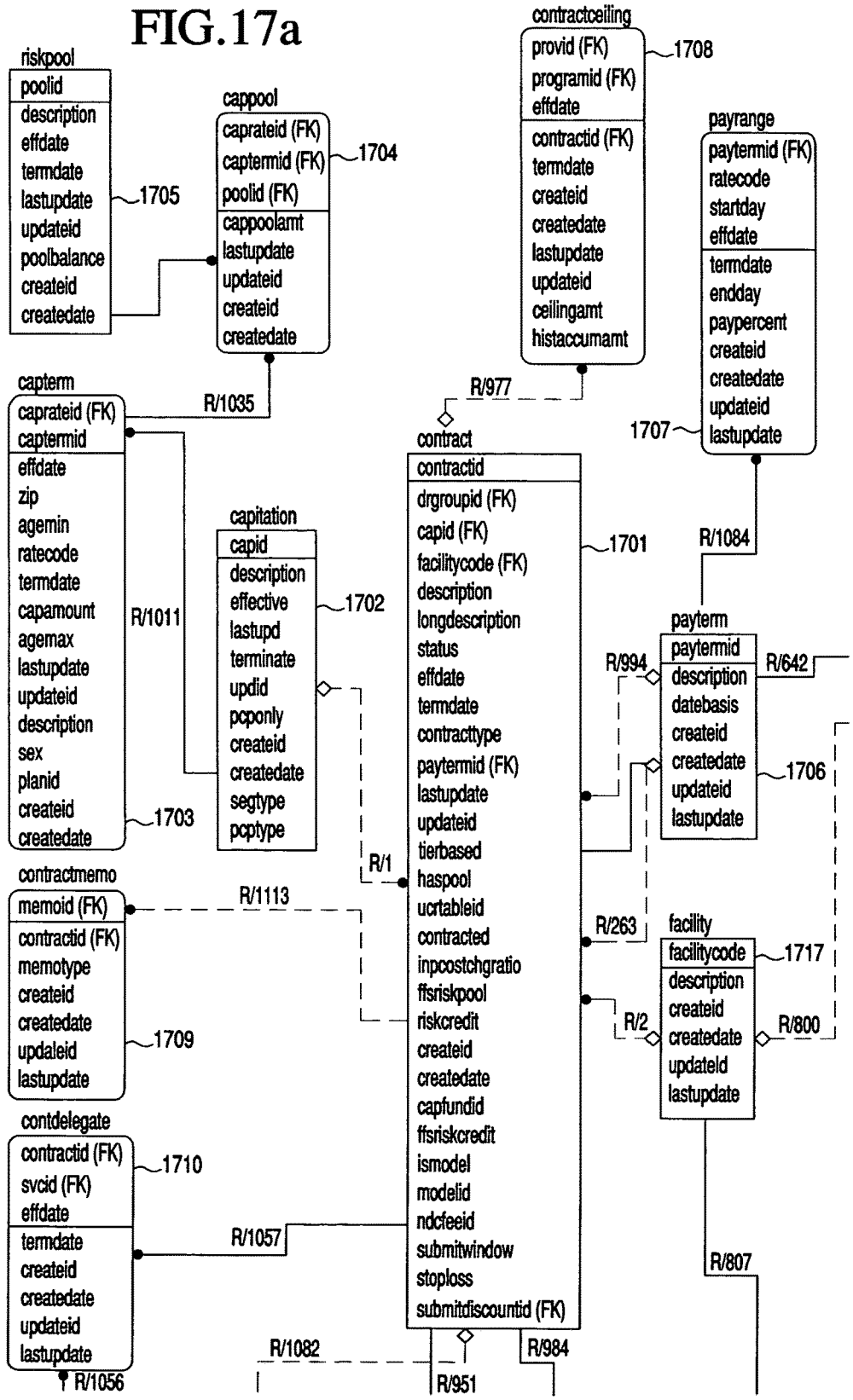
Figure 17B:
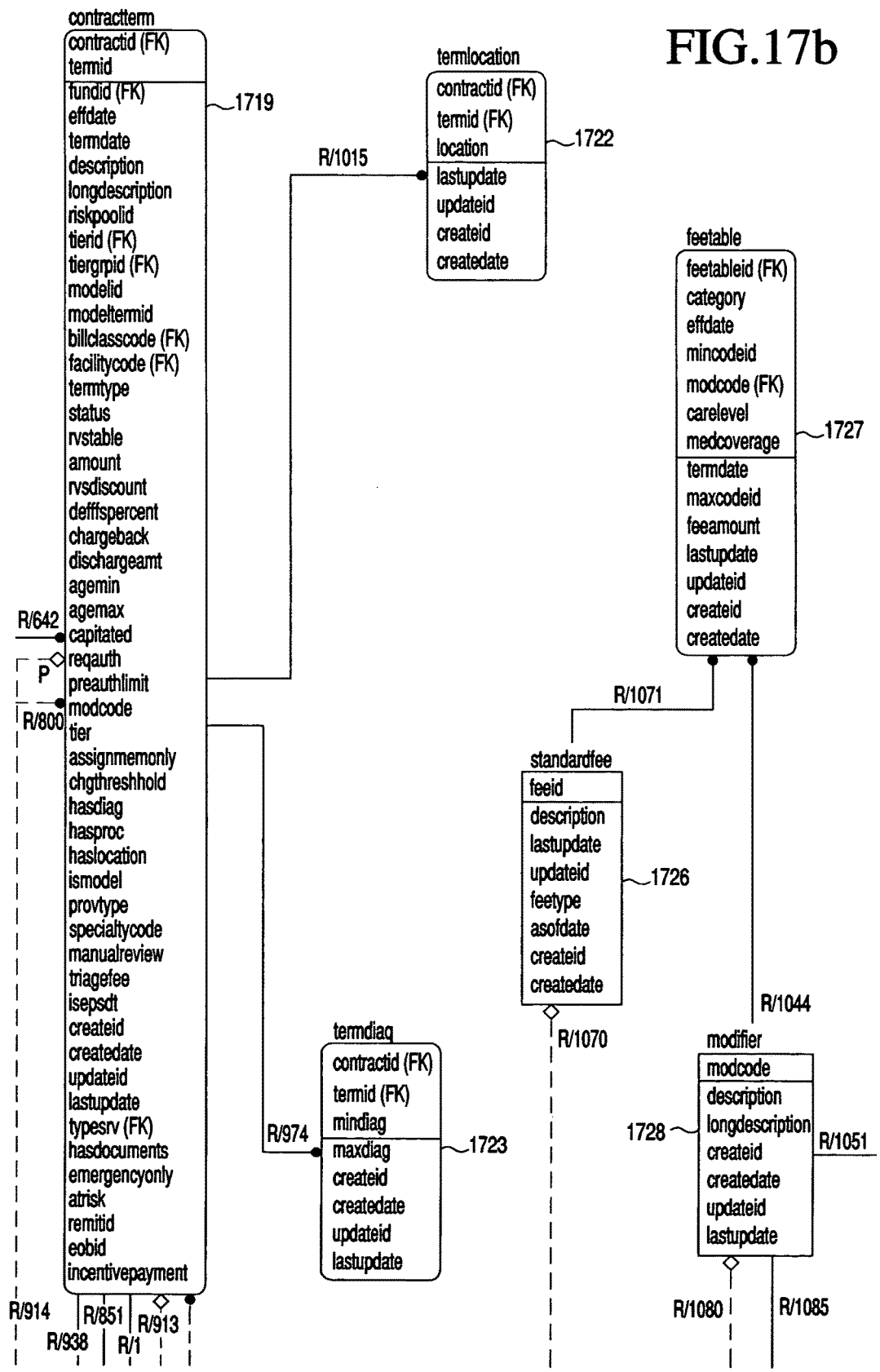
Figure 17D:
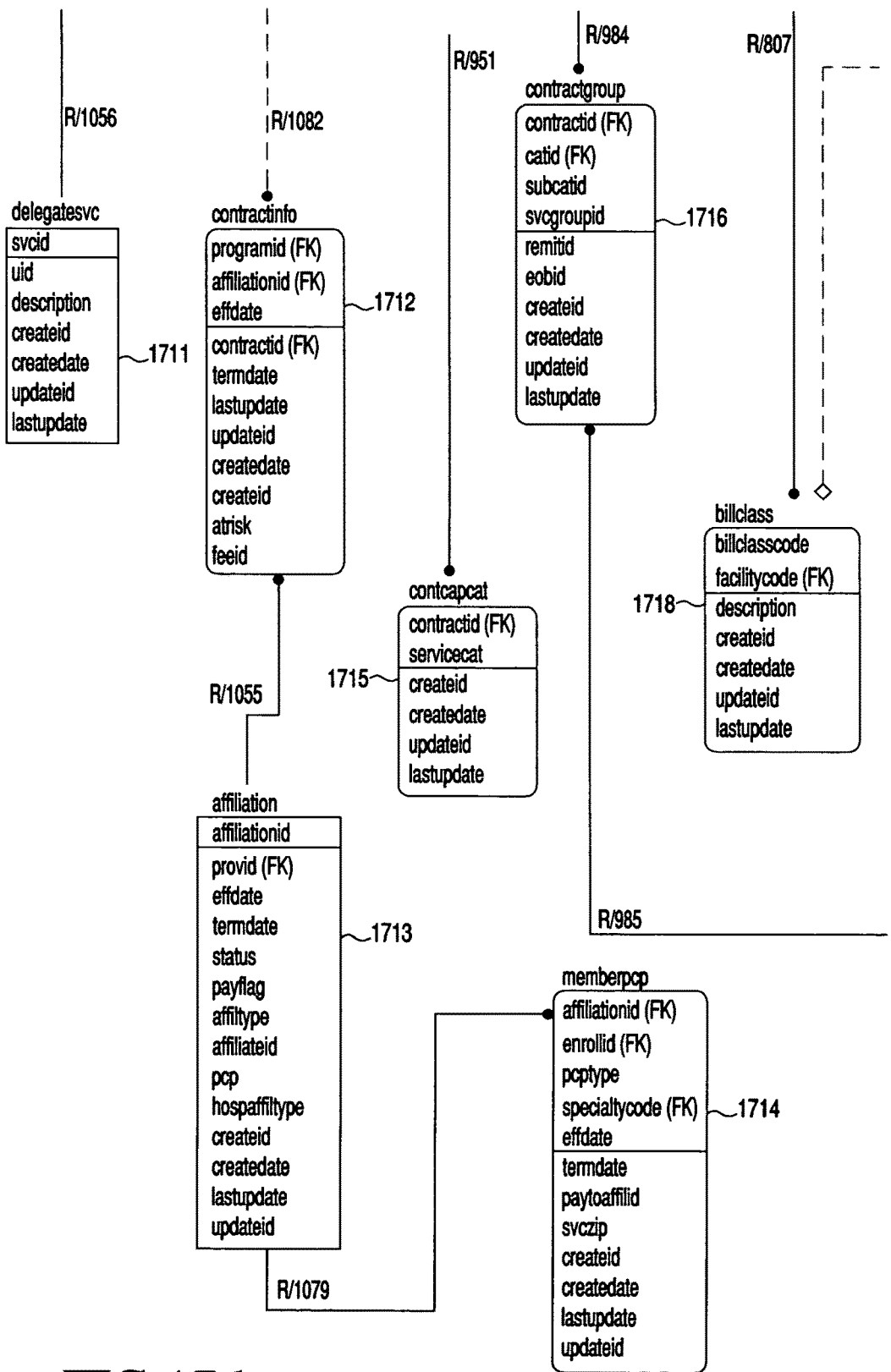
Figure 17E:
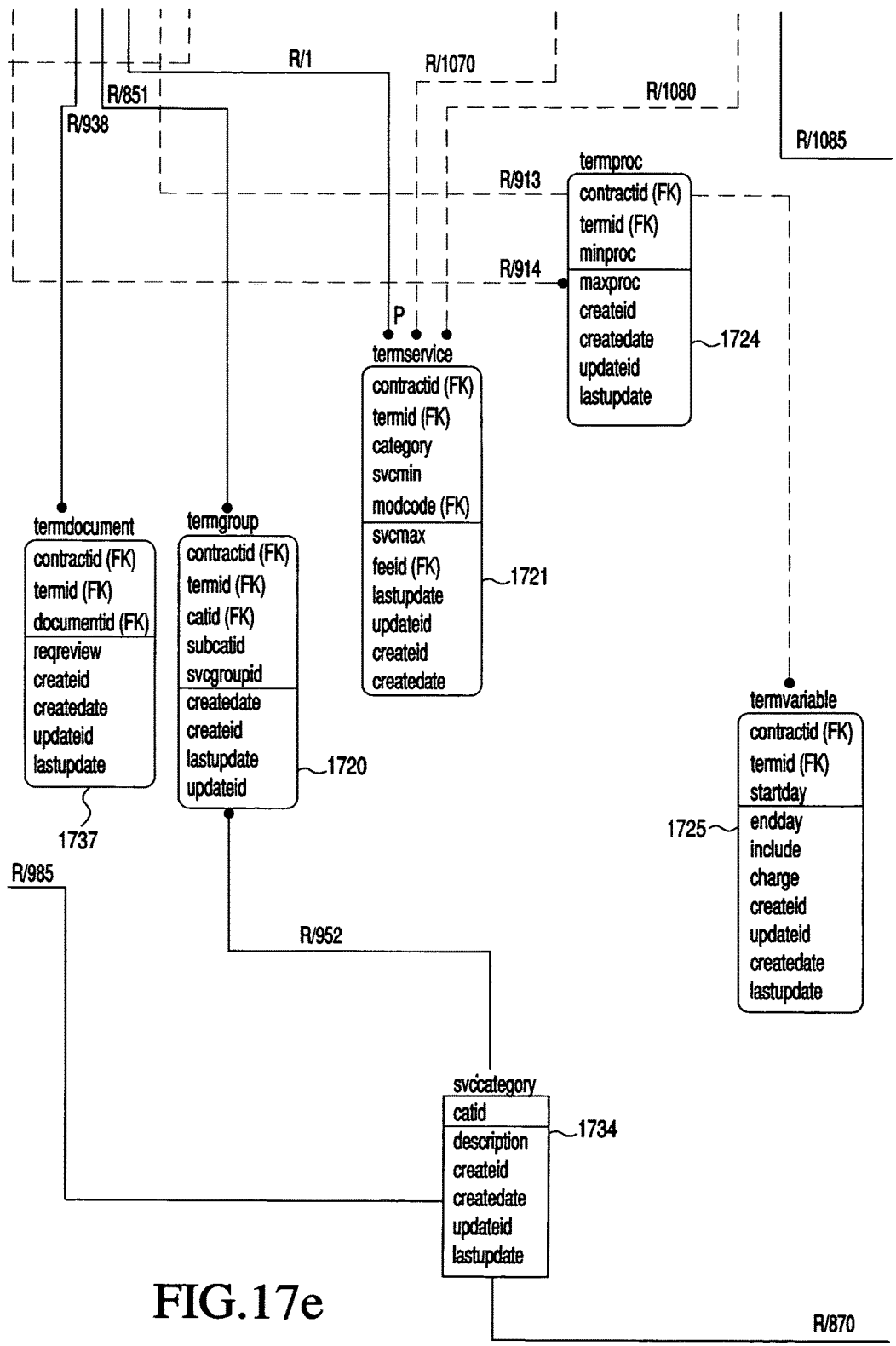
Figure 17F:
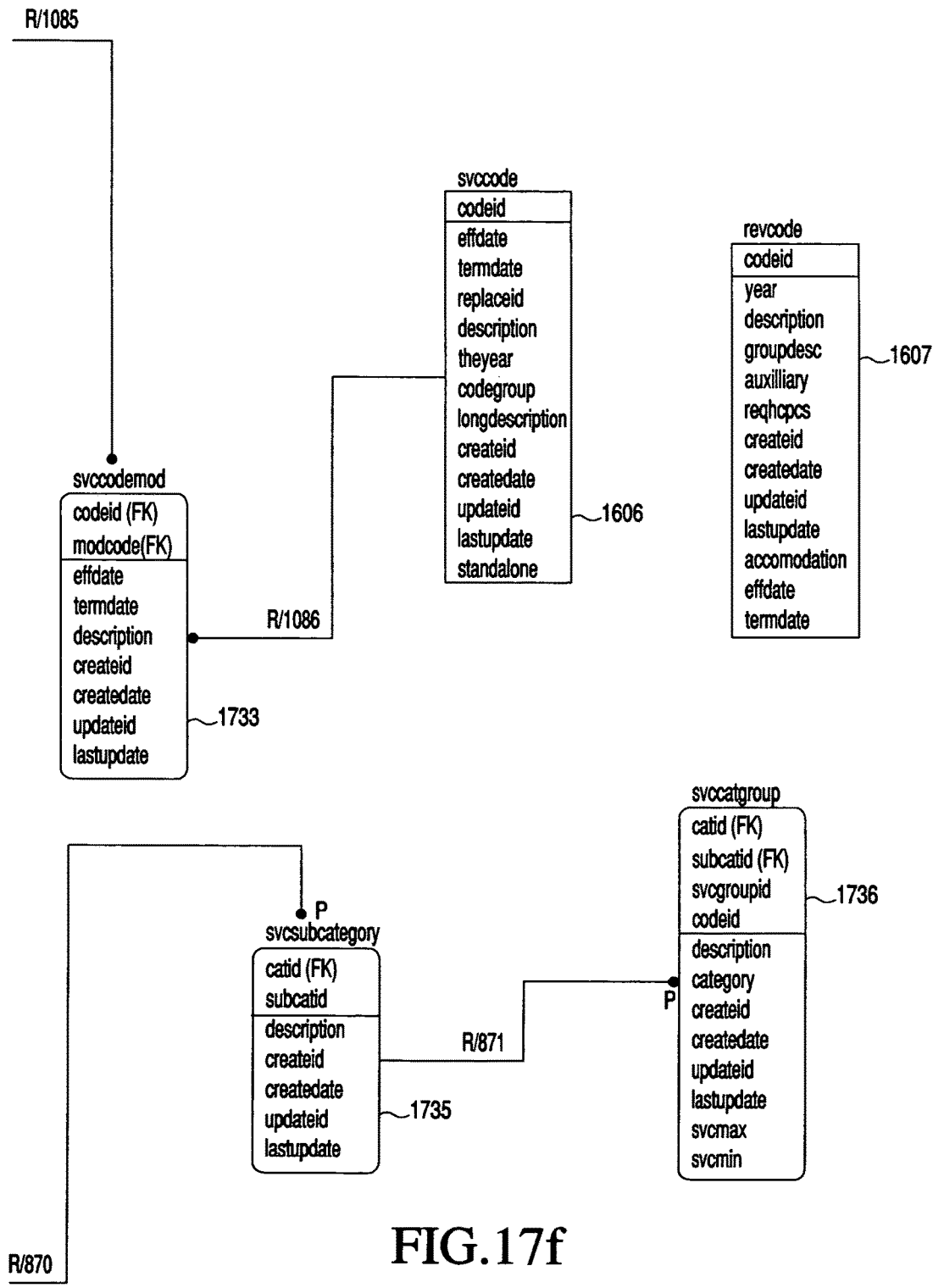

FIGS. 17a through 17f illustrate an inter-relationship of menus for tracking a medical service provider's medical contract with a medical plan provider in the system and for executing the adjudication, scoring, and settlement processes described previously with reference to FIGS. 3, 4, and 5. FIGS. 17a and 17b are viewed horizontally adjacent to each other, and FIGS. 17b and 17c are viewed horizontally adjacent to each other. FIGS. 17d and 17e are viewed horizontally adjacent to each other, and FIGS. 17e and 17f are viewed horizontally adjacent to each other. FIGS. 17a and 17d are viewed vertically adjacent to each other, and FIGS. 17b and 17e are viewed vertically adjacent to each other, and FIGS. 17c and 17f are viewed vertically adjacent to each other. A "contract" menu 1701 outlines or organizes the attributes of a medical contract. Menu 1701 includes menu items for a tier-based contract ("tierbased"), the use of a risk pool ("haspool"), usual, customary, and reasonable table of fees ("ucrtableid"), an in-patient cost-charge ratio ("inpcostchgratio"), a fee for service risk pool ("ffsriskpool"), a model or production contract ("ismodel"), a pharmacy fee table ("ndcfeeid"), an amount of time available to submit a claim after performing the medical procedure ("submitwindow"), and a maximum monetary value for a medical claim ("stoploss").

A "capitation" menu 1702, a "capterm" menu 1703, a "cappool" menu 1704, and a "riskpool" menu 1705 identify any capitation or pre-payment schedules associated with medical contracts for primary care physicians (PCPs), the terms or pay rate of the capitation schedule, a pool or accrual of the capitation fees, and a pool for the risk fees used to pay specialists, respectively. Menus 1702, 1703, 1704, and 1705 are all coupled to "contract" menu 1701. The "capitation" menu 1702 has menu items for identifying the date of the most recent update ("lastupd"), identifying the person creating the last update ("updid"), limiting the capitation schedule to a particular PCP ("pcponly"), identifying types of enrollment segments qualifying for capitation ("segtype"), and identifying the type of PCP using the capitation schedule ("pcptype"). The "capterm" menu 1703 has menu items for identifying various capitation categories including the zip code of the patient ("zip"), the minimum age of the patient ("agemin"), the capitation rate associated with the zip code, age, or gender of the patient ("capamount"), the maximum age of the patient ("agemax"), and the sex or gender of the patient ("sex"). The "riskpool" menu 1705 includes a menu item for tracking the balance of the risk pool ("poolbalance") where any remaining balance at the end of a period may be divided between the medical service provider and the medical plan provider.

A "payterm" menu 1706 is linked to "contract" menu 1701 to specify the payment terms under the medical contract between the medical plan provider and the medical service provider, and a "payrange" menu 1707 is linked to menu 1706 and specifies any adjustments or discounts to the payment terms. Menus 1706 and 1707 can be used to provide quick pay discounts such as, for example, a two percent discount if payment is made within ten days and/or slow pay penalties such as, for example, a two percent penalty if payment is made after thirty days. A "contractceiling" menu 1708 is coupled to "contract" menu 1701 to identify a maximum payment amount ("ceilingamt") and a cumulative payment amount in a medical plan ("histaccumamt"). As an example, menu 1708 can be used for government medical contracts that have payment ceilings and limit the amount of money paid to medical service providers per period. A "contractmemo" menu 1709 is also coupled to "contract" menu 1701 and identifies any informative memoranda that are attached to the contract, and a "contdelegate" menu 1710 and a "delegatesvc" menu 1711 identify any services that are delegated to a third party provider under the contract.

A "contractinfo" menu 1712 is linked to "contract" menu 1701 to identify any medical affiliations under the contract and identify a medical service provider's relationship to a medical line of business. An "affiliation" menu 1713 is coupled to menu 1712 to describe the affiliation, and a "memberpcp" menu 1714 is linked to menu 1713 for identifying any assignments of medical plan members to medical service providers for primary or specialty medical care. The "contractinfo" menu 1712 includes menu items for indicating whether the medical service provider is at risk for paying a referral fee or the fee for the medical procedure if specific medical services are referred out because the medical service provider is contracted to performed those services ("atrisk"), and an identification of a usual, customary, and reasonable fee table ("feeid"). The "affiliation" menu 1713 includes menu items for indicating if checks can be sent to the medical service provider ("payflag"), the type of affiliation ("affiltype"), an identification of the affiliation ("affiliateid"), and the type of hospital affiliation ("hospaffiltype").

A "contcapcat" menu 1715 is linked to "contract" menu 1701 and identifies a global capitation category and permits carve-outs or exceptions to the capitation. Carve-outs are typically used for the supply of Durable Medical Equipment (DME), the performance of vision or eye-related services, or the performance of pharmaceutical services. For instance, if a medical plan provider contracts with a medical laboratory to perform all medical laboratory services for all medical plan members, and also contracts with a hospital that has its own medical laboratory, then menu 1715 can be used to establish exceptions to the global capitation for all medical plan members who have their medical laboratory work performed by the hospital's medical laboratory.

A "contractgroup" menu 1716 is also linked to "contract" menu 1701 and permits the denial of a medical claim for a medical procedure because the medical procedure is not covered in the contract. A "facility" menu 1717 is linked to menu 1701, and a "billclass" menu 1718 is linked to menu 1717 to permit the identification of the facility and associated parameters at which a medical procedure was performed.

A "contractterm" menu 1719 is coupled to "payterm" menu 1706 and "facility" menu 1717 to identify the payment terms for a single medical procedure or a set of medical procedures. The single medical procedure is identified in a "termservice" menu 1721, and the set or group of medical procedures is identified in a "termgroup" menu 1720. A category of medical procedures is identified in a "svccategory" menu 1734, and the category of medical procedures can be subdivided in a "svcsubcategory" menu 1735 and can be further subdivided in a "svccatgroup" menu 1736. Menu 1734 is coupled to "termgroup" menu 1720 and "contractgroup" menu 1716; menu 1735 is coupled to menu 1734; and menu 1736 is coupled to menu 1735.

A "termlocation" menu 1722 is coupled to "contractterm" menu 1719 to identify valid locations associated with specific medical procedures. For example, the valid location for heart surgery is a hospital, not the surgeon's office. A "termdiag" menu 1723 and a "termproc" menu 1724 are linked to "contractterm" menu 1719 and identify any diagnosis restrictions or procedure restrictions associated with the contract. A "termvariable" menu 1725 is coupled to "termproc" menu 1724 and identifies a variable per diem fee to be paid. As an example, a medical contract with a hospital may pay the hospital a flat fee of $1,000 per day for the first three days that a patient remains in the hospital and a flat fee of $500 per day for any subsequent days that the patient remains in the hospital. A "standardfee" menu 1726 is coupled to "termservice" menu 1721 and identifies the standard fee associated with a single medical procedure. A "feetable" menu 1727 coupled to menu 1726 and specifies a table or list of standard fees.

A "modifier" menu 1728 is coupled to menus 1721 and 1727 and identifies any modifications or adjustments to be applied to the standard fees based upon an apportionment of the medical services. As an example, menu 1728 may be used to process medical claims for an X-ray. A radiologist evaluating the X-ray may submit the medical claim with a modifier indicating the claim is for the professional services related to the X-ray, and a hospital providing the X-ray facility may submit another medical claim with a modifier indicating the claim is for the technical component related to the X-ray. Menu 1728 apportions the X-ray fee between the radiologist and the hospital. As another example, a surgical procedure may involve primary, secondary, and tertiary medical procedures. Menu 1728 is used to pay the primary procedure at the full rate and to pay the secondary and tertiary procedures at a modified or discounted rate. As a further example, a PCP who sees a patient during a scheduled appointment will be compensated at the standard rate while the PCP who sees the same patient during an emergency will be compensated at a modified rate.

A "moddiscount" menu 1729 is coupled to menu 1728 to indicate any discounts to be applied to the standard fees. A "svccodemod" menu 1733 is coupled to "modifier" menu 1727 and specifies how to modify the service code based on the fee modifiation. The "svccode" menu 1606 is linked to menu 1733.

A "drgrate" menu 1730 identifies a reimbursement rate for a diagnostic related grouping, which is currently used for Medicare billing. An "asaunit" menu 1732 assigns a predetermined number of units to each medical procedure, and each medical service provider can be assigned a reimbursement rate per unit. The number of units for the medical procedure multiplied by the reimbursement rate equals the monetary value of the medical procedure for the medical servie provider. As an example, menus 1730 and 1732 can be used in place of or in addition to the per diem fees in "termproc" menu 1724.

Figure 18A:
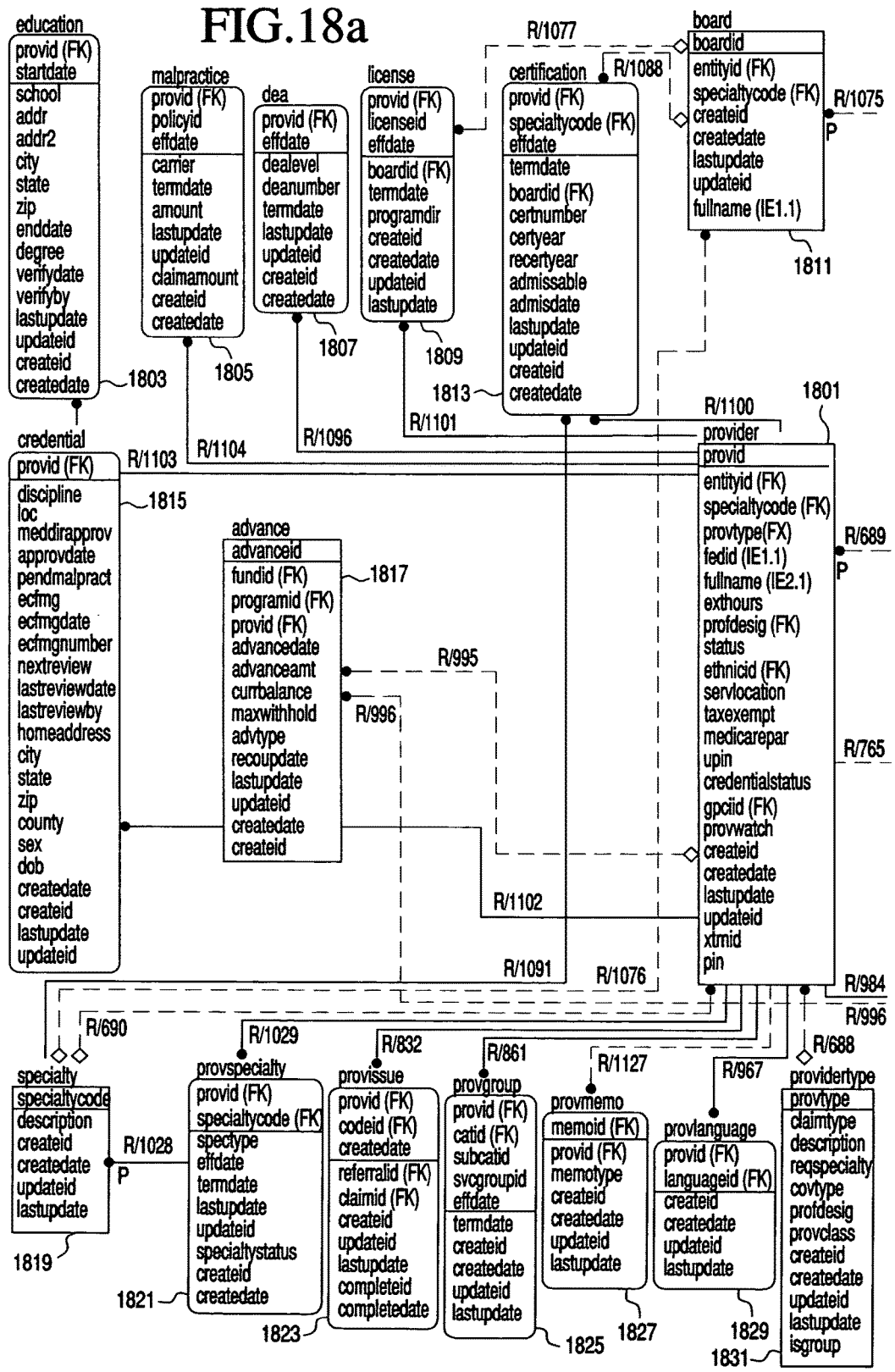
FIGS. 18a and 18b illustrate an inter-relationship of menus for tracking a medical service provider's information in the system in accordance with an embodiment of the invention.
Figure 18B:
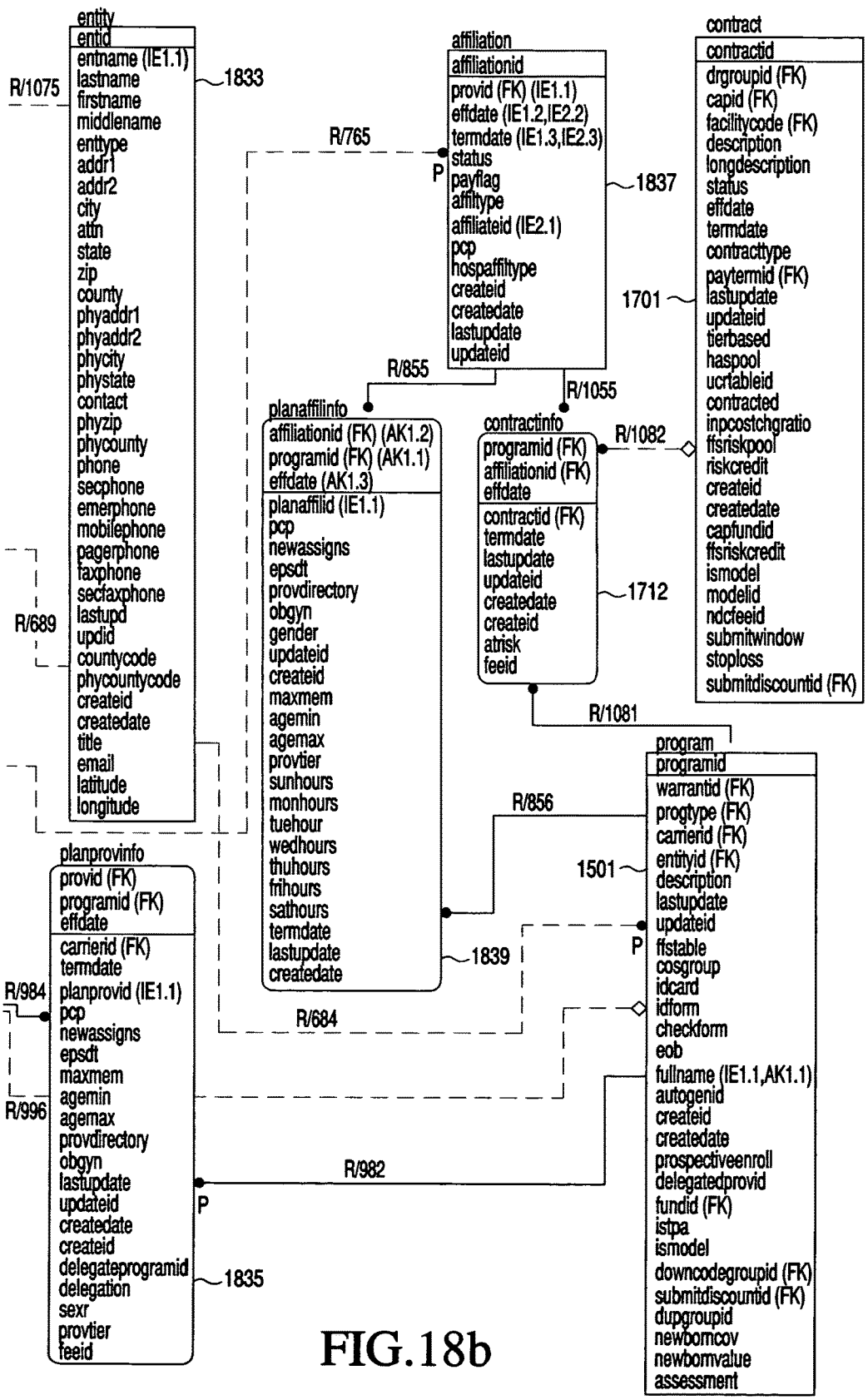

FIGS. 18*a* and 18*b* illustrate an inter-relationship of menus for tracking a medical service provider's information in the system. FIGS. 18*a* and 18*b* are viewed horizontally adjacent to each other. A "provider" menu 1801 outlines or organizes the attributes of the medical service provider. In one embodiment, menu 1801 is the same as menu 1004 in FIG. 10. A "malpractice" menu 1805 in FIG. 18 is coupled to menu 1801 and specifies the medical service provider's malpractice insurance company and policy, and a "dea" menu 1807 is also coupled to menu 1801 and specifies the medical service provider's Drug Enforcement Agency (DEA) information.

A "license" menu 1809 is linked to "provider" menu 1801 and indicates the medical service provider's medical licenses, and a "certification" menu 1813 is also linked to menu 1801 and indicates the medical service provider's medical specialty certifications. A "speciality" menu 1819 is coupled to menu 1801 to list codes for all possible medical specialty designations. Examples of medical specialty designations include, but are not limited to, pediatrics, cardiology, and family practice. A "board" menu 1811 is coupled to menus 1809, 1813, and 1819 to identify the medical boards that granted the medical licenses, specialty certifications, and specialty designations to the medical service provider. A "provspecialty" menu 1821 is also coupled to menu 1801 and indicates the medical service provider's specialties. Menu 1821 uses the medical specialty codes from "specialty" menu 1819. A "credential" menu 1815 is coupled to menu 1801 and specifies the education credentials of the medical service provider, and an "education" menu 1803 linked to menu 1815 specifies the medical service provider's medical school. The "credential" menu 1815 includes menu items for any disciplinary action against the medical service provider ("discipline"), approval by the medical director ("meddirapprov"), any pending malpractice charges against the medical service provider ("pendmalpract"), authorization to prescribe medicine ("ecfmgdate," "ecfmgnumber"), a review of the medical service provider's performance and/or credentials ("nextreview," "lastreviewdate," "lastreviewby").

An "advance" menu 1817 is coupled to "provider" menu 1801 and "credential" menu 1815 and identifies a monetary advance that may be provided to the medical service provider. The monetary advance may be used to encourage the medical service provider to establish his/her practice in a rural area where a shortage of medical service providers exists. The "advance" menu 1817 includes a menu item for limiting the amount of money that must be paid back to the medical plan provider each period to pay off the advance ("maxwithhold"). A "provissue" menu 1823 is also coupled to menu 1801 and tracks any issues or problems that may arise with a medical service provider. A "provgroup" menu 1825 is linked to menu 1801 and establishes categories of medical services or procedures that the medical service provider may perform. For example, if the medical service provider is a podiatrist, then menu 1825 will specify all medical services or procedures related to podiatry and will not include medical services or procedures such as brain surgery. Therefore, the podiatrist who submits a medical claim for brain surgery will be denied even though the podiatrist's medical contract may cover brain surgery.

A "provmemo" menu 1827 is also linked to "provider" menu 1801 and indicates any memoranda associated with the medical service provider's file. A "provlanguage" menu 1829 is coupled to menu 1801 and specifies all languages that the medical service provider speaks, and a "providertype" menu 1831 is also coupled to menu 1801 and specifies the type of the medical service provider such as, for example, a physician or a hospital. Menu 1831 includes menu items for indicating the typical type of medical claims submitted by the medical service provider ("claimtype"), a medical specialty ("reqspecialty"), type of medical coverage such as, for example, medical, dental, or chiropractic ("covtype"), professional designation of the medical service provider ("profdesig"), classes of medical service providers such as, for example, long-term versus short term care facilities ("provclass"), and whether more than one doctor is usually assigned to this type of medical facility ("isgroup").

An "entity" menu 1833 is linked to "provider" menu 1801 and indicates the medical service provider's demographic information, and a "planprovinfo" menu 1835 is also linked to menu 1801 and indicates the medical service provider's relationship to a particular medical line of business of a medical plan provider. Menu 1833 is functionally similar to "qentity" menu 1003 in FIG. 10. Menu 1835 in FIG. 18 includes menu items for specifying a medical service provider's different medical service provider IDs in different medical plans ("planprovid"), whether the medical service provider performs early periodic screening diagnostic testing for minors (epsdt), a maximum number of medical plan members that may be assigned to the medical service provider ("maxmem"), age restrictions for the medical plan members that may be assigned to the medical service provider ("agemin," "agemax"), whether the medical service provider has a listing in a medical service provider directory ("provdirectory"), whether the medical service provider has a preference for male or female patients ("sexr"), and a system-level preference for assigning new medical plan members to this medical service provider ("provtier"). Menu 1835 is further linked to "advance" menu 1817 because the size of the monetary advance depends upon the medical plan to which the medical service provider is contracted. An "affiliation" menu 1837 is coupled to menu 1801 and specifies any affiliations that the medical service provider has with other medical service providers, and a "planaffilinfo" menu 1839 is coupled to menu 1837 and identifies the medical service provider's relationship to other medical lines of business of the medical plan provider through the medical service provider's affiliations. The "affiliation" menu 1837 includes a menu item for indicating whether the affiliation is still active or not ("status"). The "planaffilinfo" menu 1837 is ftunctionally similar to "planprovinfo" menu 1835.

The "contractinfo" menu 1712 is linked to "affiliations" menu 1837, and the "contract" menu 1701 is linked to menu 1712. Additionally, the "program" menu 1501 is coupled to the "contractinfo" menu 1712, the "planaffilinfo" menu 1839, the "entity" menu 1833, the "planprovinfo" menu 1835, and the "advance" menu 1817.

Figure 19A:
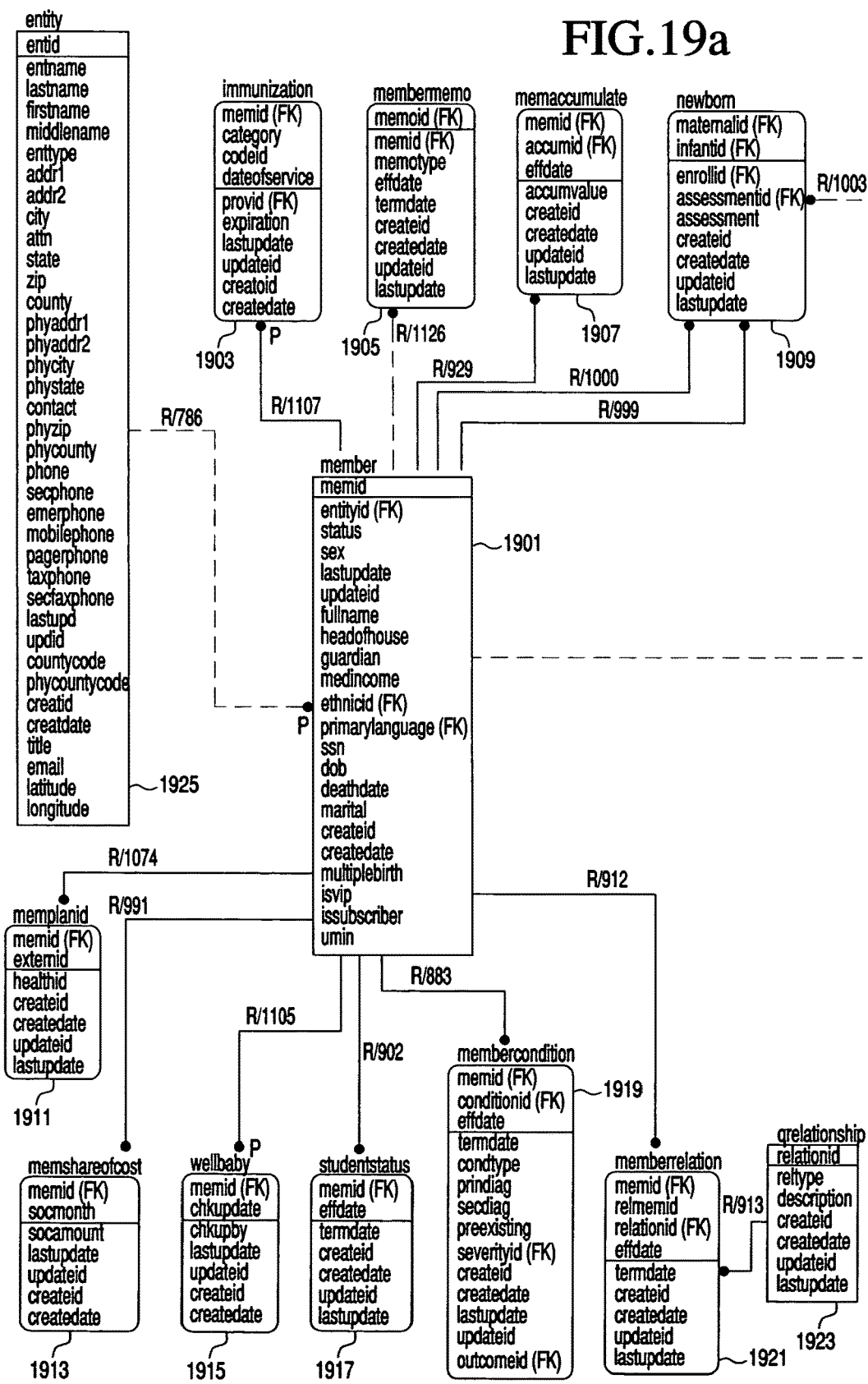
FIGS. 19a and 19b illustrate an inter-relationship of menus for tracking a medical plan member's status in the system in accordance with an embodiment of the invention.
Figure 19B:
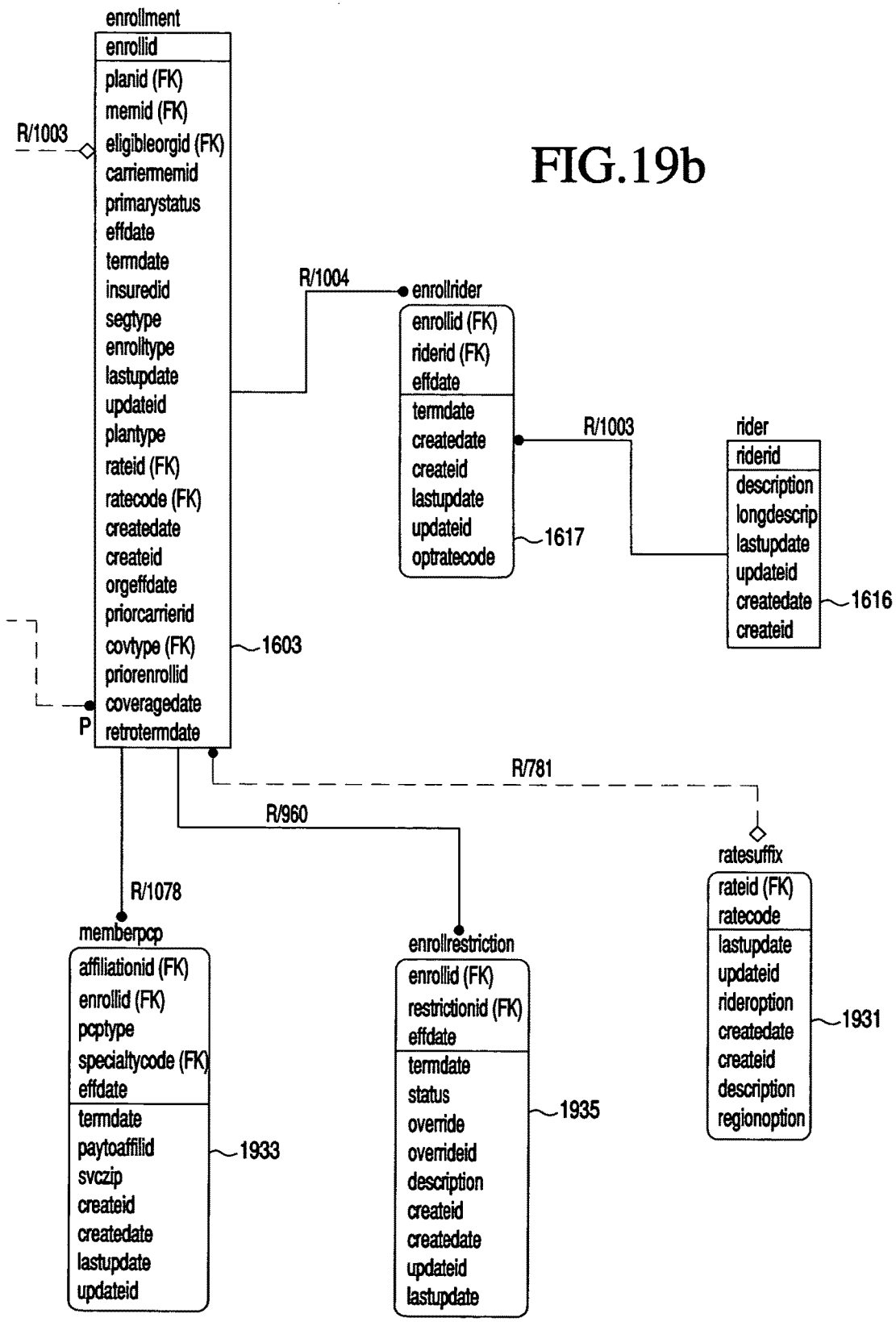

FIGS. 19a and 19b illustrate an inter-relationship of menus for tracking a medical plan member's status in the system. FIGS. 19a and 19b are viewed horizontally adjacent to each other. A "member" menu 1901 outlines or organizes the attributes of the medical plan member. An "entity" menu 1925 is coupled to menu 1901 to identify the demographic and other personal information about the member. Menu 1925 is functionally similar to "qentity" menu 1003 in FIG. 10 and "entity" menu 1833 in FIG. 18.

An "immunization" menu 1903 in FIG. 19 is coupled to "member" menu 1901 and organizes the medical plan member's historical immunization records including any expiration dates of the immunizations ("expiration"), and a "membermemo" menu 1905 is also coupled to menu 1901 and indicates any memoranda related to the member. A "memaccumulator" menu 1907 is linked to menu 1901 and tracks the medical plan member's deductible. Menu 1907 includes an "accumid" ID so that if the medical plan member switches medical plans in the middle of an accumulation period, the accumulation of the previous medical plan can be carried over to the new medical plan. A "newborn" menu 1909 is also linked to menu 1901 to track the member's newborn children. The use of menu 1909 eliminates the problems associated with tracking newborns who are not typically recognized as a dependent member in a medical plan for up to sixty days after birth. Menu 1909 permits the identification of the newborn child even though the newborn child is still not recognized as a separate or distinct member in the system.

A "memplanid" menu 1911 is coupled to "member" menu 1901 and indicates the member's medical coverage outside of the present medical plan, and a "memshareofcost" menu 1913 is also coupled to menu 1901 and indicates the portion or share of long-term medical costs subsidized by the government. A "wellbaby" menu 1915 is linked to menu 1901 and records medical check-ups for infant dependents of the member, and a "studentstatus" menu 1917 is also linked to menu 1901 and indicates the student status for any of the member's dependents who have reached the age of majority. A "membercondition" menu 1919 is coupled to menu 1901 and specifies the medical plan member's medical condition such as, for example, diabetic or pregnant. The medical conditions may be temporary or permanent.

A "memberrelation" menu 1921 is linked to "member" menu 1901 and indicates any relationships of the member to another medical plan member, and a "qrelationship" menu 1923 is linked to menu 1921 and specifies the type of relationship to the other medical plan member. As an example, a mother would have a relationship to her minor child, in which case menu 1921 would indicate the existence of a relationship between the mother and the minor child and in which case menu 1923 would indicate the type of relationship between the mother and the minor child as parent-child.

The "enrollment" menu 1603 is coupled to both "member" menu 1901 and "newborn" menu 1909, and the "enrollrider" menu 1617 is coupled to menu 1603, and the "rider" menu 1616 is coupled to menu 1617. A "ratesuffix" menu

1931 is coupled to "enrollment" menu 1603 and defines valid rate codes for the premium structure. A "memberpcp" menu 1933 is also coupled to menu 1603 and indicates the PCP and specialists assigned to the medical plan member. An "enrollrestriction" menu 1935 is also coupled to menu 1603 and indicates any suspensions of the member's eligibility.

Figure 20A:
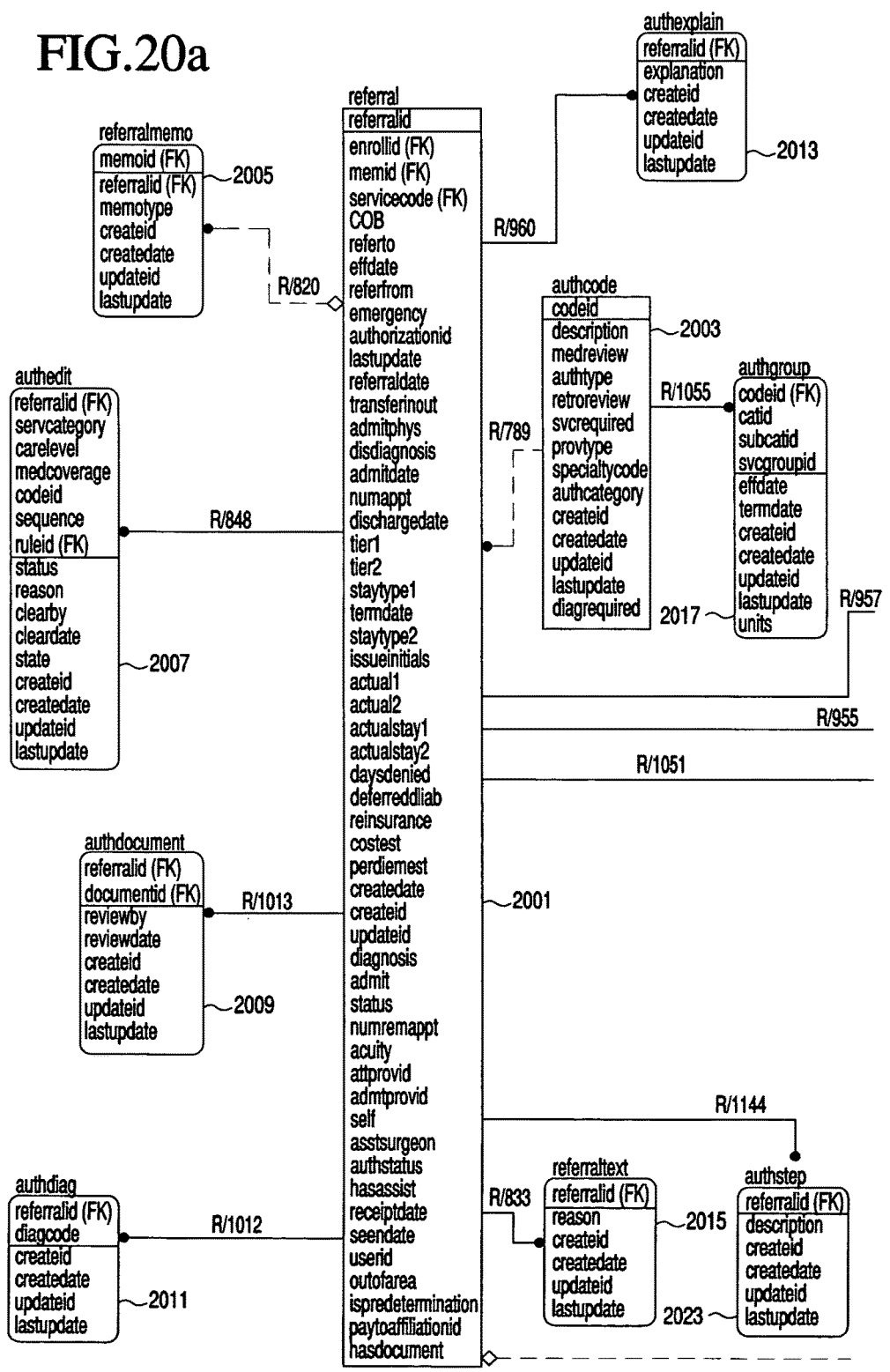
FIGS. 20a and 20b illustrate an inter-relationship of menus for a medical referral in the system in accordance with an embodiment of the invention.
Figure 20B:
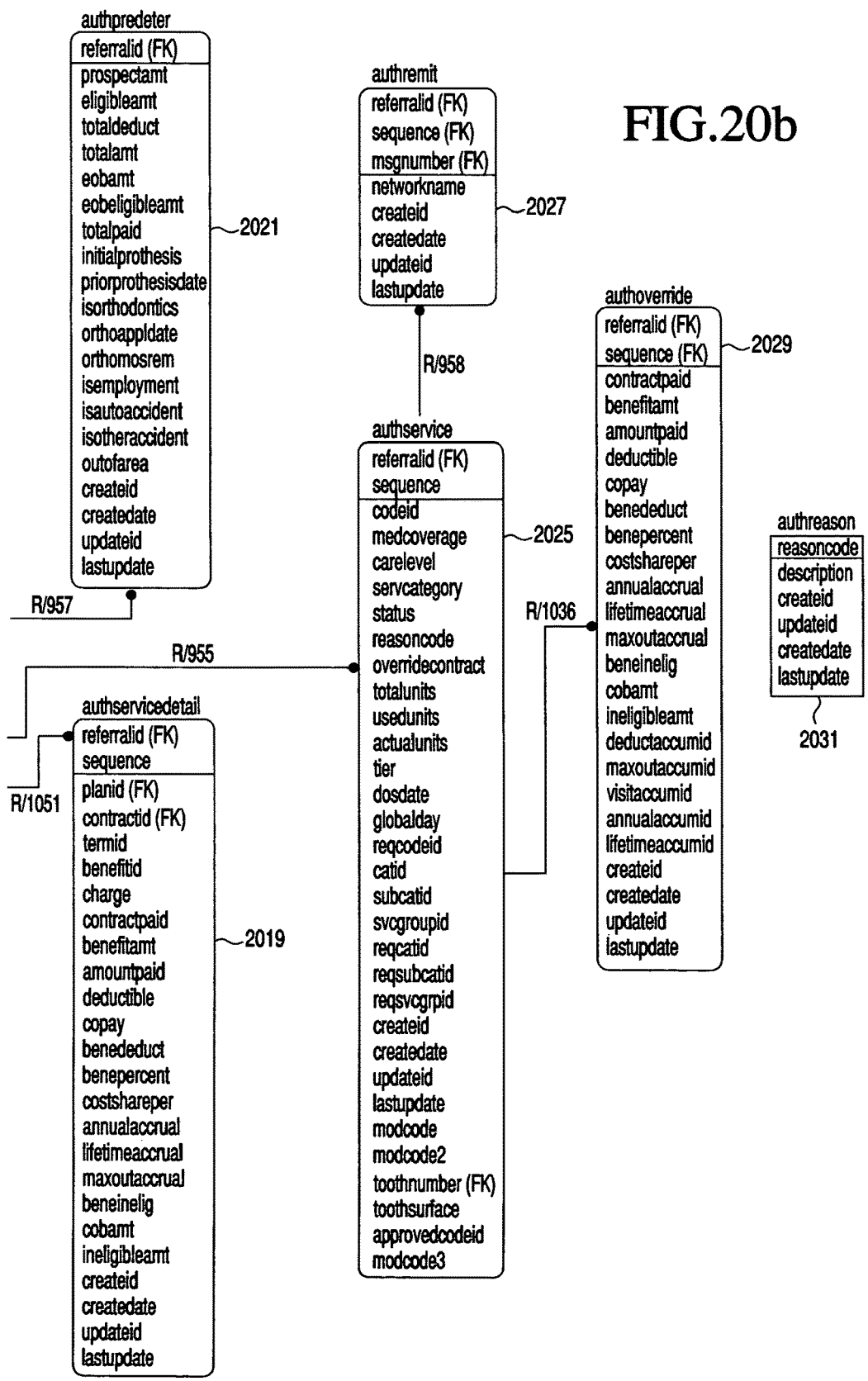

FIGS. 20*a* and 20*b* illustrate an inter-relationship of menus for a medical referral in the system. FIGS. 20*a* and 20*b* are viewed horizontally adjacent to each other. A "referral" menu 2001 outlines or organizes the attributes of a referral. A referral is a type of pre-authorization for a medical procedure. Menu 2001 includes menu items for identifying the medical service provider receiving the referral ("referto"), the medical service provider making the referral ("referfrom"), whether the referral occurred during a medical emergency ("emergency"), an authorization code ("authorizationid"), the medical service provider admitting the patient ("admitphys"), a medical diagnosis upon discharge ("disdiagnosis"), an authorization for types of treatment such as, for example, intensive care or regular ("type1," "type2"), the number of days authorized for each type of treatment ("staytype1," "staytype2"), the actual type of treatment received ("actual1," "actual2"), the actual number of days for each treatment ("actualstay1," "actualstay2"), any third party liability for the cost of the referral ("deferredliab"), a cost estimate ("costest"), a per diem estimate made at the time of authorizing the referral ("perdiemest"), the number of remaining appointments ("numremappt"), acute or chronic symptoms ("acuity"), the attending medical service provider ("attprovid"), the admitting medical service provider ("admitprovid"), a self referral ("self"), a medial procedure occurring out of the local area in which the medical plan member resides ("outofarea"), whether a predetermination was made earlier for this referral ("ispredetermination"), and whether the referral has authorization documents ("hasdocument"). An "authcode" menu 2003 is linked to menu 2001 and defines the types of authorizations required by "referral" menu 2001. An "authgroup" menu 2017 is linked to menu 2001 and groups a package of services with the referral.

A "referralmemo" menu 2005 is linked to menu 2001 and permits the attachment of memoranda to the referral, and an "authedit" menu 2007 is also linked to menu 2001 and enables an adjudication of the referral in a manner similar to that for adjudicating a medical claim. An "authdocument" menu 2009 is coupled to menu 2001 and permits the attachments of authorization documents such as, for example, X-rays to a referral, and an "authdiag" menu 2011 is also coupled to menu 2001 and describes the diagnosis related to the referral.

An "authexplain" menu 2013 is coupled to menu 2001 and permits a free form test to be attached to the referral, and a "referraltext" menu 2015 is also coupled to menu 2001 and provides a user description of the referral. An "authservicedetail" menu 2019 and an "authpredeter" menu 2021 are both linked to "referral" menu 2001 and track additional information from a medical claim and from the adjudication. An "authstep" menu 2023 is also linked to menu 2001 and describes how the referral was processed and why the referral was approved or rejected.

An "authservice" menu 2025 is coupled to menu 2001 and assigns medical services to a referral. An "authremit" menu 2027 is coupled to menu 2025 and attaches messages that are printed on the remittance advice sent back to the medical service provider. An "authoverride" menu 2029 is also coupled to menu 2025 and permits an override of the decision made by "authservicedetail" menu 2019 and "authservice" menu 2025. An "authreason" menu 2031 defines reasons codes to be used with "authremit" menu 2027.

Figure 21A:
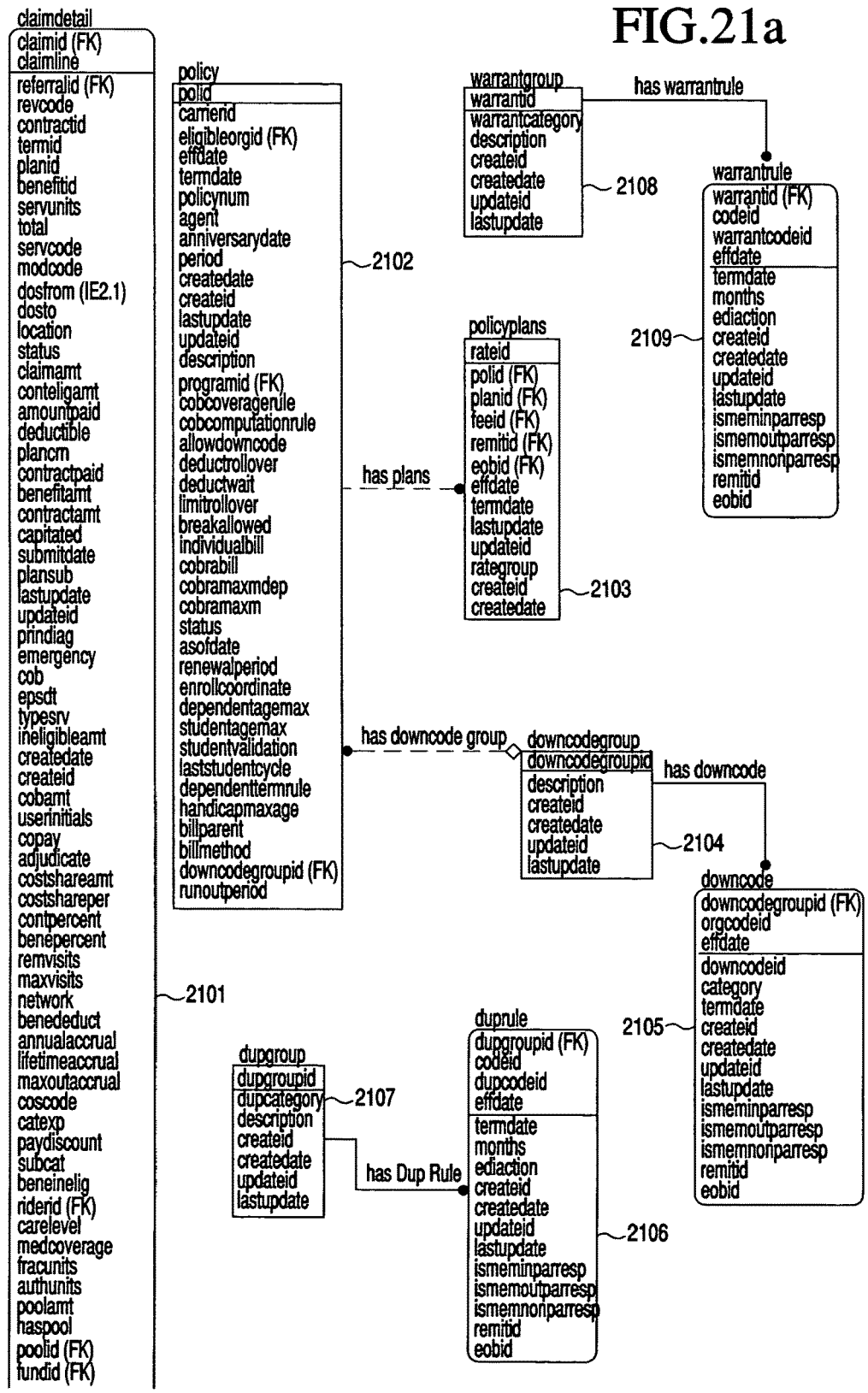

FIGS. 21*a* and 21*b* illustrate an inter-relationship of menus for a down-coding process in the system. FIGS. 21*a* and 21*b* are viewed vertically adjacent to each other. The down-coding process can apply when evaluating a medical claim for a medical service provider and for a medical plan member or patient. A "claimdetail" menu 2101 outlines the components of a medical claim, and a "policy" menu 2102 organizes the components of a medical policy. Each medical policy has a plurality of medical plans or policy plans, as indicated by a "policyplans" menu 2103. In addition to identifying valid or covered medical procedure codes, the medical policy also identifies a group of medical procedure codes that are not covered by the policy, as indicated by a "downcodegroup" menu 2104, and the medical procedure codes to be used as substitutes for the non-covered medical procedure codes are indicated in a "downcode" menu 2105. Menus 2103 and 2104 are coupled to menu 2102, and menu 2105 is coupled to menu 2104. Each medical policy can have its own unique group of down-coding codes.

A "dupgroup" menu 2107 provides a feature similar to down-coding, except that menu 2107 searches for duplicative medical procedure codes. A "duprule" menu 2106 is linked to menu 2107 and provides the rules for handling a duplicative code. Duplicative medical procedure codes are not limited to identical codes in subsequent medical claims, but can also include codes for similar or more-encompassing medical procedures. As an example, a duplicative code can include a first medical claim having a porcelain filling for a particular tooth on a particular patient on a particular day and a second medical claim having an amalgam filling for the same tooth on the same patient on the same day. Requests for pre-approval of medical claims or actual medical claims containing duplicative medical procedure codes are denied or rejected. Each medical policy can have its own unique group of duplicative codes. Portions of the duplicative code process in menus 2106 and 2107 can also be used with the down-coding process in menus 2104 and 2105. For example, after a medical procedure code in a medical claim is down-coded, the substituted medical procedure code can be checked under the duplicative code rules. In particular, referring back to FIG. 7, a check for duplicative codes can be performed between steps 750 and 760 and/or between steps 751 and 760.

A "warrantgroup" menu 2108 identifies the warranties associated with the medical policy, and a "warrantrule" menu 2109 linked to menu 2108 provides the rules for handling the warranty.

Figure 22A:
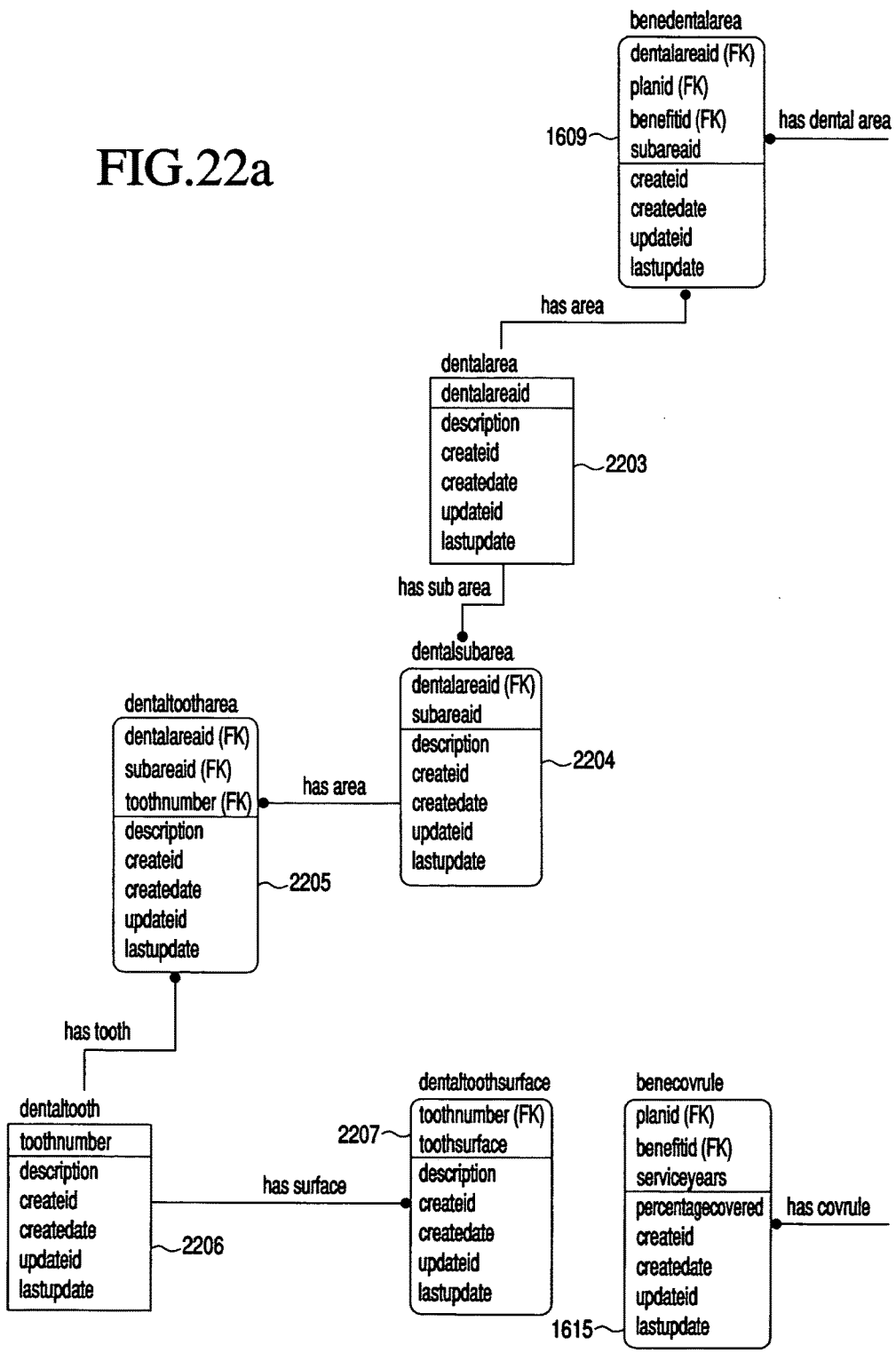

FIGS. 22*a*, 22*b*, and 22*c* illustrate an inter-relationship of menus for tracking a member's dental benefits. FIGS. 22*a* and 22*b* are viewed horizontally adjacent to each other, and FIGS. 22*b* and 22*c* are viewed vertically adjacent to each other. The "benefit" menu 1604 is coupled to the "benecovrule" menu 1615 and the "benefitdentalarea" menu 1609. A "dentalarea" menu 2203 is coupled to menu 1609 to define a dental area to which the medical procedure was applied and for which a medical benefit is requested, and a "dentalsubarea" menu 2204 is coupled to menu 2203 and defines a dental sub-area to which the medical procedure was applied and for which a medical benefit is requested. A "dentaltootharea" menu 2205 identifies a tooth area; a "dentaltooth" menu 2206 identifies a particular tooth; and a "dentaltoothsurface" menu 2207 identifies a tooth surface to which the medical procedure was applied and for which a medical benefit is requested. As an example, a dental area can be the upper or lower jaw; a dental subarea can be the right or left side; a dental tooth area can be molars, bicuspids, cuspids, or incisors; a dental tooth can be a specific one of the molars, bicuspids, cuspids, or incisors; and a tooth surface can be an inner, outer, or top surface.

Therefore, an improved method of processing medical claims method of adjudicating medical claims/method of managing medical contracts/method of down-coding medical claims is provided to overcome the disadvantages of the prior art. The method can be performed real-time without a time delay of weeks or even a day. The method described herein provides a more cost efficient, more reliable, and more accurate method of processing medical claims/method of adjudicating medical claims/method of managing medical contracts/method of down-coding medical claims, and the method is both patient-oriented and medical service provider-oriented.

Although the invention has been described with reference to specific embodiments, it is understood by those skilled in the art that various changes and modifications may be made without departing from the spirit or scope of the invention. For instance, the numerous details set forth herein such as, for example, the initial value in FIG. 3 and the first and second values in FIG. 4 are provided to facilitate the understanding of the invention and are not provided to limit the scope of the invention. Furthermore, one skilled in the art understands that the menus in FIGS. 8 through 22 many be modified to include additional menu items, additional parent-child menu relationships, or the like. Accordingly, the disclosure of embodiments of the invention is intended to be illustrative of the scope of the invention and is not intended to be limiting. It is intended that the scope of the invention shall be limited only to the extent required by the appended claims.

What is claimed is:

1. A method of interactively processing in real-time, using multiple inter-related menus accessible on a computer, a medical claim in a medical claim transaction initiated by a submission of the medical claim via an electronic medium to a medical plan provider on behalf of a patient making a visit to a medical service provider, the method comprising:

prior to a termination of the patient's visit to the medical service provider:

receiving, at the computer, a request to process a medical claim, wherein the request to process a medical claim is provided to the computer and processed thereby in accordance with the multiple inter-related menus presented to a user via web pages on a display, the inter-related menus including a user role menu linked to a role activity menu, the role activity menu being linked to an activities menu, wherein the role activity menu assigns one or more activities to different user roles in the user role menu and defines access privileges to one or more activities within the activities menu, wherein a request to process a medical claim is an activity within the activities menu which is accessible in accordance with a user role assigned to a medical service provider user, and further wherein the medical service provider user is uniquely identified to the computer via a user menu which includes an item for receiving a one-way encrypted password from the user to identify the user as a medical service provider user prior to displaying the activities menu for a medical service provider user role, including the request to process a medical claim;

performing, by a computer, an analysis routine in accordance with the request to process a medical claim comprising:

identifying, by the computer, a most-recently-received medical claim for the patient received from the medical service provider, where the most-recently-received medical claim can be the medical claim or a different medical claim;

analyzing, by the computer, the most-recently-received medical claim in order to determine whether the most-recently-received medical claim is in condition for approval, the analyzing including one or more of checking an eligibility of the patient in a medical plan offered by the medical plan provider, comparing a medical claim history of the patient to the medical claim in order to check for a duplicate claim, comparing a contract between the medical service provider and the medical plan provider to a medical procedure to which the medical claim transaction pertains, and comparing a medical benefit of the patient in the medical plan to the medical procedure to which the medical claim transaction pertains, wherein comparing a medical benefit of the patient is performed in accordance with multiple inter-related menus including a benefits menu coupled to a revenue code menu, a service code menu and an accumulator menu for aggregating multiple accumulator items in the benefits menu;

determining that the most-recently-received medical claim is not in condition for approval;

rejecting, by the computer, the most-recently-received medical claim;

identifying, by the computer, at least one reason the most-recently-received medical claim was rejected and identifying, by the computer, an alteration to the most-recently-received medical claim that would place the medical claim in condition for approval;

transmitting, by the computer, a message containing information regarding the rejection of the most-recently-received medical claim and the at least one reason for rejection to the medical service provider via the electronic medium, wherein the message enables a creation of the different medical claim and the different medical claim represents an alteration of the most-recently-received medical claim;

analyzing, by the computer, the different medical claim in order to determine whether the different medical claim is in condition for approval, the analyzing including one or more of checking eligibility of the patient in a medical plan offered by the medical plan provider, comparing a medical claim history of the patient to the different medical claim in order to check for a duplicate claim, comparing a contract between the medical service provider and the medical plan provider to a medical procedure to which the different medical claim transaction pertains, and comparing a medical benefit of the patient in the medical plan to the medical procedure to which the different medical claim transaction pertains, wherein comparing a medical benefit of the patient is performed in accordance with multiple inter-related menus including a benefits menu coupled to a revenue code menu, a service code menu and an accumulator menu for aggregating multiple accumulator items in the benefits menu;

determining, by the computer, that the different medical claim is in condition for approval;

informing, by the computer, the medical service provider via the electronic medium that the different medical claim has been approved;

determining a monetary value to the medical service provider of the medical procedure to which the different medical claim transaction pertains;

determining a monetary value to the patient of the medical procedure to which the different medical claim transaction pertains;

wherein determining the monetary values to the medical service provider and the patient of the medical procedure includes accessing a database storing a plurality of requirements and conditions for multiple claims, wherein the different medical claim meets at least some of the requirements and conditions for a first and second of the multiple claims, scoring each of the first and second of the multiple claims in accordance with predetermined criteria related to each of the requirements and conditions of each of the first and second of the multiple claims the different medical claim meets;

determining the monetary values based on scoring results; and informing the medical service provider via the electronic medium that the different medical claim has been approved and informing the medical service provider of the monetary values of the medical procedure to the medical service provider and to the patient; and terminating, by the computer, the medical claim transaction.

2. The method of claim 1 wherein:
the electronic medium is the Internet.

3. The method of claim 1 wherein:
the analysis routine is completed within five minutes of the receipt of the medical claim.

4. The method of claim 1 wherein:
the method is transaction-based.

5. An interactive, real-time claims processing method using multiple inter-related menus accessible on a computer, comprising:

receiving, by a computer, a request for pre-approval of a medical claim for payment related to a medical procedure via an electronic medium on behalf of a patient of a medical service provider while the patient is in an office of the medical service provider for the medical procedure, wherein the request for pre-approval of a medical claim is provided to the computer and processed thereby in accordance with multiple inter-related menus presented to a user via web pages on a display, the inter-related menus include a user role menu linked to a role activity menu, the role activity menu being linked to an activities menu, wherein the role activity menu assigns one or more activities to different user roles in the user role menu and defines access privileges to one or more activities within the activities menu, wherein the request for pre-approval of a medical claim is an activity within the activities menu which is accessible in accordance with a user role assigned to a medical service provider user, and further wherein the medical service provider user is uniquely identified to the computer via a user menu which includes an item for receiving a one-way encrypted password from the user to identify the user as a medical service provider user prior to displaying the activities menu for a medical service provider user role, including the request for pre-approval of a medical claim; and while the patient remains in the office of the medical service provider, performing a pre-approval process in accordance with the request comprising:

receiving, by the computer, the request for pre-approval via the electronic medium;

analyzing, by the computer, the request for pre-approval in order to determine whether the request for pre-approval is in condition for approval, the analyzing including one or more of checking eligibility of the patient in a medical plan offered by a medical plan provider, comparing a medical claim history of the patient to the medical claim in order to check for a duplicate claim, comparing a contract between the medical service provider and the medical plan provider to the medical procedure to which the medical claim pertains, and comparing a medical benefit of the patient in the medical plan to the medical procedure to which the medical claim pertains, wherein comparing a medical benefit of the patient is performed in accordance with multiple inter-related menus including a benefits menu coupled to a revenue code menu, a service code menu and an accumulator menu for aggregating multiple accumulator items in the benefits menu;

determining that the request for pre-approval is not in condition for approval;

rejecting, by the computer, the request for pre-approval;

identifying, by the computer, at least one reason the request for pre-approval was rejected; and transmitting, by the computer, a message containing information regarding the rejection of the request for pre-approval and the at least one reason for rejection to the medical service provider via the electronic medium in order to enable the creation of an altered request for pre-approval on behalf of the patient comprising the request for pre-approval as altered according to the information;

receiving, by the computer, the altered request for pre-approval;

analyzing, by the computer, the altered request for pre-approval in order to determine whether the altered request for pre-approval is in condition for approval, the analyzing including one or more of checking eligibility of the patient in a medical plan offered by a medical plan provider, comparing a medical claim history of the patient to the medical claim in order to check for a duplicate claim, comparing a contract between the medical service provider and the medical plan provider to the medical procedure to which the medical claim pertains, and comparing a medical benefit of the patient in the medical plan to the medical procedure to which the medical claim pertains, wherein comparing a medical benefit of the patient is performed in accordance with multiple inter-related menus including a benefits menu coupled to a revenue code menu, a service code menu and an accumulator menu for aggregating multiple accumulator items in the benefits menu;

approving the altered request for pre-approval, receiving and approving, by the computer, an altered medical claim associated with the altered request for pre-approval;

informing, by the computer, the medical service provider via the electronic medium that the altered medical claim associated with the altered request for pre-approval has been approved;
    determining a monetary value to the medical service provider of the medical procedure to which the altered medical claim pertains;
    determining a monetary value to the patient of the medical procedure to which the altered medical claim pertains;
    wherein determining the monetary values to the medical service provider and the patient of the medical procedure includes
    accessing a database storing a plurality of requirements and conditions for multiple claims, wherein the altered medical claim meets at least some of the requirements and conditions for a first and second of the multiple claims,
    scoring each of the first and second of the multiple claims in accordance with predetermined criteria related to each of the requirements and conditions of each of the first and second of the multiple claims the altered medical claim meets;
    determining the monetary values based on scoring results; and informing, by the computer, the medical service provider of a monetary value of the medical procedure to the medical service provider and to the patient.

6. The method of claim 5 wherein:
receiving the request for pre-approval and performing the pre-approval process occur within a three-minute period of time.

7. The method of claim 5 further comprising:
while the patient remains in the office of the medical service provider, verifying correctness of claim information in the altered medical claim.

8. The method of claim 5, further comprising:
electronically transferring the monetary value for the medical procedure to the medical service provider to an account of the medical service provider.

9. The method of claim 8 wherein:
electronically transferring the monetary value for the medical procedure to the medical service provider occurs within five days of receiving the altered medical claim and occurs absent manual intervention.

10. The method of claim 5 wherein:
the electronic medium comprises the Internet.

\* \* \* \* \*